US006849782B2

(12) United States Patent
Thompson et al.

(10) Patent No.: US 6,849,782 B2
(45) Date of Patent: Feb. 1, 2005

(54) ARABIDOPSIS ANTISENSE DEOXYHYPUSINE SYNTHASE MOLECULE AND METHOD OF INHIBITING DEOXYHYPUSINE SYNTHASE EXPRESSION IN PLANTS

(75) Inventors: John E. Thompson, Waterloo (CA); Tzann-Wei Wang, Waterloo (CA); Dongen Lily Lu, Waterloo (CA)

(73) Assignee: Senesco, Inc., Princeton, NJ (US)

( * ) Notice: Subject to any disclaimer, the term of this patent is extended or adjusted under 35 U.S.C. 154(b) by 0 days.

(21) Appl. No.: 10/340,650

(22) Filed: Jan. 13, 2003

(65) Prior Publication Data

US 2003/0140377 A1 Jul. 24, 2003

Related U.S. Application Data

(62) Division of application No. 09/597,771, filed on Jun. 19, 2000, now Pat. No. 6,538,182, which is a continuation of application No. 09/348,675, filed on Jul. 6, 1999, now abandoned.

(51) Int. Cl.[7] .................... C12N 12/29; C12N 15/82; C12N 5/04; C12N 5/10

(52) U.S. Cl. .................. 800/290; 800/278; 800/287; 800/285; 800/298; 800/286; 536/23.1; 536/24.5; 435/468; 435/419; 435/320.1; 435/252.3

(58) Field of Search ...................... 800/290, 278, 800/287, 285, 298, 286; 536/23.1, 24.5; 435/468, 419, 320.1, 252.3

(56) References Cited

U.S. PATENT DOCUMENTS

| 5,328,999 A | 7/1994 | Bennett et al. |
| 5,763,742 A | 6/1998 | Morrison et al. ........... 800/200 |
| 5,767,364 A * | 6/1998 | de Silva et al. ............ 800/290 |
| 5,824,875 A | 10/1998 | Ranu |

OTHER PUBLICATIONS

Fourgoux–Nicol et al (1999, Plant Molecular Biology 40 : 857–872).*
Bryant (1989, Trends in Biotechnology 7(2):20–21).*
Martienssen (1998, PNAS 95:2021–2026).*
Rounsley (1997, NCBI GenBank, Accession B29697).*
Gan et al (1997, Plant Physiol. 113:313–319).*
Fourgoux–Nicol et al. (1999, Plant Molecular Biology 40; 857–872).
Ober et al., "Deoxyhypusine Synthase from Tobacco: cDNA Isolation, Characterization, and Bacterial Expression of an Enzyme with Extended Substrate Specificity" (1999, Journal of Biological Chemistry 274: 32040–32047).
Database EMBL 'Online! Bork et al., "Cloning and Expression of the CBL1 Gene Encoding Cystathionine–Beta–L–yase from *Arabidopsis thaliana*." Retrieved from EBI. Database accession No. AB004823 XP002227363.

Database EMBL 'Online! Pay et al., "Isolation and Sequence Determination of the Plant Homologue of the Eukaryotic Initiation Factor 4D cDNA from Alfalfa Medicago Sativa." Retrieved from EBI. Database accession No. X59441 XP002227364.
Dresselhaus et al, A Transcript Encoding Translation Initiation Factor eIF–5A is Stored in Unfertilized Egg Cells of Maize (1999, Plant Molecular Biology, 39: 1063–1071).
Ruhl et al., "Eukaryotic Initiation Factor 5A is a Cellular Target of the Human Immunodeficiency Virus Type 1 Rev Activation Domain Mediating Trans–Activation" (1993, Journal of Cell Biology, 123: 1309–1320).
Wang et al., "Isolation and Characterization of Senescence–induced cDNAs Encoding Deoxyhypusine Synthase and Eucaryotic Translation Initiation Factor 5A from Tomato" (2001, Journal of Biological Chemistry, 276: 17541–17549).
Wang et al., "Antisense Suppression of Deoxyhypusine Synthase Delays *Arabidopsis thaliana* Leaf Senescence and Confers Increased Tolerance to Environmental Stress," Joint Annual Meetings of the American Society of Plant Biologists and the Canadian Society of Plant Physiologists, Jul. 21–25, 2001 (Abstract #754).
Bowie et al., "Deciphering the Message in Protein Sequences: Tolerance to Amino Substitutions" (1990, Science, 247: 1306–1310).
Database EMBL Sequence Database 'Online!, Jun. 30, 1999 (Jun. 03, 1999) D'Ascenzo, M., et al.: "generation of ESTs from Pseudomonas resistant tomato", XP0021155343, accession No. A1775868.
Chamot D, et al: Differential Expression of Genes Encoding The Hypusine–Containing Translation Initiation Factor EIF–5A IN Tobacco Nucleic Acids Research, vol. 20, No. 4, 1992, pp. 665–669, XP002155337, ISSN: 0305–1048 cited in the application p. 668, left–hand column; figure 6.
Database EMBL Sequence Library 'Online!, Sep. 3, 1998 (Sep. 03, 1999), Nakamura, Y.:, XP002155344 cited in the application accession No. AB017060.1
Database EMBL Sequence Library Online! Jun. 30, 1999, D'Ascenzo, M., et al.: "generation of ESTs from Pseudomonas susceptible tomato" XP002155345, accession No. A1781299.
Database EMBL Sequence Database 'Online!, Jul. 1, 1997 In, J.G.: "untitied" XP002155346, accession No. AB004824.

(List continued on next page.)

*Primary Examiner*—Phuong T. Bui
*Assistant Examiner*—Stuart F. Baum
(74) *Attorney, Agent, or Firm*—Kenyon & Kenyon

(57) ABSTRACT

Regulation of expression of programmed cell death, including senescence, in plants is achieved by integration of a gene or gene fragment encoding senescence-induced deoxyhypusine synthase, senescence-induced eIF-5A or both into the plant genome in antisense orientation. Plant genes encoding senescence-induced deoxyhypusine synthase and senescence-induced eIF-5A are identified and the nucleotide sequences of each, alone and in combination are used to modify senescence in transgenic plants.

25 Claims, 41 Drawing Sheets

OTHER PUBLICATIONS

Kaiser Annette: "Cloning and expression of a cDNA encoding homospermidine synthase from *Senecio vulgaris* (Asteraceae) in *Eszcherichia coli*", Plant Journal, vol. 19, No. 2, Aug. 4, 1999, pp. 195–201, XP002155338, ISSN: 0960–7412 the whole document.
Ober Dietrich et al, "Homospermidine synthase, the first pathway–specific enzyme of pyrrolizidine alkaloid biosynthesis, evolved from deoxyhypucine synthase." Proceedings of the National Academy of Sciencws of the United States, vol. 96, No. 26, Dec. 21, 1999, pp. 14777–14782, XP002155341, Dec. 21, 1999, ISSN: 0027–8424, the whole document.
Alberts, et al., Molecular Biology of the Cell, 1989 2nd ed., Garland Publishing, Inc. New York, New York, pp. 195–196.
Bate et al., 1991, J. Exper. Botany, 42, 801–811.
Brach, M.A., Molec. 1993, Cell Biol., 13:4284–4290.
Buchanan–Wollaston, V., 1997, J. Exp. Botany, 48:181–199.
Chamot et al., 1992, Nuc. Acids Res., 20(4), 665–669.
Corpet, F.,1987, Nuc. Acids Res., 16:10881–10890.
De la pena et al.,1987, Injection into meristematic tissues of seedlings and plants, Nature, 325:274–276.
Evans et al., 1989, Annu. Rev. Plant Physiol. Plant Mol. Biol., 40, 235–269.
Fobert et al., 1994, Plant Journal, 6:567–577.
Fromm et al., 1986, Nature, Electroporation, 319:719.
Galston, et al., 1990, Plant Physiol., 94, 406–410.
Gan et al., 1997, Plant Physiol., 113:313.
Hensel et al., 1993, The Plant Cell, 5, 553–564.
Joe et al.,1995, J. Bio. Chem., 270:22386–22392.
Klein et al., 1988, Particle bombardment, BioTechnology, 6:559–563.
Merlo et al., 1998, The Plant Cell, 10:1603–1621.
Miki, et al., 1993, Procedures for Introducing Foreign DNA Into Plants, Methods in Plant Molecular Biology and Biotechnology, Eds. B.R. Glick and J.E. Thompson. CRC Press, pp. 67–88.
Molecular mechanisms in the Control of Gene expression, Nierlich, et al., eds., Acad. Press, N.Y., vol. V, 1976.
Morton et al., 1995, Molecular Breeding, 1:123–132.
Palauqui et al., 1996, Plant Physiol., 112:1447–1456.
Park et al.,1997, Biol. Signals, 6:115–123.
Paszkowski et al., 1984, Direct gene transfer into protoplasts or protoplast uptake, Embo J., 12:2717.
Ranu et al., 1979, Meth. Enzymol., 60:459–484.
Reich et al., 1986, Injection into protoplasts of cultured cells and tissues, BioTechnology, 4:1001–1004.
Thomas et al, 1992, J. Plant Physiol., 139, 403–12.
Wolff, et al., 1997, J. Bio. Chem., 272:15865–15871.
Wright, M., 1974, Plant, 120:63–69.
Bird et al., 1991, Biotech. And Engineer. Reviews, 9:207–227.
Chory et al., 1994, Plant Physiology, 104:339–347.
Kuipers et al., 1995, Mol. Gen. Genet., 246:745–755.
Sandler et al., 1988, Plant Molecular Biol., 11:301–310.
Smith et al., 1988, 334:724–726.
Chamot et al., *Differential expression of genes encoding the hypusine–containing translation initiation factor, elF–5A, in tobacco* (1992), Nucleic Acids Research, vol. 20, No. 4, pp. 665–669.
Park et al., *Hypusine: its post–translational formation in eukaryotic initiation factor 5A and its potential role in cellular regulation* (1993), BioFactors, vol. 4, No. 2, pp. 95–104.
Buchanan–Wollaston, V., *The molecular biology of leaf senescence* (1997), J. Exp. Bot., 307:181–199.
Cohen, *Growth of Studies on Hypusine in Biological Systems* (1997), Biological Signals, 6:110–114.
Park et al., *Hypusine Is Essential for Eukaryotic Cell Proliferation* (1997), Biological Signals, 6:115–123.
Tome et al., *Excess putrescine accumulation inhibits the formation of modified eukaryotic initiation factor 5A(elF–5A) and indues apoptosis* (1997), Biochem. J., 328:847–854.
Park et al.,Deoxyhypusine Synthase Activity Is Essential for Cell Viability in the Yeast *Saccharomyces cerevisiae* (1998) ,J. Biol. Chem., v. 273, No. 3, pp. 1677–1683.
Bevec et al., *Molecular characterization of a cDNA encoding functional human deoxyhypusine synthase and chromosomal mapping of the corresponding gene locus* (1996), FEBS Letters, 378:195–198.
Yan et al., *Molecular cloning and functional expression of human deoxyhypusine synthase cDNA based on expressed sequence tag information* (1996), Biochem. J., 315:429–434.
Joe et al., *Cloning and Expression of Human Deoxyhypusine Synthase cDNA*, (1995) Biol. Chem., vol. 270, No. 38, pp. 22386–22392.

* cited by examiner

Tomato Leaf DHS cDNA sequence

```
CGCAGAAACTCGCGGCGGCAGTCTTGTTCCGTACATAATCTTGGTCTGCAATAATGGAGAAGCTCTGAAGTACAGTATCATGGAC
                                                          M  G  E  A  L  K  Y  S  I  M  D

TCAGTAAGATCGGTAGTTTTCAAAGAATCCGAAAATCTAGAAGGTTCTTGCACTAAAATCGAGGGCTACGACTTCAATAAAGGCGT
 S  V  R  S  V  V  F  K  E  S  E  N  L  E  G  S  C  T  K  I  E  G  Y  D  F  N  K  G  V

TAACTATGCTGAGCTGATCAAGTCCATGGTTTCCACTGGTTTCCAAGCATCTAATCTTGGTGACGCCATTGCAATTGTTAATCAAA
 N  Y  A  E  L  I  K  S  M  V  S  T  G  F  Q  A  S  N  L  G  D  A  I  A  I  V  N  Q

TGCTAGATTGGAGGCTTTCACATGAGCTGCCCACGGAGGATTGCAGTGAAGAAGAGAGTGTTGCATACAGAGAGTCGGTAACC
 M  L  D  W  R  L  S  H  E  L  P  T  E  D  C  S  E  E  E  R  D  V  A  Y  R  E  S  V  T

TGCAAAATCTTCTTGGGGTTCACTTCAAACCTTGTTCTTCTGGTGTATTGAAGAGGATCTCATAAAGTGCCTGCACCTTGTTCAGCACCGGATGGT
 C  K  I  F  L  G  F  T  S  N  L  V  S  S  G  V  R  D  T  V  R  Y  L  V  Q  H  R  M  V

TGATGTTGTGGTTACTACAGCTGGTGGTATTGAAGAGGATCTCATAAAGTGCCTGCACCTTGTTCAGCACCGGATGGT
 D  V  V  V  T  T  A  G  G  I  E  E  D  L  I  K  C  L  A  P  T  Y  K  G  D  F  S  L

CTGGAGCTTCTCTACGATCGAAAGGATTGAACCGTATTGGTAACTTATTGGTTCCTAATGACAACTACTGCAAATTTGAGAATTGG
 P  G  A  S  L  R  S  K  G  L  N  R  I  G  N  L  L  V  P  N  D  N  Y  C  K  F  E  N  W

ATCATCCCAGTTTTTGACCAAATGTATGAGGAGCAGATTAATGAGAAGGTTCTATGGACACCATCTAAAGTCATTGCTCGTCTGGG
 I  I  P  V  F  D  Q  M  Y  E  E  Q  I  N  E  K  V  L  W  T  P  S  K  V  I  A  R  L  G
```

FIG. 1A

```
TAAGAAATTAATGATGAAACCTCATACTTGTATTGGGCTTACAAGAACCGGATTCCTGTCTTCTGTCCTGGCTTGACGGATGGAT
 K  E  I  N  D  E  T  S  Y  L  Y  W  A  Y  K  N  R  I  P  V  F  C  P  G  L  T  D  G

CACTTGGTGACATGCTATACTTCCATTCTTCAAAAAGGGTGATCCAGATAATCCAGATCTTAATCCTGGTCTAGTCATAGACATT
 S  L  G  D  M  L  Y  F  H  S  F  K  K  G  D  P  D  N  P  D  L  N  P  G  L  V  I  D  I

GTAGGAGATATTAGGGCCATGAATGGTGAAGCTGTCCATGCTGGTTTGAGGAAGACAGGAATGATTATACTGGGTGGAGGGCTGCC
 V  G  D  I  R  A  M  N  G  E  A  V  H  A  G  L  R  K  T  G  M  I  I  L  G  G  G  L  P

TAAGCACCATGTTTGCAATGCGCCAATATGATGAAGCTGTCTTCATTAACACCGCACAAGAGTTTGATGGTA
 K  H  H  V  C  N  A  N  M  M  R  N  G  A  D  F  A  V  F  I  N  T  A  Q  E  F  D  G

GTGACTCTGGTGCCCGTCCTGATGAAGCTGTATCATGGGGAAAAGATACGTGGTGGTGCCAAGACTGTGAAGGTGCATTGTGATGCA
 S  D  S  G  A  R  P  D  E  A  V  S  W  G  K  I  R  G  G  A  K  T  V  K  V  H  C  D  A

ACCATTGCATTTCCCATATTAGTAGCTGAGACATTTGCAGCTAAGAGTAAGGAATTCTCCCAGATAAGGTGCCAAGTTTGAACATT
 T  I  A  F  P  I  L  V  A  E  T  F  A  A  K  S  K  E  F  S  Q  I  R  C  Q  V

GAGGAAGCTGTCCTTCCGACCACACACATATGAATTGCTAGTTTTGAAGCCAACTTGCTAGTGTGCAGCACCATTATTCTGCAAAA
CTGACTAGAGAGCAGGTATATTCCTCTCTTCGAAAGTGAAGAGCTTAGAGACGACATCCTGTTGATGGTTCAAATTAATTATTTCTCCCCTTCACA
CCATGTTATTAGTTCTCTCCTCTCTTCGAAAGTGAAGAGCTTAGAGTGTTCATAGGTTTGAATTATGTTGGAGGTTGGTGATAACT
GACTAGTCCTCTTACCATATAGATGATGATCCCTTGTACTATGAGATTTGGGTGTGTGTTTGATACCAAGGAAAAATGTTTATTGG
AAAACAATTGGATTTTTAATTTATTTTCTTGTTTAAAAAAAAAAAAAAAAAAAAAAA
```

FIG. 1B

Arabidopsis DeoxyHypusine Synthase (DHS) Predicted Sequence

```
GAACTCCCAAAACCCTCTACTACTACACTTTCAGATCCAAGGAAATCAATTTTGTCATTCGAGCAACATGG
                                                                     M
AGGATGATCGTGTTTTCTCTTCGGTTCACTCAACAGTTTTCAAAGAATCCGAATCATTGGAAGGAAAGTGT
 E D D R V F S S V H S I V F K E S E S L E G K C
GATAAAATCGAAGGATACGATTTCAATCAAGGAGTAGATTACCCAAAGCTTATGCGATCCATGCTCACCAC
 D K I E G Y D F N Q G V D Y P K L M R S M L T T
CGGATTTCAAGCCTCGAATCTCGGCGAAGCTATTGATGTCGTCAATCAAATGGTTCGTTTCTCGAATTCAT
 G F Q A S N L G E A I D V V N Q M
CAAAAATAAAAATTCCTTCTTTTTGTTTTCCTTTGTTTTGGGTGAATTAGTAATGACAAACAGTTTGAATT
                                                                 L E F
TGTATTGAAGCTAGATTGGAGACTGGCTGATGAAACTACAGTAGCTGAAGACTGTAGTGAAGAGGAGAAGA
 V L K L D W R L A D E T V A E D C S E E K
ATCCATCGTTTAGAGAGTCTGTCAAGTGTAAAATCTTTCTAGGTTTCACTTCAAATCTTGTTTCATCTGGT
 N P S F R E S V K C K I F L G F T S N L V S S G
GTTAGAGATACTATTCGTTATCTTGTTCAGCATCATATGGTTTGTGATTTTTGCTTTATCACCCTGCTTTT
 V R D T I R Y L V Q H H M
TTATAGATGTTAAAATTTTCGAGCTTTAGTTTTGATTTCAATGGTTTTTCTGCAGGTTGATGTTATAGTCA
                                                        V D V I V
CGACAACTGGTGGTGTTGAGGAAGATCTCATAAAATGCCTTGCACCTACATTTAAAGGTGATTTCTCTCTA
 T T T G G V E E D L I K C L A P T F K G D F S I
CCTGGAGCTTATTTAAGGTCAAAGGGGATTGAACCGAATTGGGAATTTGCTGGTTCCTAATGATAACTACTG
 P G A Y L R S K G L N R I G N L L V P N D N Y C
CAAGTTTGAGGATTGGATCATTCCCATCTTTGACGAGATGTTGAAGGAACAGAAAGAACAGGTATTGCTTT
 K F E D W I I P I F D E M L K E Q K E E
ATCTTTCCTTTTTATATGATTTGAGATGATTCTGTTTGTGCGTCACTAGTGGAGATAGATTCTGATTCCTC
TCTTGCATCATTGACTTCGTTGGTGAATCCTTCTTTCTCTGGTTTTTCCTTGTAGAATGTGTTGTGGACTC
                                                        N V L W I
CTTCTAAACTGTTAGCACGGCTGGGAAAAGAAATCAACAATGAGAGTTCATACCTTTATTGGGCATACAAG
 P S K L L A R L G K E I N N E S S Y L Y W A Y K
GTATCCAAAATTTTAACCTTTTTAGTTTTTTAATCATCCTGTGAGGAACTCGGGGATTTAAATTTTCCGCT
TCTTGTGGTGTTTGTAGATGAATATTCCAGTATTCTGCCCAGGGTTAACAGATGGCTCTCTTGGGGATATG
                     M N I P V F C P G L T D G S L G D M
CTGTATTTTCACTCTTTTCGTACCTCTGGCCTCATCATCGATGTAGTACAAGGTACTTCTTTTACTCAATA
 L Y F H S F R T S G L I I D V V Q
AGTCAGTGTGATAAATATTCCTGCTACATCTAGTGCAGGAATATTGTAACTAGTAGTGCATTGTAGCTTTT
CCAATTCAGCAACGGACTTTACTGTAAGTTGATATCTAAAGGTTCAAACGGGAGCTAGGAGAATAGCCATAG
GGGCATTCTGATTTAGGTTTGGGGCACTGGGTTAAGAGTTAGAGAATAATAATCTTGTTAGTTGTTTATCA
AACTCTTTGATGGTTAGTCTCTTGGTAATTTGAATTTTATCACAGTGTTTATGGTCTTTGAACCAGTTAAT
GTTTTATGAACAGATATCAGAGCTATGAACGGCGAAGCTGTCCATGCAAATCCTAAAAAGACAGGGATGAT
                        D I R A M N G F A V H A N P K K T G M I
AATCCTTGGAGGGGGCTTGCCAAAGCACCACATATGTAATGCCAATATGATGCGCAATGGTGCAGATTACG
  I L G G G L P K H H I C N A N M M R N G A D Y
CTGTATTTATAAACACCGGGCAAGAATTTGATGGGAGCGACTCGGGTGCACGCCCTGATGAAGCCGTGTCT
 A V F I N T G Q E F D G S D S G A R P D E A V S
TGGGGTAAAAATTAGGGGTTCTGCTAAAACCGTTAAGGTCTGCTTTTTAATTTCTTCACATCCTAATTTATA
 W G K I R G S A K T V K V C F L I S S H P N L Y
TCTCACTCAGTGGTTTTGAGTACATATTTAATATTGGATCATTCTTGCAGGTATACTGTGATGCTACCATA
  L T Q W F
GCCTTCCCATTGTTGGTTGCAGAAACATTTGCCACAAAGAGAGACCAAACCTGTGAGTCTAAGACTTAAGA
ACTGACTGGTCGTTTTGGCCATGGATTCTTAAAGATCGTTGCTTTTTGATTTTACACTGGAGTGACCATAT
AACACTCCACATTGATGTGGCTGTGACGCGAATTGTCTTCTTGCGAATTGTACTTTAGTTTCTCTCAACCT
AAAATGATTTGCAGATTGTGTTTTCGTTTAAAAACACAAGAGTCTTGTAGTCAATAATCCTTTGCCTTATAA
AATTATTCAGTTCCAACAACACATTGTGATTCTGTGACAAGTCTCCCGTTGCCTATGTTCACTTCTCTGCG
```

FIG.2A

MEDDRVFSSVHSTVFKESESLEGKCDKIEGYDFNQGVDYPKLMRSMLTTGFQASNLGEAIDVVNQMFEFVLKLDWRLADETTV
AEDCSEEEKNPSFRESVKCKIFLGFTSNLVSSGVRDTIRYLVQHHMVDIVTTTGGVEEDLIKCLAPTFKGDFSLPGAYLRSK
GLNRIGNLLVPNDNYCKFEDWIIPIFDEMLKEQKEENVLWTPSKLLARLGKEINNESSYLYWAYKMNIPVFCPGLTDGSLGDM
LYFHSFRTSGLIIDVVQDIRAMNGEAVHANPKKTGMIILGGGLPKHHICNANMMRNGADYAVFINTGQEFDGSDSGARPDEAV
SWGKIRGSAKTVKVCFLISSHPNLYLTQWF

FIG.2B

GGTGGTGTTGAGGAAGATCTCATAAAATGCCTTGCACCTACATTTAAAGGTGATTTCTCTCTACCTGGAGCTTATTTAAG
GTCAAAGGGATTGAACCGAATTGTTGAAGGAACAGAAGAGAAGAATGTGTTGTGGACTCCTTCTAAACTGTTAGCACGCTGGGAAAA
TCTTTGACGAGAGATGTTGAAGGAACAGAAGAGAAGAATGTGTTGTGGACTCCTTCTAAACTGTTAGCACGCTGGGAAAA
GAAATCAACAATGAGAGTTCATACCTTTATTGGGCATACAAGATGAATATTCCAGTATCATCGATGAGTAGCAGATGG
CTCTCTTAGGGATATGCTGTCCATGCAAATCCTAAAAAGACAGGATGATAATCCTTGGAGGGGCTTGCCAAGCACCACATA
TGAACGGCGAAGCTGTCCATATGCGCAATGGTGCAGATTACGCTGTATTTATAAACACCGGCAAGAATTTGATGGGAGCGACTC
GGGTGCACGCCCTGATGAAGC

FIG.2C

GGVEEDLIKCLAPTFKGDFSLPGAYLRSKGLNRIGNLLVPNDNYCKFEDWIIPIFDEMLKEQKEENVLWTPSKLLARLGKEIN
NESSYLYWAYKMNIPVFCPGLTDGSLRDMLYFHSFRTSGLIIDVVQDIRAMNGEAVHANPKKTGMIILGGGLPKHHICNANMM
RNGADYAVFINTGQEFDGSDSGARPDE

FIG.2D

Multiple DHS Sequence Alignments of
Human, Arabidopsis, Tomato, Yeast, Neurospora (Fungi), and
Methanococcus (Archaeobacteria)

FIG.3

Northern analysis of DHS on tomato flowers
RNA — Bud, Blossom and Senescence
Northern
FIG.6

NORTHERN ANALYSIS OF DHS
ON DEVELOPMENTAL STAGES OF
TOMATO FRUIT

BREAKER   PINK   RIPE (RED)

NORTHERN BLOT

Canation DHS cDNA Sequence

```
GTCATTACAATGCATAGGATCATTGCACATGCTACCTTCCTCATTGCACTTGAGCTTGCCATA
CTTTTGTTTTTGACGTTTGATAATAATACTATGAAAATATTATGTTTTTTCTTTTGTGTGTTG
GTGTTTTTGAAGTTGTTTTTGATAAGCAGAACCCAGTTGTTTTACACTTTTACCATTGAACTA
CTGCAATTCTAAAACTTTGTTTACATTTTAATTCCATCAAAGATTGAGTTCAGCATAGGAAAA
AGGATGGAGGATGCTAATCATGATAGTGTGGCATCTGCGCACTCTGCAGCATTCAAAAAGTCG
       M  E  D  A  N  H  D  S  V  A  S  A  H  S  A  A  F  K  K  S
GAGAATTTAGAGGGGAAAAGCGTTAAGATTGAGGGTTATGATTTTAATCAAGGTGTAAACTAT
  E  N  L  E  G  K  S  V  K  I  E  G  Y  D  F  N  Q  G  V  N  Y
TCCAAACTCTTGCAATCTTTCGCTTCTAATGGGTTTCAAGCCTCGAATCTTGGAGATGCCATT
  S  K  L  L  Q  S  F  A  S  N  G  F  Q  A  S  N  L  G  D  A  I
GAAGTAGTTAATCATATGCTAGATTGGAGTCTGGCAGATGAGGCACCTGTGGACGATTGTAGC
  E  V  V  N  H  M  L  D  W  S  L  A  D  E  A  P  V  D  D  C  S
GAGGAAGAGAGGGATCCTAAATTCAGAGAATCTGTGAAGTGCAAAGTGTTCTTGGGCTTTACT
  E  E  E  R  D  P  K  F  R  E  S  V  K  C  K  V  F  L  G  F  T
TCAAATCTTATTTCCTCTGGTGTTCGTGACACAATTCGGTATCTCGTGCAACATCATATGGTT
  S  N  L  I  S  S  G  V  R  D  T  I  R  Y  L  V  Q  H  M  V
GACGTGATAGTAACGACAACCGGAGGTATAGAAGAAGATCTAATAAAAGGAAGATCCATCAAG
  D  V  I  V  T  T  T  G  G  I  E  E  D  L  I  K  G  R  S  I  K
TGCCTTGCACCCACTTTCAAAGGCGATTTTGCCTTACCAGGAGCTCAATTACGCTCCAAAGGG
  C  L  A  P  T  F  K  G  D  F  A  L  P  G  A  Q  L  R  S  K  G
TTGAATCGAATTGGTAATCTGTTGGTTCCGAATGATAACTACTGTAAATTTGAGGATTGGATC
  L  N  R  I  G  N  L  L  V  P  N  D  N  Y  C  K  F  E  D  W  I
ATTCCAATTTTAGATAAGATGTTGGAAGAGCAAATTTCAGAGAAAATCTTATGGACACCATCG
  I  P  I  L  D  K  M  L  E  E  Q  I  S  E  K  I  L  W  T  P  S
AAGTTGATTGGTCGATTAGGAAGAGAAATAAACGATGAGAGTTCATACCTTTACTGGGCCTTC
  K  L  I  G  R  L  G  R  E  I  N  D  E  S  S  Y  L  Y  W  A  F
AAGAACAATATTCCAGTATTTTGCCCAGGTTTAACAGACGGCTCACTCGGAGACATGCTATAT
  K  N  N  I  P  V  F  C  P  G  L  T  D  G  S  L  G  D  M  L  Y
TTTCATTCTTTTCGCAATCCGGGTTTAATCGTCGATGTTGTGCAAGATATAAGAGCAGTAAAT
  F  H  S  F  R  N  P  G  L  I  V  D  V  V  Q  D  I  R  A  V  N
GGCGAGGCTGTGCACGCAGCGCCTAGGAAAACAGGCATGATTATACTCGGTGGAGGGTTGCCT
  G  E  A  V  H  A  A  P  R  K  T  G  M  I  I  L  G  G  G  L  P
AAGCACCACATCTGCAACGCAAACATGATGAGAAATGGCGCCGATTATGCTGTTTTCATCAAC
  K  H  H  I  C  N  A  N  M  M  R  N  G  A  D  Y  A  V  F  I  N
ACTGCCGAAGAGTTTGACGGCAGTGATTCTGGTGCTCGCCCCGATGAGGCTATTTCATGGGGC
  T  A  E  E  F  D  G  S  D  S  G  A  R  P  D  E  A  I  S  W  G
AAAATTAGCGGATCTGCTAAGACTGTGAAGGTGCATTGTGATGCCACGATAGCTTTCCCTCTA
  K  I  S  G  S  A  K  T  V  K  V  H  C  D  A  T  I  A  F  P  L
CTAGTCGCTGAGACATTTGCAGCAAAAAGAGAAAAAGAGAGGAAGAGCTGTTAAAACTTTTTT
  L  V  A  E  T  F  A  A  K  R  E  K  E  R  K  S  C
GATTGTTGAAAAATCTGTGTTATACAAGTCTCGAAATGCATTTTAGTAATTGACTTGATCTTA
TCATTTCAATGTGTTATCTTTGAAAATGTTGGTAATGAAACATCTCACCTCTTCTATACAACA
TTGTTGATCCATTGTACTCCGTATCTTGTAATTTTGGAAAAAAAAAACCGTCTATTGTTACGA
GAGAGTACATTTTTGAGGTAAAAATATAGGATTTTTTGTGCGATGCAAATGCTGGTTATTCCCT
TGAAAAAAAAAAAAAAAAAAAAA
```
(1384 bps, not include Poly A tail and 5'end nocoding region.
373 Amino Acid.)

FIG.10

Northern Analysis of Canation Petal *(In Situ)* DHS

Tomato eif5A

```
AAAGAATCCTAGAGAGAGAAAGGGAATCCTAGAGAGAGAAGCATGTCGGACGAAGAACAC
                                              M  S  D  E  E  H
CATTTTGAGTCAAAGGCAGATGCTGGTGCCTCAAAAACTTTCCCACAGCAAGCTGGAACC
 H  F  E  S  K  A  D  A  G  A  S  K  T  F  P  Q  Q  A  G  T
ATCCGTAAGAATGGTTACATCGTTATCAAAGGCCGTCCCTGCAAGGTTGTTGAGGTCTCC
 I  R  K  N  G  Y  I  V  I  K  G  R  P  C  K  V  V  E  V  S
ACTTCAAAAACTGGAAAACACGGACATGCTAAATGTCACTTTGTGGCAATTGACATTTTC
 T  S  K  T  G  K  H  G  H  A  K  C  H  F  V  A  I  D  I  F
AATGGAAAGAAACTGGAAGATATCGTTCCGTCCTCCCACAATTGTGATGTGCCACATGTT
 N  G  K  K  L  E  D  I  V  P  S  S  H  N  C  D  V  P  H  V
AACCGTACCGACTATCAGCTGATTGATATCTCTGAAGATGGTTTTGTCTCACTTCTTACT
 N  R  T  D  Y  Q  L  I  D  I  S  E  D  G  F  V  S  L  L  T
GAAAGTGGAAACACCAAGGATGACCTCAGGCTTCCCACCGATGAAAATCTGCTGAAGCAG
 E  S  G  N  T  K  D  D  L  R  L  P  T  D  E  N  L  L  K  Q
GTTAAAGATGGGTTCCAGGAAGGAAAGGATCTTGTGGTGTCTGTTATGTCTGCGATGGGC
 V  K  D  G  F  Q  E  G  K  D  L  V  V  S  V  M  S  A  M  G
GAAGAGCAGATTAACGCCGTTAAGGATGTTGGTACCAAGAATTAGTTATGTCATGGCAGC
 E  E  Q  I  N  A  V  K  D  V  G  T  K  N
ATAATCACTGCCAAAGCTTTAAGACATTATCATATCCTAATGTGGTACTTTGATATCACT
AGATTATAAACTGTGTTATTTGCACTGTTCAAAACAAAAGAAAGAAAACTGCTGTTATGG
CTAGAGAAAGTATTGGCTTTGAGCTTTTGACAGCACAGTTGAACTATGTGAAAATTCTAC
TTTTTTTTTTTTGGGTAAAATACTGCTCGTTTAATGTTTTGCAAAAAAAAAAAAAAAAAA
```

*764 bps. not including Poly(A) tail; 160 amino acids*

FIG. 13

Carnation-F5A

```
CTCTTTTACATCAATCGAAAAAAAATTAGGGTTCTTATTTTAGAGTGAGA

GGCGAAAAATCGAACGATGTCGGACGACGATCACCATTTCGAGTCATCGG
                  M  S  D  D  D  H  H  F  E  S  S  A
CCGACGCCGGAGCATCCAAGACTTACCCTCAACAAGCTGGTACAATCCGC
  D  A  G  A  S  K  T  Y  P  Q  Q  A  G  T  I  R
AAGAGCGGTCACATCGTCATCAAAAATCGcCCtTGCAAGGtGGTTGAGGT
  K  S  G  H  I  V  I  K  N  R  P  C  K  V  V  E  V
TTCTACCTCCAAGACTGGCAAGCACGGTCATGCCAAATGTCACTTTGTTG
  S  T  S  K  T  G  K  H  G  H  A  K  C  H  F  V  A
CCATTGACATTTTCAACGGCAAGAAGCTGGAAGATATTGTCCCCTCATCC
  I  D  I  F  N  G  K  K  L  E  D  I  V  P  S  S
CACAATTGTGATGTTCCACATGTCAACCGTGTCGACTACCAGCTGCTTGA
  H  N  C  D  V  P  H  V  N  R  V  D  Y  Q  L  L  D
TATCACTGAAGATGGCTTTCTTAGTCTGCTGACTGACAGTGGTGACACCA
  I  T  E  D  G  F  V  S  L  L  T  D  S  G  D  T  K
AGGATGATCTGAAGCTTCCTGCTGATGAGGCCCTTGTGAAGCAGATGAAG
  D  D  L  K  L  P  A  D  E  A  L  V  K  Q  M  K
GAGGGATTTGAGGCGGGGAAAGACTTGATTCTGTCAGTCATGTGTGCAAT
  E  G  F  E  A  G  K  D  L  I  L  S  V  M  C  A  M
GGGAGAAGAGCAGATCTGCGCCGTCAAGGACGTTAGTGGTGGCAAGTAGA
  G  E  E  Q  I  C  A  V  K  D  V  S  G  G  K
AGCTTTTGATGAATCCAATACTACGCGGTGCAGTTGAAGCAATAGTAATC
TCGAGAACATTCTGAACCTTATATGTTGAATTGATGGTGCTTAGTTTGTT
TTGGAAATCTCTTTGCAATTAAGTTGTACCAAATCAATGGATGTAATGTC
TTGAATTTGTTTTATTTTTGTTTTGATGTTTGCTGtGATTGCATTATGCA
TTGTTATGAGTTATGACCTGTTATAACACAAGGTTTTGGTAAAAAAAAAA
AAAAAAAAAAA
```

*790 bps. 160 amino acids*

FIG.14

Arabidopsis F5A

```
CTGTTACCAAAAAATCTGTACCGCAAAATCCTCGTCGAAGCTCGCTGCTGCAACCATGTC
                                                           M  S
CGACGAGGAGCATCACTTTGAGTCCAGTGACGCCGGAGCGTCCAAAACCTACCCTCAACA
 D  E  E  H  H  F  E  S  S  D  A  G  A  S  K  T  Y  P  Q  Q
AGCTGGAACCATCCGTAAGAATGGTTACATCGTCATCAAAAATCGTCCCTGCAAGGTTGT
 A  G  T  I  R  K  N  G  Y  I  V  I  K  N  R  P  C  K  V  V
TGAGGTTTCAACCTCGAAGACTGGCAAGCATGGTCATGCTAAATGTCATTTTGTAGCTAT
 E  V  S  T  S  K  T  G  K  H  G  H  A  K  C  H  F  V  A  I
TGATATCTTCACCAGCAAGAAACTCGAAGATATTGTTCCTTCTTCCCACAATTGTGATGT
 D  I  F  T  S  K  K  L  E  D  I  V  P  S  S  H  N  C  D  V
TCCTCATGTCAACCGTACTGATTATCAGCTGATTGACATTTCTGAAGATGGATATGTCAG
 P  H  V  N  R  T  D  Y  Q  L  I  D  I  S  E  D  G  Y  V  S
TTTGTTGACTGATAACGGTAGTACCAAGGATGACCTTAAGCTCCCTAATGATGACACTCT
 L  L  T  D  N  G  S  T  K  D  D  L  K  L  P  N  D  D  T  L
GCTCCAACAGATCAAGAGTGGGTTTGATGATGGAAAAGATCTAGTGGTGAGTGTAATGTC
 L  Q  Q  I  K  S  G  F  D  D  G  K  D  L  V  V  S  V  M  S
AGCTATGGGAGAGGAACAGATCAATGCTCTTAAGGACATCGGTCCCAAGTGAGACTAACA
 A  M  G  E  E  Q  I  N  A  L  K  D  I  G  P  K
AAGCCTCCCCTTTGTTATGAGATTCTTCTTCTTCTGTAGGCTTCCATTACTCGTCGGAGA
TTATCTTGTTTTTGGGTTACTCCTATTTTGGATATTTAAACTTTTGTTAATAATGCCATC
TTCTTCAACCTTTTCCTTCTAGATGGTTTTTATACTTCTTCT
```

*754 bps, not including Poly(A) tail; 158 amino acids*

FIG. 15

Arabidopsis 3'-end DHS for antisense

Nucleotide and derived amino acid sequence
TGCACGCCCTGATGAAGCTGTGTCTTGGGGTAAAATTAGGGGTTCTGCTAAAACCGTTAAGGTCTGCTTTT
  A  R  P  D  E  A  V  S  W  G  K  I  R  G  S  A  K  T  V  K  V  C  F TAATTTCTTCACATCCTAATTTATATCTCACTCAGTGGTTTTGAGTACATATTTAATATTGGATCATTCTT
 L  I  S  S  H  P  N  L  Y  L  T  Q  W  F GCAGGTATACTGTGATGCTACCATAGCCTTCCCATTGTTGGTTGCAGAAACATTTGCCACAAAGAGAGACC
AAACCTGTGAGTCTAAGACTTAAGAACTGACTGGTCGTTTTGGCCATGGATTCTTAAAGATCGTTGCTTTT
TGATTTTACACTGGAGTGACCATATAACACTCCACATTGATGTGGCTGTGACGCGAATTGTCTTCTTGCGA
ATTGTACTTTAGTTTCTCTCAACCTAAAATGATTTGCAGATTGTGTTTTCGTTTAAAACACAAGAGTCTTG
TAGTCAATAATCCTTTGCCTTATAAAATTATTCAGTTCCAACAAAAAAAAAAAAAAAA

- - - - - - - - - - - - - - - - - - - - - - - - - - - - - - - - - - - - - - - - - - -

Nucleotide sequence
TGCACGCCCTGATGAAGCTGTGTCTTGGGGTAAAATTAGGGGTTCTGCTAAAACCGTTAAGGTCTGCTTTT
TAATTTCTTCACATCCTAATTTATATCTCACTCAGTGGTTTTGAGTACATATTTAATATTGGATCATTCTT
GCAGGTATACTGTGATGCTACCATAGCCTTCCCATTGTTGGTTGCAGAAACATTTGCCACAAAGAGAGACC
AAACCTGTGAGTCTAAGACTTAAGAACTGACTGGTCGTTTTGGCCATGGATTCTTAAAGATCGTTGCTTTT
TGATTTTACACTGGAGTGACCATATAACACTCCACATTGATGTGGCTGTGACGCGAATTGTCTTCTTGCGA
ATTGTACTTTAGTTTCTCTCAACCTAAAATGATTTGCAGATTGTGTTTTCGTTTAAAACACAAGAGTCTTG
TAGTCAATAATCCTTTGCCTTATAAAATTATTCAGTTCCAACAAAAAAAAAAAAAAAA

ARPDEAVSWGKIRGSAKTVKVCFLISSHPNLYLTQWF

FIG. 36

Tomato 3'-end-Deoxyhupsine synthase used for antisense

Nucleotide and derived amino acid sequence
GGTGCTCGTCCTGATGAAGCTGTGTATCATGGGGAAAGATACGTGGTGGTGCCAAGACTGTGAAGGTGCATTGTGATGCAAC
 G  A  R  P  D  E  A  V  S  W  G  K  I  R  G  G  A  K  T  V  K  V  H  C  D  A  T CATTGCATTTCCCATATTAGTAGCTGAGACATTTGCAGTGCAAGAGTAAGGAATTCTCCCAGATAAGGTGCCAAGTTTGAA
 I  A  F  P  I  L  V  A  E  T  F  A  A  K  S  K  E  F  S  Q  I  R  C  Q  V CATTGAGGAAGCTGTCCTTCCGACCACACATATGAATTGCTAGCTTTTGAAGCCAACTTGCTAGTGTGCAGCACCATTTA
TTCTGCAAAACTGACTAGAGAGCAGGGTATATTCCTCTACCCGAGTTAGACGACATCCTGTATGGTTCAAATTAATTAT
TTTTCTCCCCTTCACACCATGTTATTAGTTCTCTTCCTCTTCGAAAGTGAAGAGCTTAGATGTTCATAGGTTTTGAATT
ATGTTGGAGGTTGGTGATAACTGACTAGTCCTCTTGATAACTGACTAGTCCTCTTACCATATAGATAGAATGTATCC
TTGATACCAAGGAAAAATGTTTATTTGGAAAACAATTGNTTAAAAAAAATTGNTTAAAAAAAAAAA

.............

Nucleotide sequence
GGTGCTCGTCCTGATGAAGCTGTATCATGGGGAAAGATACGTGGTGGTGCCAAGACTGTGAAGGTGCATTGTGATGCAAC
CATTGCATTTCCCATATTAGTAGCTGAGACATTAGTAGCTGAGACATTTGCAGTGCAAGAGTAAGGAATTC TCCCAGATAAGGTGCCAAGTTTGAACATTGAGGAAGCTGTCCTTCCGACCACACATATGAATTGCTAGCTTTTGAAGCCA
ACTTGCTAGTGTGCAGCACCATTTATTCTGCAAAACTGACTAGAGAGCAGGGTATATTCCTCTACCCGAGTTAGACGAC
ATCCTGTATGGTTCAAATTAATTATTTTTCTCCCCTTCACACCATGTTATTAGTTCTCTTCCTCTTCGAAAGTGAAGAG
CTTAGATGTTCATAGGTTTTGAATTATGTTGGAGGTTGGTGATAACTGACTAGTCCTCTTACCATATAGATAGAATGTATCC
TTGTACTATGAGATTTGGGTGTGTTTGATACCAAGGAAAAATGTTTATTTGGAAAACAATTGTTATTTAATTTAAAAA
AAATTGNTTAAAAAAAAAAA

FIG.37

600 bp Arabidopsis Deoxyhypusine Synthase Probe

Primer1 (underlined)

<u>GGTGGTGTTGAGGAAGATC</u>TCATAAAATGCCTTGCACCTACATTTAAAGGTGATTTCTCTCTACCTGGAGC
TTATTTAAG
G  G  V  E  E  D  L  I  K  C  L  A  P  T  F  K  G  D  F  S  L  P  G  A
              Y  L  R

GTCAAAGGGATTGAACCGAATTGGGAATTTGCTGGTTCCTAATGATAACTACTGCAAGTTTGAGGATTGGA
TCATTCCCA
S  K  G  L  N  R  I  G  N  L  L  V  P  N  D  N  Y  C  K  F  E  D  W  I
                  I  P

TCTTTGACGAGATGTTGAAGGAACAGAAAGAAGAGAATGTGTTGTGGACTCCTTCTAAACTGTTAGCACGG
CTGGGAAAA
I  F  D  E  M  L  K  E  Q  K  E  E  N  V  L  W  T  P  S  K  L  L  A  R
                  L  G  K

GAAATCAACAATGAGAGTTCATACCTTTATTGGGCATACAAGATGAATATTCCAGTATTCTGCCCAGGGTT
AACAGATGG
E  I  N  N  E  S  S  Y  L  Y  W  A  Y  K  M  N  I  P  V  F  C  F  G  L
                  T  D  G

CTCTCTTAGGGATATGCTGTATTTTCACTCTTTTCGTACCTCTGGCCTCATCATCGATGTAGTACAAGATA
TCAGAGCTA

S  L  R  D  M  L  Y  F  H  S  F  R  T  S  G  L  I  I  D  V  V  Q  D  I
                R  A

TGAACGGCGAAGCTGTCCATGCAAATCCTAAAAAGACAGGGATGATAATCCTTGGAGGGGGCTTGCCAAAG
CACCACATA
M  N  G  E  A  V  H  A  N  P  K  K  T  G  M  I  I  L  G  G  G  L  P  K
                    H  H  I

TGTAATGCCAATATGATGCGCAATGGTGCAGATTACGCTGTATTTATAAACACCGGGCAAGAATTTGATGG
GAGCGACTC
C  N  A  N  M  M  R  N  G  A  D  Y  A  V  F  I  N  T  G  Q  E  F  D  G
              S  D  S
<u>GGGTGCACGCCCTGATGAAGC</u>
G  A  R  P  D  E
Primer 2 (underlined)

FIG.38

483 bp Carnation Deoxyhypusine Synthase Probe

```
GAAGATCCATCAAGTGCCTTGCACCCACTTTCAAAGGCGATTTTGCCTTACCAGGAGCTCAATTACGCTCC
                                AAAGGGT
 R  R  S  I  K  C  L  A  P  T  F  K  G  D  F  A  L  P  G  A  Q  L  R  S
                               K  G

TGAATCGAATTGGTAATCTGTTGGTTCCGAATGATAACTACTGTAAATTTGAGGATTGGATCATTCCAATT
                                TTAGATA
 L  N  R  I  G  N  L  L  V  P  N  D  N  Y  C  K  F  E  D  W  I  I  P  I
                               L  D

AGATGTTGGAAGAGCAAATTTCAGAGAAAATCTTATGGACACCATCGAAGTTGATTGGTCGATTAGGAAGA
                                GAAATAA
 K  M  L  E  E  Q  I  S  E  K  I  L  W  T  P  S  K  L  I  G  R  L  G  R
                               E  I

ACGATGAGAGTTCATACCTTTACTGGGCCTTCAAGAACAATATTCCAGTATTTTGCCCAGGTTTAACAGAC
                                GGCTCAC
 N  D  E  S  S  Y  L  Y  W  A  F  K  N  N  I  P  V  F  C  P  G  L  T  D
                               G  S

TCGGAGACATGCTATATTTTCATTCTTTTCGCAATCCGGGTTTAATCATCGATGTTGTGCAAGATATAAGA
                                GCAGTAA
 L  G  D  M  L  Y  F  H  S  F  R  N  P  G  L  I  I  D  V  V  Q  D  I  R
                               A  V

ATGGCGAGGCTGTGCACGCAGCGCCTAGGAAAACAGGCATGATTATACTCGGTGGAGGGTTGCCTAAGCAC
                                CACATCT
 N  G  E  A  V  H  A  A  P  R  K  T  G  M  I  I  L  G  G  G  L  P  K  H
                               H  I

GCAACGCAAACATGATGAGAAATGGCGCCGATTATGCTGTTTTCATCAACACCG
              C  N  A  N  M  M  R  N  G  A  D  Y  A  V  F  I  N  T
```

A full-length cDNA clone was obtained by screening a carnation senescing petal cDNA library with this probe.

FIG.39

SEQUENCE LISTING

<160> NUMBER OF SEQ ID NOS: 35

<210> SEQ ID NO 1
<211> LENGTH: 1609
<212> TYPE: DNA
<213> ORGANISM: Lycopersicon sp.
<220> FEATURE:
<221> NAME/KEY: CDS
<222> LOCATION: (54..1196)
<220> FEATURE:
<223> OTHER INFORMATION: DHS

<400> SEQUENCE: 1

```
cgcagaaact cgcggcggca gtcttgttcc ctacataatc ttggtctgca ata atg          56
                                                          Met
                                                            1 gga gaa gct ctg aag tac agt atc atg gac tca gta aga tcg gta gtt        104
Gly Glu Ala Leu Lys Tyr Ser Ile Met Asp Ser Val Arg Ser Val Val
              5                  10                  15 ttc aaa gaa tcc gaa aat cta gaa ggt tct tgc act aaa atc gag ggc        152
Phe Lys Glu Ser Glu Asn Leu Glu Gly Ser Cys Thr Lys Ile Glu Gly
         20                  25                  30 tac gac ttc aat aaa ggc gtt aac tat gct gag ctg atc aag tcc atg        200
Tyr Asp Phe Asn Lys Gly Val Asn Tyr Ala Glu Leu Ile Lys Ser Met
     35                  40                  45 gtt tcc act ggt ttc caa gca tct aat ctt ggt gac gcc att gca att        248
Val Ser Thr Gly Phe Gln Ala Ser Asn Leu Gly Asp Ala Ile Ala Ile
 50                  55                  60                  65 gtt aat caa atg cta gat tgg agg ctt tca cat gag ctg ccc acg gag        296
Val Asn Gln Met Leu Asp Trp Arg Leu Ser His Glu Leu Pro Thr Glu
                 70                  75                  80 gat tgc agt gaa gaa gaa aga gat gtt gca tac aga gag tcg gta acc        344
Asp Cys Ser Glu Glu Glu Arg Asp Val Ala Tyr Arg Glu Ser Val Thr
```

-continued

```
                        85                    90                    95
tgc aaa atc ttc ttg ggg ttc act tca aac ctt gtt tct tct ggt gtt         392
Cys Lys Ile Phe Leu Gly Phe Thr Ser Asn Leu Val Ser Ser Gly Val
        100                 105                 110 aga gac act gtc cgc tac ctt gtt cag cac cgg atg gtt gat gtt gtg         440
Arg Asp Thr Val Arg Tyr Leu Val Gln His Arg Met Val Asp Val Val
115                 120                 125 gtt act aca gct ggt ggt att gaa gag gat ctc ata aag tgc ctc gca         488
Val Thr Thr Ala Gly Gly Ile Glu Glu Asp Leu Ile Lys Cys Leu Ala
130                 135                 140                 145 cca acc tac aag ggg gac ttc tct tta cct gga gct tct cta cga tcg         536
Pro Thr Tyr Lys Gly Asp Phe Ser Leu Pro Gly Ala Ser Leu Arg Ser
                150                 155                 160 aaa gga ttg aac cgt att ggt aac tta ttg gtt cct aat gac aac tac         584
Lys Gly Leu Asn Arg Ile Gly Asn Leu Leu Val Pro Asn Asp Asn Tyr
            165                 170                 175 tgc aaa ttt gag aat tgg atc atc cca gtt ttt gac caa atg tat gag         632
Cys Lys Phe Glu Asn Trp Ile Ile Pro Val Phe Asp Gln Met Tyr Glu
        180                 185                 190 gag cag att aat gag aag gtt cta tgg aca cca tct aaa gtc att gct         680
Glu Gln Ile Asn Glu Lys Val Leu Trp Thr Pro Ser Lys Val Ile Ala
    195                 200                 205 cgt ctg ggt aaa gaa att aat gat gaa acc tca tac ttg tat tgg gct         728
Arg Leu Gly Lys Glu Ile Asn Asp Glu Thr Ser Tyr Leu Tyr Trp Ala
210                 215                 220                 225 tac aag aac cgg att cct gtc ttc tgt cct ggc ttg acg gat gga tca         776
Tyr Lys Asn Arg Ile Pro Val Phe Cys Pro Gly Leu Thr Asp Gly Ser
                230                 235                 240 ctt ggt gac atg cta tac ttc cat tct ttc aaa aag ggt gat cca gat         824
Leu Gly Asp Met Leu Tyr Phe His Ser Phe Lys Lys Gly Asp Pro Asp
            245                 250                 255 aat cca gat ctt aat cct ggt cta gtc ata gac att gta gga gat att         872
Asn Pro Asp Leu Asn Pro Gly Leu Val Ile Asp Ile Val Gly Asp Ile
        260                 265                 270 agg gcc atg aat ggt gaa gct gtc cat gct ggt ttg agg aag aca gga         920
Arg Ala Met Asn Gly Glu Ala Val His Ala Gly Leu Arg Lys Thr Gly
    275                 280                 285 atg att ata ctg ggt gga ggg ctg cct aag cac cat gtt tgc aat gcc         968
Met Ile Ile Leu Gly Gly Gly Leu Pro Lys His His Val Cys Asn Ala
290                 295                 300                 305 aat atg atg cgc aat ggt gca gat ttt gcc gtc ttc att aac acc gca        1016
Asn Met Met Arg Asn Gly Ala Asp Phe Ala Val Phe Ile Asn Thr Ala
                310                 315                 320 caa gag ttt gat ggt agt gac tct ggt gcc cgt cct gat gaa gct gta        1064
Gln Glu Phe Asp Gly Ser Asp Ser Gly Ala Arg Pro Asp Glu Ala Val
            325                 330                 335 tca tgg gga aag ata cgt ggt ggt gcc aag act gtg aag gtg cat tgt        1112
Ser Trp Gly Lys Ile Arg Gly Gly Ala Lys Thr Val Lys Val His Cys
        340                 345                 350 gat gca acc att gca ttt ccc ata tta gta gct gag aca ttt gca gct        1160
Asp Ala Thr Ile Ala Phe Pro Ile Leu Val Ala Glu Thr Phe Ala Ala
    355                 360                 365 aag agt aag gaa ttc tcc cag ata agg tgc caa gtt tgaacattga             1206
Lys Ser Lys Glu Phe Ser Gln Ile Arg Cys Gln Val
370                 375                 380 ggaagctgtc cttccgacca cacatatgaa ttgctagctt ttgaagccaa cttgctagtg      1266
tgcagcacca tttattctgc aaaactgact agagagcagg gtatattcct ctaccccgag      1326
ttagacgaca tcctgtatgg ttcaaattaa ttatttttct ccccttcaca ccatgttatt      1386
```

```
tagttctctt cctcttcgaa agtgaagagc ttagatgttc ataggttttg aattatgttg      1446
gaggttggtg ataactgact agtcctctta ccatatagat aatgtatcct tgtactatga      1506
gattttgggt gtgtttgata ccaaggaaaa tgtttatttg gaaaacaatt ggatttttaa      1566
tttatttttt cttgtttaaa aaaaaaaaaa aaaaaaaaa aaa                         1609
```

<210> SEQ ID NO 2
<211> LENGTH: 381
<212> TYPE: PRT
<213> ORGANISM: Lycopersicon sp.
<220> FEATURE:
<223> OTHER INFORMATION: DHS

<400> SEQUENCE: 2

```
Met Gly Glu Ala Leu Lys Tyr Ser Ile Met Asp Ser Val Arg Ser Val
 1               5                  10                  15

Val Phe Lys Glu Ser Glu Asn Leu Glu Gly Ser Cys Thr Lys Ile Glu
            20                  25                  30

Gly Tyr Asp Phe Asn Lys Gly Val Asn Tyr Ala Glu Leu Ile Lys Ser
        35                  40                  45

Met Val Ser Thr Gly Phe Gln Ala Ser Asn Leu Gly Asp Ala Ile Ala
    50                  55                  60

Ile Val Asn Gln Met Leu Asp Trp Arg Leu Ser His Glu Leu Pro Thr
65                  70                  75                  80

Glu Asp Cys Ser Glu Glu Arg Asp Val Ala Tyr Arg Glu Ser Val
            85                  90                  95

Thr Cys Lys Ile Phe Leu Gly Phe Thr Ser Asn Leu Val Ser Ser Gly
           100                 105                 110

Val Arg Asp Thr Val Arg Tyr Leu Val Gln His Arg Met Val Asp Val
           115                 120                 125

Val Val Thr Thr Ala Gly Gly Ile Glu Glu Asp Leu Ile Lys Cys Leu
       130                 135                 140

Ala Pro Thr Tyr Lys Gly Asp Phe Ser Leu Pro Gly Ala Ser Leu Arg
145                 150                 155                 160

Ser Lys Gly Leu Asn Arg Ile Gly Asn Leu Leu Val Pro Asn Asp Asn
                165                 170                 175

Tyr Cys Lys Phe Glu Asn Trp Ile Ile Pro Val Phe Asp Gln Met Tyr
            180                 185                 190

Glu Glu Gln Ile Asn Glu Lys Val Leu Trp Thr Pro Ser Lys Val Ile
        195                 200                 205

Ala Arg Leu Gly Lys Glu Ile Asn Asp Glu Thr Ser Tyr Leu Tyr Trp
    210                 215                 220

Ala Tyr Lys Asn Arg Ile Pro Val Phe Cys Pro Gly Leu Thr Asp Gly
225                 230                 235                 240

Ser Leu Gly Asp Met Leu Tyr Phe His Ser Phe Lys Lys Gly Asp Pro
                245                 250                 255

Asp Asn Pro Asp Leu Asn Pro Gly Leu Val Ile Asp Ile Val Gly Asp
            260                 265                 270

Ile Arg Ala Met Asn Gly Glu Ala Val His Ala Gly Leu Arg Lys Thr
        275                 280                 285

Gly Met Ile Ile Leu Gly Gly Gly Leu Pro Lys His His Val Cys Asn
    290                 295                 300

Ala Asn Met Met Arg Asn Gly Ala Asp Phe Ala Val Phe Ile Asn Thr
305                 310                 315                 320
```

```
Ala Gln Glu Phe Asp Gly Ser Asp Ser Gly Ala Arg Pro Asp Glu Ala
            325                 330                 335

Val Ser Trp Gly Lys Ile Arg Gly Gly Ala Lys Thr Val Lys Val His
        340                 345                 350

Cys Asp Ala Thr Ile Ala Phe Pro Ile Leu Val Ala Glu Thr Phe Ala
            355                 360                 365

Ala Lys Ser Lys Glu Phe Ser Gln Ile Arg Cys Gln Val
    370                 375                 380

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 3
agtctagaag gtgctcgtcc tgat                                              24

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 4
gactgcagtc gacatcgatt ttttttttttt tttt                                  34

<210> SEQ ID NO 5
<211> LENGTH: 2272
<212> TYPE: DNA
<213> ORGANISM: Arabidopsis sp.
<220> FEATURE:
<221> NAME/KEY: CDS
<222> LOCATION: (68..265, 348..536, 624..842, 979..1065,
       1154..1258, 1575..1862)

<400> SEQUENCE: 5
gaactcccaa aaccctctac tactacactt tcagatccaa ggaaatcaat tttgtcattc          60 gagcaac atg gag gat gat cgt gtt ttc tct tcg gtt cac tca aca gtt          109
        Met Glu Asp Asp Arg Val Phe Ser Ser Val His Ser Thr Val
          1               5                  10 ttc aaa gaa tcc gaa tca ttg gaa gga aag tgt gat aaa atc gaa gga          157
Phe Lys Glu Ser Glu Ser Leu Glu Gly Lys Cys Asp Lys Ile Glu Gly
 15                  20                  25                  30 tac gat ttc aat caa gga gta gat tac cca aag ctt atg cga tcc atg          205
Tyr Asp Phe Asn Gln Gly Val Asp Tyr Pro Lys Leu Met Arg Ser Met
             35                  40                  45 ctc acc acc gga ttt caa gcc tcg aat ctc ggc gaa gct att gat gtc          253
Leu Thr Thr Gly Phe Gln Ala Ser Asn Leu Gly Glu Ala Ile Asp Val
         50                  55                  60 gtc aat caa atg gttcgtttct cgaattcatc aaaaataaaa attccttctt              305
Val Asn Gln Met
             65 tttgttttcc tttgttttgg gtgaattagt aatgacaaag ag ttt gaa ttt gta          359
                                              Phe Glu Phe Val
                                                              70 ttg aag cta gat tgg aga ctg gct gat gaa act aca gta gct gaa gac          407
Leu Lys Leu Asp Trp Arg Leu Ala Asp Glu Thr Thr Val Ala Glu Asp
         75                  80                  85 tgt agt gaa gag gag aag aat cca tcg ttt aga gag tct gtc aag tgt          455
```

```
                Cys Ser Glu Glu Glu Lys Asn Pro Ser Phe Arg Glu Ser Val Lys Cys
                                90                  95                 100 aaa atc ttt cta ggt ttc act tca aat ctt gtt tca tct ggt gtt aga           503
Lys Ile Phe Leu Gly Phe Thr Ser Asn Leu Val Ser Ser Gly Val Arg
            105                 110                 115 gat act att cgt tat ctt gtt cag cat cat atg gtttgtgatt tttgctttat         556
Asp Thr Ile Arg Tyr Leu Val Gln His His Met
        120                 125 caccctgctt ttttatagat gttaaaattt tcgagcttta gttttgattt caatggtttt         616 tctgcag gtt gat gtt ata gtc acg aca act ggt ggt gtt gag gaa gat          665
        Val Asp Val Ile Val Thr Thr Thr Gly Gly Val Glu Glu Asp
            130                 135                 140 ctc ata aaa tgc ctt gca cct aca ttt aaa ggt gat ttc tct cta cct           713
Leu Ile Lys Cys Leu Ala Pro Thr Phe Lys Gly Asp Phe Ser Leu Pro
    145                 150                 155 gga gct tat tta agg tca aag gga ttg aac cga att ggg aat ttg ctg           761
Gly Ala Tyr Leu Arg Ser Lys Gly Leu Asn Arg Ile Gly Asn Leu Leu
160                 165                 170                 175 gtt cct aat gat aac tac tgc aag ttt gag gat tgg atc att ccc atc           809
Val Pro Asn Asp Asn Tyr Cys Lys Phe Glu Asp Trp Ile Ile Pro Ile
                180                 185                 190 ttt gac gag atg ttg aag gaa cag aaa gaa gag gtattgcttt atctttcctt         862
Phe Asp Glu Met Leu Lys Glu Gln Lys Glu Glu
            195                 200 tttatatgat ttgagatgat tctgtttgtg cgtcactagt ggagatagat tttgattcct         922
ctcttgcatc attgacttcg ttggtgaatc cttctttctc tggtttttcc ttgtag            978 aat gtg ttg tgg act cct tct aaa ctg tta gca cgg ctg gga aaa gaa          1026
Asn Val Leu Trp Thr Pro Ser Lys Leu Leu Ala Arg Leu Gly Lys Glu
            205                 210                 215 atc aac aat gag agt tca tac ctt tat tgg gca tac aag gtatccaaaa           1075
Ile Asn Asn Glu Ser Ser Tyr Leu Tyr Trp Ala Tyr Lys
220                 225                 230 ttttaacctt tttagttttt taatcatcct gtgaggaact cggggattta aattttccgc        1135
ttcttgtggt gtttgtag atg aat att cca gta ttc tgc cca ggg tta aca         1186
                    Met Asn Ile Pro Val Phe Cys Pro Gly Leu Thr
                                    235                 240 gat ggc tct ctt ggg gat atg ctg tat ttt cac tct ttt cgt acc tct         1234
Asp Gly Ser Leu Gly Asp Met Leu Tyr Phe His Ser Phe Arg Thr Ser
            245                 250                 255 ggc ctc atc atc gat gta gta caa ggtacttctt ttactcaata agtcagtgtg        1288
Gly Leu Ile Ile Asp Val Val Gln
            260                 265 ataaatattc ctgctacatc tagtgcagga atattgtaac tagtagtgca ttgtagcttt       1348
tccaattcag caacggactt tactgtaagt tgatatctaa aggttcaaac gggagctagg       1408
agaatagcat aggggcattc tgatttaggt ttggggcact gggttaagag ttagagaata       1468
ataatcttgt tagttgttta tcaaactctt tgatggttag tctcttggta atttgaattt       1528
tatcacagtg tttatggtct ttgaaccagt taatgtttta tgaaca gat atc aga          1583
                                                        Asp Ile Arg gct atg aac ggc gaa gct gtc cat gca aat cct aaa aag aca ggg atg         1631
Ala Met Asn Gly Glu Ala Val His Ala Asn Pro Lys Lys Thr Gly Met
270                 275                 280                 285 ata atc ctt gga ggg ggc ttg cca aag cac cac ata tgt aat gcc aat         1679
Ile Ile Leu Gly Gly Gly Leu Pro Lys His His Ile Cys Asn Ala Asn
            290                 295                 300 atg atg cgc aat ggt gca gat tac gct gta ttt ata aac acc ggg caa         1727
Met Met Arg Asn Gly Ala Asp Tyr Ala Val Phe Ile Asn Thr Gly Gln
```

-continued

```
Met Met Arg Asn Gly Ala Asp Tyr Ala Val Phe Ile Asn Thr Gly Gln
            305                 310                 315 gaa ttt gat ggg agc gac tcg ggt gca cgc cct gat gaa gcc gtg tct      1775
Glu Phe Asp Gly Ser Asp Ser Gly Ala Arg Pro Asp Glu Ala Val Ser
            320                 325                 330 tgg ggt aaa att agg ggt tct gct aaa acc gtt aag gtc tgc ttt tta      1823
Trp Gly Lys Ile Arg Gly Ser Ala Lys Thr Val Lys Val Cys Phe Leu
            335                 340                 345 att tct tca cat cct aat tta tat ctc act cag tgg ttt tgagtacata       1872
Ile Ser Ser His Pro Asn Leu Tyr Leu Thr Gln Trp Phe
350                 355                 360 tttaatattg gatcattctt gcaggtatac tgtgatgcta ccatagcctt cccattgttg    1932
gttgcagaaa catttgccac aaagagagac caaacctgtg agtctaagac ttaagaactg    1992
actggtcgtt ttggccatgg attcttaaag atcgttgctt tttgatttta cactggagtg    2052
accatataac actccacatt gatgtggctg tgacgcgaat tgtcttcttg cgaattgtac    2112
tttagtttct ctcaacctaa aatgatttgc agattgtgtt ttcgtttaaa acacaagagt    2172
cttgtagtca ataatccttt gccttataaa attattcagt tccaacaaca cattgtgatt    2232
ctgtgacaag tctcccgttg cctatgttca cttctctgcg                         2272

<210> SEQ ID NO 6
<211> LENGTH: 362
<212> TYPE: PRT
<213> ORGANISM: Arabidopsis sp.

<400> SEQUENCE: 6

Met Glu Asp Asp Arg Val Phe Ser Ser Val His Ser Thr Val Phe Lys
1               5                   10                  15

Glu Ser Glu Ser Leu Glu Gly Lys Cys Asp Lys Ile Glu Gly Tyr Asp
                20                  25                  30

Phe Asn Gln Gly Val Asp Tyr Pro Lys Leu Met Arg Ser Met Leu Thr
            35                  40                  45

Thr Gly Phe Gln Ala Ser Asn Leu Gly Glu Ala Ile Asp Val Val Asn
        50                  55                  60

Gln Met Phe Glu Phe Val Leu Lys Leu Asp Trp Arg Leu Ala Asp Glu
65                  70                  75                  80

Thr Thr Val Ala Glu Asp Cys Ser Glu Glu Lys Asn Pro Ser Phe
                85                  90                  95

Arg Glu Ser Val Lys Cys Lys Ile Phe Leu Gly Phe Thr Ser Asn Leu
            100                 105                 110

Val Ser Ser Gly Val Arg Asp Thr Ile Arg Tyr Leu Val Gln His His
        115                 120                 125

Met Val Asp Val Ile Val Thr Thr Gly Gly Val Glu Glu Asp Leu
    130                 135                 140

Ile Lys Cys Leu Ala Pro Thr Phe Lys Gly Asp Phe Ser Leu Pro Gly
145                 150                 155                 160

Ala Tyr Leu Arg Ser Lys Gly Leu Asn Arg Ile Gly Asn Leu Leu Val
                165                 170                 175

Pro Asn Asp Asn Tyr Cys Lys Phe Glu Asp Trp Ile Ile Pro Ile Phe
            180                 185                 190

Asp Glu Met Leu Lys Glu Gln Lys Glu Asn Val Leu Trp Thr Pro
        195                 200                 205

Ser Lys Leu Leu Ala Arg Leu Gly Lys Glu Ile Asn Asn Glu Ser Ser
210                 215                 220
```

-continued

| | | | | | | | | | | | | | | | |
|---|---|---|---|---|---|---|---|---|---|---|---|---|---|---|---|
|Tyr|Leu|Tyr|Trp|Ala|Tyr|Lys|Met|Asn|Ile|Pro|Val|Phe|Cys|Pro|Gly|
|225| | | |230| | | |235| | | |240| | | |
|Leu|Thr|Asp|Gly|Ser|Leu|Gly|Asp|Met|Leu|Tyr|Phe|His|Ser|Phe|Arg|
| | | | |245| | | |250| | | |255| | | |
|Thr|Ser|Gly|Leu|Ile|Ile|Asp|Val|Val|Gln|Asp|Ile|Arg|Ala|Met|Asn|
| | | |260| | | | |265| | | |270| | | |
|Gly|Glu|Ala|Val|His|Ala|Asn|Pro|Lys|Lys|Thr|Gly|Met|Ile|Ile|Leu|
| | |275| | | | |280| | | | |285| | | |
|Gly|Gly|Gly|Leu|Pro|Lys|His|His|Ile|Cys|Asn|Ala|Asn|Met|Met|Arg|
| |290| | | | |295| | | | |300| | | | |
|Asn|Gly|Ala|Asp|Tyr|Ala|Val|Phe|Ile|Asn|Thr|Gly|Gln|Glu|Phe|Asp|
|305| | | |310| | | |315| | | |320| | | |
|Gly|Ser|Asp|Ser|Gly|Ala|Arg|Pro|Asp|Glu|Ala|Val|Ser|Trp|Gly|Lys|
| | | | |325| | | |330| | | |335| | | |
|Ile|Arg|Gly|Ser|Ala|Lys|Thr|Val|Lys|Val|Cys|Phe|Leu|Ile|Ser|Ser|
| | | |340| | | | |345| | | |350| | | |
|His|Pro|Asn|Leu|Tyr|Leu|Thr|Gln|Trp|Phe| | | | | | |
| | |355| | | | |360| | | | | | | | |

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 7
ggtggtgttg aggaagatc                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 8
ggtgcacgcc ctgatgaagc                                                 20

<210> SEQ ID NO 9
<211> LENGTH: 1660
<212> TYPE: DNA
<213> ORGANISM: Dianthus sp.
<220> FEATURE:
<223> OTHER INFORMATION: DHS
<220> FEATURE:
<221> NAME/KEY: CDS
<222> LOCATION: (256)..(1374)

<400> SEQUENCE: 9

```
gtcattacaa tgcataggat cattgcacat gctaccttcc tcattgcact tgagcttgcc        60
atacttttgt ttttgacgtt tgataataat actatgaaaa tattatgttt tttctttttgt      120 gtgttggtgt ttttgaagtt gttttttgata agcagaaccc agttgtttta cacttttacc     180
attgaactac tgcaattcta aactttgtt tacattttaa ttccatcaaa gattgagttc       240
agcataggaa aaagg atg gag gat gct aat cat gat agt gtg gca tct gcg       291
               Met Glu Asp Ala Asn His Asp Ser Val Ala Ser Ala
                 1               5                  10 cac tct gca gca ttc aaa aag tcg gag aat tta gag ggg aaa agc gtt       339
His Ser Ala Ala Phe Lys Lys Ser Glu Asn Leu Glu Gly Lys Ser Val
         15                  20                  25
```

| | |
|---|---|
| aag att gag ggt tat gat ttt aat caa ggt gta aac tat tcc aaa ctc<br>Lys Ile Glu Gly Tyr Asp Phe Asn Gln Gly Val Asn Tyr Ser Lys Leu<br>30                         35                    40 | 387 |
| ttg caa tct ttc gct tct aat ggg ttt caa gcc tcg aat ctt gga gat<br>Leu Gln Ser Phe Ala Ser Asn Gly Phe Gln Ala Ser Asn Leu Gly Asp<br>45                       50                    55                    60 | 435 |
| gcc att gaa gta gtt aat cat atg cta gat tgg agt ctg gca gat gag<br>Ala Ile Glu Val Val Asn His Met Leu Asp Trp Ser Leu Ala Asp Glu<br>                   65                    70                    75 | 483 |
| gca cct gtg gac gat tgt agc gag gaa gag agg gat cct aaa ttc aga<br>Ala Pro Val Asp Asp Cys Ser Glu Glu Glu Arg Asp Pro Lys Phe Arg<br>        80                       85                    90 | 531 |
| gaa tct gtg aag tgc aaa gtg ttc ttg ggc ttt act tca aat ctt att<br>Glu Ser Val Lys Cys Lys Val Phe Leu Gly Phe Thr Ser Asn Leu Ile<br>           95                    100                  105 | 579 |
| tcc tct ggt gtt cgt gac aca att cgg tat ctc gtg caa cat cat atg<br>Ser Ser Gly Val Arg Asp Thr Ile Arg Tyr Leu Val Gln His His Met<br>110                      115                    120 | 627 |
| gtt gac gtg ata gta acg aca acc gga ggt ata gaa gaa gat cta ata<br>Val Asp Val Ile Val Thr Thr Thr Gly Gly Ile Glu Glu Asp Leu Ile<br>125                      130                    135                  140 | 675 |
| aaa gga aga tcc atc aag tgc ctt gca ccc act ttc aaa ggc gat ttt<br>Lys Gly Arg Ser Ile Lys Cys Leu Ala Pro Thr Phe Lys Gly Asp Phe<br>                  145                    150                    155 | 723 |
| gcc tta cca gga gct caa tta cgc tcc aaa ggg ttg aat cga att ggt<br>Ala Leu Pro Gly Ala Gln Leu Arg Ser Lys Gly Leu Asn Arg Ile Gly<br>                160                    165                    170 | 771 |
| aat ctg ttg gtt ccg aat gat aac tac tgt aaa ttt gag gat tgg atc<br>Asn Leu Leu Val Pro Asn Asp Asn Tyr Cys Lys Phe Glu Asp Trp Ile<br>175                      180                    185 | 819 |
| att cca att tta gat aag atg ttg gaa gag caa att tca gag aaa atc<br>Ile Pro Ile Leu Asp Lys Met Leu Glu Glu Gln Ile Ser Glu Lys Ile<br>        190                       195                    200 | 867 |
| tta tgg aca cca tcg aag ttg att ggt cga tta gga aga gaa ata aac<br>Leu Trp Thr Pro Ser Lys Leu Ile Gly Arg Leu Gly Arg Glu Ile Asn<br>205                      210                    215                  220 | 915 |
| gat gag agt tca tac ctt tac tgg gcc ttc aag aac aat att cca gta<br>Asp Glu Ser Ser Tyr Leu Tyr Trp Ala Phe Lys Asn Asn Ile Pro Val<br>                    225                    230                    235 | 963 |
| ttt tgc cca ggt tta aca gac ggc tca ctc gga gac atg cta tat ttt<br>Phe Cys Pro Gly Leu Thr Asp Gly Ser Leu Gly Asp Met Leu Tyr Phe<br>                240                    245                    250 | 1011 |
| cat tct ttt cgc aat ccg ggt tta atc gtc gat gtt gtg caa gat ata<br>His Ser Phe Arg Asn Pro Gly Leu Ile Val Asp Val Val Gln Asp Ile<br>                  255                    260                    265 | 1059 |
| aga gca gta aat ggc gag gct gtg cac gca gcg cct agg aaa aca ggc<br>Arg Ala Val Asn Gly Glu Ala Val His Ala Ala Pro Arg Lys Thr Gly<br>270                      275                    280 | 1107 |
| atg att ata ctc ggt gga ggg ttg cct aag cac cac atc tgc aac gca<br>Met Ile Ile Leu Gly Gly Gly Leu Pro Lys His His Ile Cys Asn Ala<br>285                      290                    295                  300 | 1155 |
| aac atg atg aga aat ggc gcc gat tat gct gtt ttc atc aac act gcc<br>Asn Met Met Arg Asn Gly Ala Asp Tyr Ala Val Phe Ile Asn Thr Ala<br>                  305                    310                    315 | 1203 |
| gaa gag ttt gac ggc agt gat tct ggt gct cgc ccc gat gag gct att<br>Glu Glu Phe Asp Gly Ser Asp Ser Gly Ala Arg Pro Asp Glu Ala Ile<br>        320                       325                    330 | 1251 |
| tca tgg ggc aaa att agc gga tct gct aag act gtg aag gtg cat tgt<br>Ser Trp Gly Lys Ile Ser Gly Ser Ala Lys Thr Val Lys Val His Cys | 1299 |

-continued

```
                335                 340                 345
gat gcc acg ata gct ttc cct cta cta gtc gct gag aca ttt gca gca      1347
Asp Ala Thr Ile Ala Phe Pro Leu Leu Val Ala Glu Thr Phe Ala Ala
    350                 355                 360 aaa aga gaa aaa gag agg aag agc tgt taaaactttt ttgattgttg             1394
Lys Arg Glu Lys Glu Arg Lys Ser Cys
365                 370 aaaaatctgt gttatacaag tctcgaaatg cattttagta attgacttga tcttatcatt     1454
tcaatgtgtt atctttgaaa atgttggtaa tgaaacatct cacctcttct atacaacatt     1514
gttgatccat tgtactccgt atcttgtaat tttggaaaaa aaaaaccgtc tattgttacg     1574
agagagtaca tttttgaggt aaaaatatag gattttgtgt cgatgcaaat gctggttatt     1634
cccttgaaaa aaaaaaaaaa aaaaaa                                          1660
```

<210> SEQ ID NO 10
<211> LENGTH: 373
<212> TYPE: PRT
<213> ORGANISM: Dianthus sp.
<220> FEATURE:
<223> OTHER INFORMATION: DHS

<400> SEQUENCE: 10

```
Met Glu Asp Ala Asn His Asp Ser Val Ala Ser Ala His Ser Ala Ala
  1               5                  10                  15

Phe Lys Lys Ser Glu Asn Leu Glu Gly Lys Ser Val Lys Ile Glu Gly
             20                  25                  30

Tyr Asp Phe Asn Gln Gly Val Asn Tyr Ser Lys Leu Leu Gln Ser Phe
         35                  40                  45

Ala Ser Asn Gly Phe Gln Ala Ser Asn Leu Gly Asp Ala Ile Glu Val
     50                  55                  60

Val Asn His Met Leu Asp Trp Ser Leu Ala Asp Glu Ala Pro Val Asp
 65                  70                  75                  80

Asp Cys Ser Glu Glu Glu Arg Asp Pro Lys Phe Arg Glu Ser Val Lys
                 85                  90                  95

Cys Lys Val Phe Leu Gly Phe Thr Ser Asn Leu Ile Ser Ser Gly Val
            100                 105                 110

Arg Asp Thr Ile Arg Tyr Leu Val Gln His His Met Val Asp Val Ile
        115                 120                 125

Val Thr Thr Thr Gly Gly Ile Glu Glu Asp Leu Ile Lys Gly Arg Ser
    130                 135                 140

Ile Lys Cys Leu Ala Pro Thr Phe Lys Gly Asp Phe Ala Leu Pro Gly
145                 150                 155                 160

Ala Gln Leu Arg Ser Lys Gly Leu Asn Arg Ile Gly Asn Leu Leu Val
                165                 170                 175

Pro Asn Asp Asn Tyr Cys Lys Phe Glu Asp Trp Ile Ile Pro Ile Leu
            180                 185                 190

Asp Lys Met Leu Glu Glu Gln Ile Ser Glu Lys Ile Leu Trp Thr Pro
        195                 200                 205

Ser Lys Leu Ile Gly Arg Leu Gly Arg Glu Ile Asn Asp Glu Ser Ser
    210                 215                 220

Tyr Leu Tyr Trp Ala Phe Lys Asn Asn Ile Pro Val Phe Cys Pro Gly
225                 230                 235                 240

Leu Thr Asp Gly Ser Leu Gly Asp Met Leu Tyr Phe His Ser Phe Arg
                245                 250                 255

Asn Pro Gly Leu Ile Val Asp Val Val Gln Asp Ile Arg Ala Val Asn
```

-continued

```
                    260                 265                 270
Gly Glu Ala Val His Ala Ala Pro Arg Lys Thr Gly Met Ile Ile Leu
                275                 280                 285
Gly Gly Gly Leu Pro Lys His His Ile Cys Asn Ala Asn Met Met Arg
            290                 295                 300
Asn Gly Ala Asp Tyr Ala Val Phe Ile Asn Thr Ala Glu Glu Phe Asp
305                 310                 315                 320
Gly Ser Asp Ser Gly Ala Arg Pro Asp Glu Ala Ile Ser Trp Gly Lys
                325                 330                 335
Ile Ser Gly Ser Ala Lys Thr Val Lys Val His Cys Asp Ala Thr Ile
            340                 345                 350
Ala Phe Pro Leu Leu Val Ala Glu Thr Phe Ala Ala Lys Arg Glu Lys
        355                 360                 365
Glu Arg Lys Ser Cys
    370
```

```
<210> SEQ ID NO 11
<211> LENGTH: 780
<212> TYPE: DNA
<213> ORGANISM: Lycopersicon sp.
<220> FEATURE:
<223> OTHER INFORMATION: eif-5A
<220> FEATURE:
<221> NAME/KEY: CDS
<222> LOCATION: (43)..(522)

<400> SEQUENCE: 11
```

```
aaagaatcct agagagagaa agggaatcct agagagagaa gc atg tcg gac gaa        54
                                              Met Ser Asp Glu
                                                1 gaa cac cat ttt gag tca aag gca gat gct ggt gcc tca aaa act ttc      102
Glu His His Phe Glu Ser Lys Ala Asp Ala Gly Ala Ser Lys Thr Phe
  5               10                  15                  20 cca cag caa gct gga acc atc cgt aag aat ggt tac atc gtt atc aaa     150
Pro Gln Gln Ala Gly Thr Ile Arg Lys Asn Gly Tyr Ile Val Ile Lys
                  25                  30                  35 ggc cgt ccc tgc aag gtt gtt gag gtc tcc act tca aaa act gga aaa     198
Gly Arg Pro Cys Lys Val Val Glu Val Ser Thr Ser Lys Thr Gly Lys
              40                  45                  50 cac gga cat gct aaa tgt cac ttt gtg gca att gac att ttc aat gga     246
His Gly His Ala Lys Cys His Phe Val Ala Ile Asp Ile Phe Asn Gly
          55                  60                  65 aag aaa ctg gaa gat atc gtt ccg tcc tcc cac aat tgt gat gtg cca     294
Lys Lys Leu Glu Asp Ile Val Pro Ser Ser His Asn Cys Asp Val Pro
      70                  75                  80 cat gtt aac cgt acc gac tat cag ctg att gat atc tct gaa gat ggt     342
His Val Asn Arg Thr Asp Tyr Gln Leu Ile Asp Ile Ser Glu Asp Gly
 85                  90                  95                 100 ttt gtc tca ctt ctt act gaa agt gga aac acc aag gat gac ctc agg     390
Phe Val Ser Leu Leu Thr Glu Ser Gly Asn Thr Lys Asp Asp Leu Arg
                 105                 110                 115 ctt ccc acc gat gaa aat ctg ctg aag cag gtt aaa gat ggg ttc cag     438
Leu Pro Thr Asp Glu Asn Leu Leu Lys Gln Val Lys Asp Gly Phe Gln
             120                 125                 130 gaa gga aag gat ctt gtg gtg tct gtt atg tct gcg atg ggc gaa gag     486
Glu Gly Lys Asp Leu Val Val Ser Val Met Ser Ala Met Gly Glu Glu
         135                 140                 145 cag att aac gcc gtt aag gat gtt ggt acc aag aat tagttatgtc          532
Gln Ile Asn Ala Val Lys Asp Val Gly Thr Lys Asn
     150                 155                 160
```

```
atggcagcat aatcactgcc aaagctttaa gacattatca tatcctaatg tggtactttg      592
atatcactag attataaact gtgttatttg cactgttcaa acaaaagaa agaaaactgc       652 tgttatggct agagaaagta ttggctttga gcttttgaca gcacagttga actatgtgaa      712
aattctactt tttttttttt gggtaaaata ctgctcgttt aatgttttgc aaaaaaaaaa      772
aaaaaaaa                                                               780
```

```
<210> SEQ ID NO 12
<211> LENGTH: 160
<212> TYPE: PRT
<213> ORGANISM: Lycopersicon sp.
<220> FEATURE:
<223> OTHER INFORMATION: eif-5A

<400> SEQUENCE: 12
```

```
Met Ser Asp Glu Glu His His Phe Glu Ser Lys Ala Asp Ala Gly Ala
  1               5                  10                  15

Ser Lys Thr Phe Pro Gln Gln Ala Gly Thr Ile Arg Lys Asn Gly Tyr
             20                  25                  30

Ile Val Ile Lys Gly Arg Pro Cys Lys Val Val Glu Val Ser Thr Ser
         35                  40                  45

Lys Thr Gly Lys His Gly His Ala Lys Cys His Phe Val Ala Ile Asp
     50                  55                  60

Ile Phe Asn Gly Lys Lys Leu Glu Asp Ile Val Pro Ser Ser His Asn
 65                  70                  75                  80

Cys Asp Val Pro His Val Asn Arg Thr Asp Tyr Gln Leu Ile Asp Ile
                 85                  90                  95

Ser Glu Asp Gly Phe Val Ser Leu Leu Thr Glu Ser Gly Asn Thr Lys
            100                 105                 110

Asp Asp Leu Arg Leu Pro Thr Asp Glu Asn Leu Leu Lys Gln Val Lys
        115                 120                 125

Asp Gly Phe Gln Glu Gly Lys Asp Leu Val Val Ser Val Met Ser Ala
    130                 135                 140

Met Gly Glu Glu Gln Ile Asn Ala Val Lys Asp Val Gly Thr Lys Asn
145                 150                 155                 160
```

```
<210> SEQ ID NO 13
<211> LENGTH: 812
<212> TYPE: DNA
<213> ORGANISM: Dianthus sp.
<220> FEATURE:
<223> OTHER INFORMATION: eif-5A
<220> FEATURE:
<221> NAME/KEY: CDS
<222> LOCATION: (67)..(546)

<400> SEQUENCE: 13
```

```
ctctttaca tcaatcgaaa aaaaattagg gttcttattt tagagtgaga ggcgaaaaat       60 cgaacg atg tcg gac gac gat cac cat ttc gag tca tcg gcc gac gcc        108
       Met Ser Asp Asp Asp His His Phe Glu Ser Ser Ala Asp Ala
         1               5                  10 gga gca tcc aag act tac cct caa caa gct ggt aca atc cgc aag agc       156
Gly Ala Ser Lys Thr Tyr Pro Gln Gln Ala Gly Thr Ile Arg Lys Ser
 15                  20                  25                  30 ggt cac atc gtc atc aaa aat cgc cct tgc aag gtg gtt gag gtt tct       204
Gly His Ile Val Ile Lys Asn Arg Pro Cys Lys Val Val Glu Val Ser
             35                  40                  45 acc tcc aag act ggc aag cac ggt cat gcc aaa tgt cac ttt gtt gcc       252
```

```
                Thr Ser Lys Thr Gly Lys His Gly His Ala Lys Cys His Phe Val Ala
                            50                  55                  60 att gac att ttc aac ggc aag aag ctg gaa gat att gtc ccc tca tcc         300
Ile Asp Ile Phe Asn Gly Lys Lys Leu Glu Asp Ile Val Pro Ser Ser
            65                  70                  75 cac aat tgt gat gtt cca cat gtc aac cgt gtc gac tac cag ctg ctt         348
His Asn Cys Asp Val Pro His Val Asn Arg Val Asp Tyr Gln Leu Leu
        80                  85                  90 gat atc act gaa gat ggc ttt gtt agt ctg ctg act gac agt ggt gac         396
Asp Ile Thr Glu Asp Gly Phe Val Ser Leu Leu Thr Asp Ser Gly Asp
95                  100                 105                 110 acc aag gat gat ctg aag ctt cct gct gat gag gcc ctt gtg aag cag         444
Thr Lys Asp Asp Leu Lys Leu Pro Ala Asp Glu Ala Leu Val Lys Gln
                115                 120                 125 atg aag gag gga ttt gag gcg ggg aaa gac ttg att ctg tca gtc atg         492
Met Lys Glu Gly Phe Glu Ala Gly Lys Asp Leu Ile Leu Ser Val Met
            130                 135                 140 tgt gca atg gga gaa gag cag atc tgc gcc gtc aag gac gtt agt ggt         540
Cys Ala Met Gly Glu Glu Gln Ile Cys Ala Val Lys Asp Val Ser Gly
        145                 150                 155 ggc aag tagaagcttt tgatgaatcc aatactacgc ggtgcagttg aagcaatagt         596
Gly Lys
    160 aatctcgaga acattctgaa ccttatatgt tgaattgatg gtgcttagtt tgttttggaa       656 atctctttgc aattaagttg taccaaatca atggatgtaa tgtcttgaat tgtttttatt       716 tttgttttga tgtttgctgt gattgcatta tgcattgtta tgagttatga cctgttataa       776 cacaaggttt tggtaaaaaa aaaaaaaaaa aaaaaa                                 812

<210> SEQ ID NO 14
<211> LENGTH: 160
<212> TYPE: PRT
<213> ORGANISM: Dianthus sp.
<220> FEATURE:
<223> OTHER INFORMATION: eif-5A

<400> SEQUENCE: 14

Met Ser Asp Asp His His Phe Glu Ser Ser Ala Asp Ala Gly Ala
1               5                   10                  15

Ser Lys Thr Tyr Pro Gln Gln Ala Gly Thr Ile Arg Lys Ser Gly His
            20                  25                  30

Ile Val Ile Lys Asn Arg Pro Cys Lys Val Val Glu Val Ser Thr Ser
        35                  40                  45

Lys Thr Gly Lys His Gly His Ala Lys Cys His Phe Val Ala Ile Asp
    50                  55                  60

Ile Phe Asn Gly Lys Lys Leu Glu Asp Ile Val Pro Ser Ser His Asn
65                  70                  75                  80

Cys Asp Val Pro His Val Asn Arg Val Asp Tyr Gln Leu Leu Asp Ile
                85                  90                  95

Thr Glu Asp Gly Phe Val Ser Leu Leu Thr Asp Ser Gly Asp Thr Lys
            100                 105                 110

Asp Asp Leu Lys Leu Pro Ala Asp Glu Ala Leu Val Lys Gln Met Lys
        115                 120                 125

Glu Gly Phe Glu Ala Gly Lys Asp Leu Ile Leu Ser Val Met Cys Ala
    130                 135                 140

Met Gly Glu Glu Gln Ile Cys Ala Val Lys Asp Val Ser Gly Gly Lys
145                 150                 155                 160
```

<210> SEQ ID NO 15
<211> LENGTH: 702
<212> TYPE: DNA
<213> ORGANISM: Arabidopsis sp.
<220> FEATURE:
<223> OTHER INFORMATION: eif-5A
<220> FEATURE:
<221> NAME/KEY: CDS
<222> LOCATION: (56)..(529)

<400> SEQUENCE: 15

```
ctgttaccaa aaatctgta ccgcaaaatc ctcgtcgaag ctcgctgctg caacc atg      58
                                                             Met
                                                               1 tcc gac gag gag cat cac ttt gag tcc agt gac gcc gga gcg tcc aaa     106
Ser Asp Glu Glu His His Phe Glu Ser Ser Asp Ala Gly Ala Ser Lys
          5                  10                  15 acc tac cct caa caa gct gga acc atc cgt aag aat ggt tac atc gtc     154
Thr Tyr Pro Gln Gln Ala Gly Thr Ile Arg Lys Asn Gly Tyr Ile Val
     20                  25                  30 atc aaa aat cgt ccc tgc aag gtt gtt gag gtt tca acc tcg aag act     202
Ile Lys Asn Arg Pro Cys Lys Val Val Glu Val Ser Thr Ser Lys Thr
 35                  40                  45 ggc aag cat ggt cat gct aaa tgt cat ttt gta gct att gat atc ttc     250
Gly Lys His Gly His Ala Lys Cys His Phe Val Ala Ile Asp Ile Phe
 50                  55                  60                  65 acc agc aag aaa ctc gaa gat att gtt cct tct tcc cac aat tgt gat     298
Thr Ser Lys Lys Leu Glu Asp Ile Val Pro Ser Ser His Asn Cys Asp
                 70                  75                  80 gtt cct cat gtc aac cgt act gat tat cag ctg att gac att tct gaa     346
Val Pro His Val Asn Arg Thr Asp Tyr Gln Leu Ile Asp Ile Ser Glu
             85                  90                  95 gat gga tat gtc agt ttg ttg act gat aac ggt agt acc aag gat gac     394
Asp Gly Tyr Val Ser Leu Leu Thr Asp Asn Gly Ser Thr Lys Asp Asp
         100                 105                 110 ctt aag ctc cct aat gat gac act ctg ctc caa cag atc aag agt ggg     442
Leu Lys Leu Pro Asn Asp Asp Thr Leu Leu Gln Gln Ile Lys Ser Gly
     115                 120                 125 ttt gat gat gga aaa gat cta gtg gtg agt gta atg tca gct atg gga     490
Phe Asp Asp Gly Lys Asp Leu Val Val Ser Val Met Ser Ala Met Gly
130                 135                 140                 145 gag gaa cag atc aat gct ctt aag gac atc ggt ccc aag tgagactaac      539
Glu Glu Gln Ile Asn Ala Leu Lys Asp Ile Gly Pro Lys
                 150                 155 aaagcctccc ctttgttatg agattcttct tcttctgtag gcttccatta ctcgtcggag   599
attatcttgt ttttgggtta ctcctatttt ggatatttaa acttttgtta ataatgccat   659
cttcttcaac cttttccttc tagatggttt ttatacttct tct                     702
```

<210> SEQ ID NO 16
<211> LENGTH: 158
<212> TYPE: PRT
<213> ORGANISM: Arabidopsis sp.
<220> FEATURE:
<223> OTHER INFORMATION: eif-5A

<400> SEQUENCE: 16

```
Met Ser Asp Glu Glu His His Phe Glu Ser Ser Asp Ala Gly Ala Ser
  1               5                  10                  15

Lys Thr Tyr Pro Gln Gln Ala Gly Thr Ile Arg Lys Asn Gly Tyr Ile
             20                  25                  30
```

```
Val Ile Lys Asn Arg Pro Cys Lys Val Val Glu Val Ser Thr Ser Lys
         35                  40                  45

Thr Gly Lys His Gly His Ala Lys Cys His Phe Val Ala Ile Asp Ile
 50                  55                  60

Phe Thr Ser Lys Lys Leu Glu Asp Ile Val Pro Ser Ser His Asn Cys
 65                  70                  75                  80

Asp Val Pro His Val Asn Arg Thr Asp Tyr Gln Leu Ile Asp Ile Ser
                 85                  90                  95

Glu Asp Gly Tyr Val Ser Leu Leu Thr Asp Asn Gly Ser Thr Lys Asp
                100                 105                 110

Asp Leu Lys Leu Pro Asn Asp Asp Thr Leu Leu Gln Gln Ile Lys Ser
            115                 120                 125

Gly Phe Asp Asp Gly Lys Asp Leu Val Val Ser Val Met Ser Ala Met
130                 135                 140

Gly Glu Glu Gln Ile Asn Ala Leu Lys Asp Ile Gly Pro Lys
145                 150                 155
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
aaarrycgmc cytgcaaggt                                              20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 18
aatacgactc actatag                                                 17

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" bases represent a, t, c, g, other or
      unknown

<400> SEQUENCE: 19
tcyttnccyt cmkctaahcc                                              20

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 20 attaccctc actaaag                                                  17

<210> SEQ ID NO 21
<211> LENGTH: 22
<212> TYPE: DNA

```
<213> ORGANISM: Artificial Sequence
<220> FEATURE:
<223> OTHER INFORMATION: Description of Artificial Sequence: primer

<400> SEQUENCE: 21
ctgttaccaa aaatctgta cc                                               22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 22
agaagaagta taaaaaccat c                                               21

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 23
aaagaatcct agagagagaa agg                                             23

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 24
ttttacatca atcgaaaa                                                   18

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 25
accaaaacct gtgttataac tcc                                             23

<210> SEQ ID NO 26
<211> LENGTH: 581
<212> TYPE: DNA
<213> ORGANISM: Arabidopsis sp.
<220> FEATURE:
<223> OTHER INFORMATION: DHS
<220> FEATURE:
<221> NAME/KEY: CDS
<222> LOCATION: (1)..(579)

<400> SEQUENCE: 26 ggt ggt gtt gag gaa gat ctc ata aaa tgc ctt gca cct aca ttt aaa        48
Gly Gly Val Glu Glu Asp Leu Ile Lys Cys Leu Ala Pro Thr Phe Lys
  1               5                  10                  15 ggt gat ttc tct cta cct gga gct tat tta agg tca aag gga ttg aac        96
Gly Asp Phe Ser Leu Pro Gly Ala Tyr Leu Arg Ser Lys Gly Leu Asn
             20                  25                  30 cga att ggg aat ttg ctg gtt cct aat gat aac tac tgc aag ttt gag       144
Arg Ile Gly Asn Leu Leu Val Pro Asn Asp Asn Tyr Cys Lys Phe Glu
```

```
gat tgg atc att ccc atc ttt gac gag atg ttg aag gaa cag aaa gaa    192
Asp Trp Ile Ile Pro Ile Phe Asp Glu Met Leu Lys Glu Gln Lys Glu
 50                  55                  60 gag aat gtg ttg tgg act cct tct aaa ctg tta gca cgg ctg gga aaa    240
Glu Asn Val Leu Trp Thr Pro Ser Lys Leu Leu Ala Arg Leu Gly Lys
 65                  70                  75                  80 gaa atc aac aat gag agt tca tac ctt tat tgg gca tac aag atg aat    288
Glu Ile Asn Asn Glu Ser Ser Tyr Leu Tyr Trp Ala Tyr Lys Met Asn
                 85                  90                  95 att cca gta ttc tgc cca ggg tta aca gat ggc tct ctt agg gat atg    336
Ile Pro Val Phe Cys Pro Gly Leu Thr Asp Gly Ser Leu Arg Asp Met
             100                 105                 110 ctg tat ttt cac tct ttt cgt acc tct ggc ctc atc atc gat gta gta    384
Leu Tyr Phe His Ser Phe Arg Thr Ser Gly Leu Ile Ile Asp Val Val
         115                 120                 125 caa gat atc aga gct atg aac ggc gaa gct gtc cat gca aat cct aaa    432
Gln Asp Ile Arg Ala Met Asn Gly Glu Ala Val His Ala Asn Pro Lys
130                 135                 140 aag aca ggg atg ata atc ctt gga ggg ggc ttg cca aag cac cac ata    480
Lys Thr Gly Met Ile Ile Leu Gly Gly Gly Leu Pro Lys His His Ile
145                 150                 155                 160 tgt aat gcc aat atg atg cgc aat ggt gca gat tac gct gta ttt ata    528
Cys Asn Ala Asn Met Met Arg Asn Gly Ala Asp Tyr Ala Val Phe Ile
                165                 170                 175 aac acc ggg caa gaa ttt gat ggg agc gac tcg ggt gca cgc cct gat    576
Asn Thr Gly Gln Glu Phe Asp Gly Ser Asp Ser Gly Ala Arg Pro Asp
            180                 185                 190 gaa gc                                                              581
Glu
```

<210> SEQ ID NO 27
<211> LENGTH: 522
<212> TYPE: DNA
<213> ORGANISM: Dianthus sp.
<220> FEATURE:
<223> OTHER INFORMATION: DHS
<220> FEATURE:
<221> NAME/KEY: CDS
<222> LOCATION: (3)..(521)

<400> SEQUENCE: 27

```
ga aga tcc atc aag tgc ctt gca ccc act ttc aaa ggc gat ttt gcc      47
   Arg Ser Ile Lys Cys Leu Ala Pro Thr Phe Lys Gly Asp Phe Ala
    1               5                  10                  15 tta cca gga gct caa tta cgc tcc aaa ggg ttg aat cga att ggt aat     95
Leu Pro Gly Ala Gln Leu Arg Ser Lys Gly Leu Asn Arg Ile Gly Asn
             20                  25                  30 ctg ttg gtt ccg aat gat aac tac tgt aaa ttt gag gat tgg atc att    143
Leu Leu Val Pro Asn Asp Asn Tyr Cys Lys Phe Glu Asp Trp Ile Ile
         35                  40                  45 cca att tta gat aag atg ttg gaa gag caa att tca gag aaa atc tta    191
Pro Ile Leu Asp Lys Met Leu Glu Glu Gln Ile Ser Glu Lys Ile Leu
     50                  55                  60 tgg aca cca tcg aag ttg att ggt cga tta gga aga gaa ata aac gat    239
Trp Thr Pro Ser Lys Leu Ile Gly Arg Leu Gly Arg Glu Ile Asn Asp
 65                  70                  75 gag agt tca tac ctt tac tgg gcc ttc aag aac aat att cca gta ttt    287
Glu Ser Ser Tyr Leu Tyr Trp Ala Phe Lys Asn Asn Ile Pro Val Phe
 80                  85                  90                  95 tgc cca ggt tta aca gac ggc tca ctc gga gac atg cta tat ttt cat    335
Cys Pro Gly Leu Thr Asp Gly Ser Leu Gly Asp Met Leu Tyr Phe His
```

```
                Cys Pro Gly Leu Thr Asp Gly Ser Leu Gly Asp Met Leu Tyr Phe His
                                100                 105                 110 tct ttt cgc aat ccg ggt tta atc atc gat gtt gtg caa gat ata aga          383
Ser Phe Arg Asn Pro Gly Leu Ile Ile Asp Val Val Gln Asp Ile Arg
            115                 120                 125 gca gta aat ggc gag gct gtg cac gca gcg cct agg aaa aca ggc atg          431
Ala Val Asn Gly Glu Ala Val His Ala Ala Pro Arg Lys Thr Gly Met
        130                 135                 140 att ata ctc ggt gga ggg ttg cct aag cac cac atc tgc aac gca aac          479
Ile Ile Leu Gly Gly Gly Leu Pro Lys His His Ile Cys Asn Ala Asn
    145                 150                 155 atg atg aga aat ggc gcc gat tat gct gtt ttc atc aac acc g                522
Met Met Arg Asn Gly Ala Asp Tyr Ala Val Phe Ile Asn Thr
160                 165                 170

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 28
ttgargaaga tycatmaart gcct                                                24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 29
ccatcaaayt cytgkgcrgt gtt                                                 23

<210> SEQ ID NO 30
<211> LENGTH: 484
<212> TYPE: DNA
<213> ORGANISM: Arabidopsis sp.
<220> FEATURE:
<223> OTHER INFORMATION: DHS
<220> FEATURE:
<221> NAME/KEY: CDS
<222> LOCATION: (2)..(112)

<400> SEQUENCE: 30 t gca cgc cct gat gaa gct gtg tct tgg ggt aaa att agg ggt tct gct        49
  Ala Arg Pro Asp Glu Ala Val Ser Trp Gly Lys Ile Arg Gly Ser Ala
  1               5                  10                  15 aaa acc gtt aag gtc tgc ttt tta att tct tca cat cct aat tta tat         97
Lys Thr Val Lys Val Cys Phe Leu Ile Ser Ser His Pro Asn Leu Tyr
            20                  25                  30 ctc act cag tgg ttt tgagtacata tttaatattg gatcattctt gcaggtatac        152
Leu Thr Gln Trp Phe
            35 tgtgatgcta ccatagcctt cccattgttg gttgcagaaa catttgccac aaagagagac      212 caaacctgtg agtctaagac ttaagaactg actggtcgtt ttggccatgg attcttaaag      272 atcgttgctt tttgatttta cactggagtg accatataac actccacatt gatgtggctg      332 tgacgcgaat tgtcttcttg cgaattgtac tttagtttct ctcaacctaa aatgatttgc      392 agattgtgtt ttcgttttaaa acacaagagt cttgtagtca ataatccttt gccttataaa     452 attattcagt tccaacaaaa aaaaaaaaaa aa                                    484
```

<210> SEQ ID NO 31
<211> LENGTH: 559
<212> TYPE: DNA
<213> ORGANISM: Lycopersicon sp.
<220> FEATURE:
<223> OTHER INFORMATION: DHS
<220> FEATURE:
<221> NAME/KEY: CDS
<222> LOCATION: (1)..(156)
<220> FEATURE:
<223> OTHER INFORMATION: "n" bases represent a, t, c, g, other or unknown

<400> SEQUENCE: 31

| ggt | gct | cgt | cct | gat | gaa | gct | gta | tca | tgg | gga | aag | ata | cgt | ggt | ggt | 48 |
| Gly | Ala | Arg | Pro | Asp | Glu | Ala | Val | Ser | Trp | Gly | Lys | Ile | Arg | Gly | Gly | |
| 1 | | | | 5 | | | | | 10 | | | | | 15 | | |

| gcc | aag | act | gtg | aag | gtg | cat | tgt | gat | gca | acc | att | gca | ttt | ccc | ata | 96 |
| Ala | Lys | Thr | Val | Lys | Val | His | Cys | Asp | Ala | Thr | Ile | Ala | Phe | Pro | Ile | |
| | | | 20 | | | | | 25 | | | | | 30 | | | |

| tta | gta | gct | gag | aca | ttt | gca | gct | aag | agt | aag | gaa | ttc | tcc | cag | ata | 144 |
| Leu | Val | Ala | Glu | Thr | Phe | Ala | Ala | Lys | Ser | Lys | Glu | Phe | Ser | Gln | Ile | |
| | | | 35 | | | | | 40 | | | | | 45 | | | |

| agg | tgc | caa | gtt | tgaacattga ggaagctgtc cttccgacca cacatatgaa | 196 |
| Arg | Cys | Gln | Val | |
| | | 50 | | | ttgctagctt ttgaagccaa cttgctagtg tgcagcacca tttattctgc aaaactgact    256
agagagcagg gtatattcct ctaccccgag ttagacgaca tcctgtatgg ttcaaattaa    316
ttattttct cccccttcaca ccatgttatt tagttctctt cctcttcgaa agtgaagagc    376
ttagatgttc ataggttttg aattatgttg gaggttggtg ataactgact agtcctctta    436
ccatatagat aatgtatcct tgtactatga gattttgggt gtgtttgata ccaaggaaaa    496
atgtttattt ggaaaacaat tggatttta atttaaaaaa aattgnttaa aaaaaaaaa    556
aaa                                                                559

<210> SEQ ID NO 32
<211> LENGTH: 193
<212> TYPE: PRT
<213> ORGANISM: Arabidopsis sp.
<220> FEATURE:
<223> OTHER INFORMATION: DHS

<400> SEQUENCE: 32

Gly Gly Val Glu Glu Asp Leu Ile Lys Cys Leu Ala Pro Thr Phe Lys
1               5                   10                  15

Gly Asp Phe Ser Leu Pro Gly Ala Tyr Leu Arg Ser Lys Gly Leu Asn
            20                  25                  30

Arg Ile Gly Asn Leu Leu Val Pro Asn Asp Asn Tyr Cys Lys Phe Glu
        35                  40                  45

Asp Trp Ile Ile Pro Ile Phe Asp Glu Met Leu Lys Glu Gln Lys Glu
    50                  55                  60

Glu Asn Val Leu Trp Thr Pro Ser Lys Leu Leu Ala Arg Leu Gly Lys
65                  70                  75                  80

Glu Ile Asn Asn Glu Ser Ser Tyr Leu Tyr Trp Ala Tyr Lys Met Asn
                85                  90                  95

Ile Pro Val Phe Cys Pro Gly Leu Thr Asp Gly Ser Leu Arg Asp Met
            100                 105                 110

Leu Tyr Phe His Ser Phe Arg Thr Ser Gly Leu Ile Ile Asp Val Val

```
            115                 120                 125
Gln Asp Ile Arg Ala Met Asn Gly Glu Ala Val His Ala Asn Pro Lys
        130                 135                 140

Lys Thr Gly Met Ile Ile Leu Gly Gly Leu Pro Lys His His Ile
145                 150                 155                 160

Cys Asn Ala Asn Met Met Arg Asn Gly Ala Asp Tyr Ala Val Phe Ile
                165                 170                 175

Asn Thr Gly Gln Glu Phe Asp Gly Ser Asp Ser Gly Ala Arg Pro Asp
        180                 185                 190

Glu

<210> SEQ ID NO 33
<211> LENGTH: 173
<212> TYPE: PRT
<213> ORGANISM: Dianthus sp.
<220> FEATURE:
<223> OTHER INFORMATION: DHS

<400> SEQUENCE: 33

Arg Ser Ile Lys Cys Leu Ala Pro Thr Phe Lys Gly Asp Phe Ala Leu
1               5                   10                  15

Pro Gly Ala Gln Leu Arg Ser Lys Gly Leu Asn Arg Ile Gly Asn Leu
            20                  25                  30

Leu Val Pro Asn Asp Asn Tyr Cys Lys Phe Glu Asp Trp Ile Ile Pro
        35                  40                  45

Ile Leu Asp Lys Met Leu Glu Glu Gln Ile Ser Glu Lys Ile Leu Trp
    50                  55                  60

Thr Pro Ser Lys Leu Ile Gly Arg Leu Gly Arg Glu Ile Asn Asp Glu
65                  70                  75                  80

Ser Ser Tyr Leu Tyr Trp Ala Phe Lys Asn Asn Ile Pro Val Phe Cys
                85                  90                  95

Pro Gly Leu Thr Asp Gly Ser Leu Gly Asp Met Leu Tyr Phe His Ser
            100                 105                 110

Phe Arg Asn Pro Gly Leu Ile Ile Asp Val Val Gln Asp Ile Arg Ala
        115                 120                 125

Val Asn Gly Glu Ala Val His Ala Ala Pro Arg Lys Thr Gly Met Ile
    130                 135                 140

Ile Leu Gly Gly Gly Leu Pro Lys His His Ile Cys Asn Ala Asn Met
145                 150                 155                 160

Met Arg Asn Gly Ala Asp Tyr Ala Val Phe Ile Asn Thr
                165                 170

<210> SEQ ID NO 34
<211> LENGTH: 37
<212> TYPE: PRT
<213> ORGANISM: Arabidopsis sp.
<220> FEATURE:
<223> OTHER INFORMATION: DHS

<400> SEQUENCE: 34

Ala Arg Pro Asp Glu Ala Val Ser Trp Gly Lys Ile Arg Gly Ser Ala
1               5                   10                  15

Lys Thr Val Lys Val Cys Phe Leu Ile Ser Ser His Pro Asn Leu Tyr
            20                  25                  30

Leu Thr Gln Trp Phe
        35
```

-continued

```
<210> SEQ ID NO 35
<211> LENGTH: 52
<212> TYPE: PRT
<213> ORGANISM: Lycopersicon sp.
<220> FEATURE:
<223> OTHER INFORMATION: DHS

<400> SEQUENCE: 35

Gly Ala Arg Pro Asp Glu Ala Val Ser Trp Gly Lys Ile Arg Gly Gly
 1               5                  10                  15

Ala Lys Thr Val Lys Val His Cys Asp Ala Thr Ile Ala Phe Pro Ile
            20                  25                  30

Leu Val Ala Glu Thr Phe Ala Ala Lys Ser Lys Glu Phe Ser Gln Ile
        35                  40                  45

Arg Cys Gln Val
    50
```

ARABIDOPSIS ANTISENSE DEOXYHYPUSINE SYNTHASE MOLECULE AND METHOD OF INHIBITING DEOXYHYPUSINE SYNTHASE EXPRESSION IN PLANTS

This application is a divisional application of Ser. No. 09/597,771, filed on Jun. 19, 2000, now U.S. Pat. No. 6,538,182, which is a continuation-in-part application of Ser. No. 09/348,675, filed on Jul. 6, 1999, now abandoned.

FIELD OF THE INVENTION

The present invention relates to polynucleotides which encode plant polypeptides that exhibit senescence-induced expression. The invention also relates to transgenic plants containing the polynucleotides in antisense orientation and methods for controlling programmed cell death, including senescence, in plants. More particularly, the present invention relates to a senescence induced plant deoxyhypusine synthase gene and a senescence-induced eIF-5A gene whose expressions are induced by the onset of programmed cell death, including senescence, and the use of the deoxyhypusine synthase gene and eIF-5A gene, alone or in combination, to control programmed cell death and senescence in plants.

DESCRIPTION OF THE PRIOR ART

Senescence is the terminal phase of biological development in the life of a plant. It presages death and occurs at various levels of biological organization including the whole plant, organs, flowers and fruit, tissues and individual cells.

The onset of senescence can be induced by different factors both internal and external. Senescence is a complex, highly regulated developmental stage in the life of a plant or plant tissue, such as fruit, flowers and leaves. Senescence results in the coordinated breakdown of cell membranes and macromolecules and the subsequent mobilization of metabolites to other parts of the plant.

In addition to the programmed senescence which takes place during normal plant development, death of cells and tissues and ensuing remobilization of metabolites occurs as a coordinated response to external, environmental factors. External factors that induce premature initiation of senescence, which is also referred to as necrosis or apoptosis, include environmental stresses such as temperature, drought, poor light or nutrient supply, as well as pathogen attack. Plant tissues exposed to environmental stress also produce ethylene, commonly known as stress ethylene (Buchanan-Wollaston, V., 1997, J. Exp. Botany, 48:181–199; Wright, M., 1974, Plant, 120:63–69). Ethylene is known to cause senescence in some plants.

Senescence is not a passive process, but, rather, is an actively regulated process that involves coordinated expression of specific genes. During senescence, the levels of total RNA decrease and the expression of many genes is switched off (Bate et al., 1991, J. Exper. Botany, 42, 801–11; Hensel et al., 1993, The Plant Cell, 5, 553–64). However, there is increasing evidence that the senescence process depends on de novo transcription of nuclear genes. For example, senescence is blocked by inhibitors of mRNA and protein synthesis and enucleation. Molecular studies using mRNA from senescing leaves and green leaves for in vitro translation experiments show a changed pattern of leaf protein products in senescing leaves (Thomas et al, 1992, J. Plant Physiol., 139, 403–12). With the use of differential screening and subtractive hybridization techniques, many cDNA clones representing senescence-induced genes have been identified from a range of different plants, including both monocots and dicots, such as *Arabidopsis*, maize, cucumber, asparagus, tomato, rice and potato. Identification of genes that are expressed specifically during senescence is hard evidence of the requirement for de novo transcription for senescence to proceed.

The events that take place during senescence appear to be highly coordinated to allow maximum use of the cellular components before necrosis and death occur. Complex interactions involving the perception of specific signals and the induction of cascades of gene expression must occur to regulate this process. Expression of genes encoding senescence related proteins is probably regulated via common activator proteins that are, in turn, activated directly or indirectly by hormonal signals. Little is known about the mechanisms involved in the initial signaling or subsequent co-ordination of the process.

Coordinated gene expression requires factors involved in transcription and translation, including initiation factors. Translation initiation factor genes have been isolated and characterized in a variety of organisms, including plants. Eukaryotic translation initiation factor 5A (eIF-5A) is an essential protein factor approximately 17 KDa in size, which is involved in the initiation of eukaryotic cellular protein synthesis. It is characterized by the presence of hypusine [N-(4-amino-2-hydroxybutyl)lysine], a unique modified amino acid, known to be present only in eIF-5A. Hypusine is formed post-translationally via the transfer and hydroxylation of the butylamino group from the polyamine, spermidine, to the side chain amino group of a specific lysine residue in eIF-5A. Activation of eIF-5A involves transfer of the butylamine residue of spermidine to the lysine of eIF-5A, forming hypusine and activating eIF-5A. In eukaryotes, deoxyhypusine synthase (DHS) mediates the post-translational synthesis of hypusine in eIF-5A. A corresponding DHS gene has not been identified in plants, however, it is known that plant eIF-5A contains hypusine. The hypusine modification has been shown to be essential for eIF-5A activity in vitro using a methionyl-puromycin assay.

Hypusine is uniquely present in eIF-5A and is found in all eukaryotes, some archaebacteria (which appear to be related to eukaryota), but not in eubacteria. Moreover, the amino acid sequence of eIF-5A is highly conserved, especially in the region surrounding the hypusine residue, suggesting that eIF-5A and its activating protein, deoxyhypusine synthase, execute fundamentally important steps in eukaryotic cell physiology (Joe et al., JBC, 270:22386–22392, 1995). eIF-5A has been cloned from human, alfalfa, slime mold, *Neurospora crassa*, tobacco and yeast. It was originally identified as a general translation initiation factor based on its isolation from ribosomes of rabbit reticulocyte lysates and its in vitro activity in stimulating methionine-puromycin synthesis. However, more recent data indicate that eIF-5A is not a translation initiation factor for global protein synthesis, but rather serves to facilitate the translation of specific subsets of mRNA populations. For example, there is strong evidence from experiments with animal cells and yeast that one or more isoforms of eIF-5A play an essential role in mediating the translation of a subset of mRNAs involved in cell proliferation. There are two isoforms in yeast, and if both genes are silenced the cells are unable to divide (Park et al., Biol. Signals, 6:115–123, 1997). Similarly, silencing the expression of yeast deoxyhypusine synthase, which activates eIF-5A, blocks cell division. Indeed, inhibitors of deoxyhypusine synthase have been developed that are likely to have importance in the therapy of hyperproliferative conditions (Wolff, et al., JBC, 272:15865–15871, 1997). Other studies have indicated that another isoform of eIF-5A is essential for Rev function in HIV-1 replication or Rex function in HTLV V replication (Park, et al., Biol. Signals, 6:115–123, 1997). There are also at least two expressed eIF-5A genes in tobacco. Gene-specific probes indicate that although they are both expressed in all tissues examined, each gene has a distinctive expression pattern, presumably regulating the translation of specific transcripts (Chamot, et al., Nuc. Acids Res., 20:625–669, 1992).

Deoxyhypusine synthase has been purified from rat testis, HeLa cells, *Neurospora crassa* and yeast. The amino acid sequence of deoxyhypusine synthase is highly conserved, and the enzymes from different species share similar physical and catalytic properties and display cross-species reactivities with heterologous eIF-5A precursors (Park, et al., 6 Biol. Signals, 6:115–123, 1997).

Plant polyamines have been implicated in a wide variety of physiological effects including floral induction, embryogenesis, pathogen resistance, cell growth, differentiation and division (Evans et al., 1989, Annu. Rev. Plant Physiol. Plant Mol. Biol., 40, 235–269; and Galston, et al., 1990, Plant Physiol., 94, 406–10). It has been suggested that eIF-5A is the intermediary through which polyamines exert their effects (Chamot et al., 1992, Nuc. Acids Res., 20(4), 665–69).

Two genes encoding isoforms of eIF-5A from *Nicotiana* have been identified (NeIF-5A1 and NeIF-5A2) (Chamot et al., 1992, Nuc. Acids Res., 20(4), 665–69). The genes were shown to be very similar. However, they display differential patterns of expression. One gene appears to be constitutively expressed at the mRNA level, while the expression pattern of the other correlates with the presence or absence of photosynthetic activity. Based on gene structure and genomic Southern mapping it has been suggested that there is a multigene family of NeIF-5A genes in tobacco. It is likely that there is an eIF-5A isoform that regulates translation of a subset of senescence/necrosis specific mRNA transcripts.

Presently, there is no widely applicable method for controlling the onset of programmed cell death (including senescence) caused by either internal or external, e.g., environmental stress, factors. It is, therefore, of interest to develop senescence modulating technologies that are applicable to all types of plants and that are effective at the earliest stages in the cascade of events leading to senescence.

SUMMARY OF THE INVENTION

This invention is based on the discovery and cloning of a full length cDNA clone encoding a tomato senescence-induced deoxyhypusine synthase (DHS), as well as full length senescence-induced DHS cDNA clones from *Arabidopsis* leaf and carnation petal. The nucleotide sequences and corresponding amino acid sequences are disclosed herein.

The invention is also based, in part, on the discovery and cloning of full length cDNA clones encoding a senescence-induced eIF-5A gene from tomato, *Arabidopsis* and carnation. The nucleotide sequence and corresponding amino acid sequence of each of the eIF-5A cDNA clones are disclosed herein.

The present invention provides a method for genetic modification of plants to control the onset of senescence, either age-related senescence or environmental stress-induced senescence. The senescence-induced DHS nucleotide sequences of the invention, fragments thereof, or combinations of such fragments, are introduced into a plant cell in reverse orientation to inhibit expression of the endogenous senescence-induced DHS gene, thereby reducing the level of endogenous senescence-induced DHS protein, and reducing and/or preventing activation of eIF-5A and ensuing expression of the genes that mediate senescence.

In another aspect of the invention, the senescence-induced eIF-5A nucleotide sequences of the invention, fragments thereof, or combinations of such fragments, are introduced into a plant cell in reverse orientation to inhibit expression of the endogenous senescence-induced eIF-5A gene, and thereby reduce the level of endogenous senescence-induced eIF-5A protein, and reduce and/or prevent ensuing expression of the genes that mediate senescence. Alternatively, both DHS sequences and eIF-5A sequences can be used together to reduce the levels of endogenous DHS and eIF-5A proteins In yet another aspect, the present invention is directed to a method for genetic modification of plants to control the onset of senescence, either age-related senescence or environmental stress-induced senescence via the introduction into a plant cell of a combination of senescence-induced eIF-5A nucleotide sequences of the invention and senescence-induced DHS nucleotide sequences of the invention in reverse orientation to inhibit expression of the endogenous senescence-induced eIF-5A gene and senescence-induced DHS gene, thereby reducing the level of endogenous senescence-induced DHS protein, and reducing and/or preventing activation of eIF-5A and ensuing expression of the genes that mediate senescence.

Using the methods of the invention, transgenic plants are generated and monitored for growth, development and either natural or prematurely-induced senescence. Plants or detached parts of plants (e.g., cuttings, flowers, vegetables, fruits, seeds or leaves) exhibiting prolonged life or shelf life, (e.g., extended life of flowers, reduced fruit or vegetable spoilage, enhanced biomass, increased seed yield, reduced seed aging and/or reduced yellowing of leaves) due to reduction in the level of senescence-induced DHS, senescence-induced eIF-5A or both are selected as desired products having improved properties including reduced leaf yellowing, reduced petal abscission, reduced fruit and vegetable spoilage during shipping and storage. These superior plants are propagated. Similarly, plants exhibiting increased resistance to environmental stress, e.g., decreased susceptibility to low temperature (chilling), drought, infection, etc., and/ or increased resistance to pathogens, are selected as superior products.

In one aspect, the present invention is directed to an isolated DNA molecule encoding senescence-induced DHS, wherein the DNA molecule hybridizes with SEQ ID NO:1, or a functional derivative of the isolated DNA molecule which hybridizes with SEQ ID NO:1. In one embodiment of this aspect of the invention, the isolated DNA molecule has the nucleotide sequence of SEQ ID NO:1, i.e., 100% complementarity (sequence identity) to SEQ ID NO:1.

The present invention also is directed to an isolated DNA molecule encoding senescence-induced DHS, wherein the DNA molecule hybridizes with SEQ ID NO:9, or a functional derivative of the isolated DNA molecule which hybridizes with SEQ ID NO:9. In one embodiment of this aspect of the invention, the isolated DNA molecule has the nucleotide sequence of SEQ ID NO:9, i.e., 100% complementarity (sequence identity) to SEQ ID NO:9.

The present invention also is directed to an isolated DNA molecule encoding senescence-induced eIF-5A, wherein the DNA molecule hybridizes with SEQ ID NO:11, SEQ ID NO:13, SEQ ID NO:15 or a functional derivative of the isolated DNA molecule which hybridizes with SEQ ID NO:11, SEQ ID NO:13, SEQ ID NO:15. In one embodiment of this aspect of the invention, the isolated DNA molecule has the nucleotide sequence of SEQ ID NO:11, SEQ ID NO:13, or SEQ ID NO:15, i.e., 100% complementarity (sequence identity) to SEQ ID NO:11, SEQ ID NO:13 or SEQ ID NO:15.

In another embodiment of the invention, there is provided an isolated protein encoded by a DNA molecule as described herein above, or a functional derivative thereof. A preferred protein has the amino acid sequence of SEQ ID NO:2, or is a functional derivative thereof. Another preferred protein has the amino acid sequence of SEQ ID NO:10, or is a functional derivative thereof. Other preferred proteins of the invention have the amino acid sequence of SEQ ID NO:12, SEQ ID NO:14 or SEQ ID NO: 16.

Also provided herein is an antisense oligonucleotide or polynucleotide encoding an RNA molecule which is complementary to a corresponding portion of an RNA transcript of a DNA molecule described herein above, wherein the oligonucleotide or polynucleotide hybridizes with the RNA transcript such that expression of endogenous senescence-induced DHS is altered. In another embodiment of this aspect of the invention, the antisense oligonucleotide or polynucleotide is an RNA molecule that hybridizes to a corresponding portion of an RNA transcript of a DNA molecule described herein above, such that expression of endogenous senescence-induced eIF-5A is altered. The antisense oligonucleotide or polynucleotide can be full length or preferably has about six to about 100 nucleotides.

The antisense oligonucleotide or polynucleotide may be substantially complementary to a corresponding portion of one strand of a DNA molecule encoding senescence-induced DHS, wherein the DNA molecule encoding senescence-induced DHS hybridizes with SEQ ID NO:1, SEQ ID NO: 5, SEQ ID NO: 9, or with a combination thereof, or is substantially complementary to at least a corresponding portion of an RNA sequence encoded by the DNA molecule encoding senescence-induced DHS. In one embodiment of the invention, the antisense oligonucleotide or polynucleotide is substantially complementary to a corresponding portion of one strand of the nucleotide sequence SEQ ID NO:1, SEQ ID NO:5, SEQ ID NO:9 or with a combination thereof, or the RNA transcript transcribed from SEQ ID NO:1, SEQ ID NO:5, SEQ ID NO:9 or with a combination thereof. In another embodiment, the antisense oligonucleotide is substantially complementary to a corresponding portion of the 5' non-coding portion or 3' portion of one strand of a DNA molecule encoding senescence-induced DHS, wherein the DNA molecule hybridizes with SEQ ID NO:1, SEQ ID NO:5, SEQ ID NO:9 or with a combination thereof.

Alternatively, the antisense oligonucleotide or polynucleotide may be substantially complementary to a corresponding portion of one strand of a DNA molecule encoding senescence-induced eIF-5A, wherein the DNA molecule encoding senescence-induced eIF-5A hybridizes with SEQ ID NO:11, SEQ ID NO:13, SEQ ID NO:15, or any combination thereof, or is substantially complementary to at least a corresponding portion of an RNA sequence transcribed from SEQ ID NO:11, SEQ ID NO:13 or SEQ ID NO:15. In one embodiment of the invention, the antisense oligonucleotide or polynucleotide is substantially complementary to a corresponding portion of one strand of the nucleotide sequence SEQ ID NO:11, SEQ ID NO:13, SEQ ID NO:15 or a combination thereof, or the RNA transcript encoded is substantially complementary to a corresponding portion of an RNA sequence encoded by a DNA molecule encoding senescence-induced eIF-5A. In another embodiment, the antisense oligonucleotide is substantially complementary to a corresponding portion of the 5' non-coding region or 3' region of one strand of a DNA molecule encoding senescence-induced eIF-5A, wherein the DNA molecule hybridizes with SEQ ID NO:11, SEQ ID NO:13, SEQ ID NO:15 or a combination thereof.

The invention is further directed to a vector for transformation of plant cells, comprising (a) an antisense oligo- or polynucleotide substantially complementary to (1) a corresponding portion of one strand of a DNA molecule encoding senescence-induced DHS, wherein the DNA molecule encoding senescence-induced DHS hybridizes with SEQ ID NO:1, SEQ ID NO:5 or SEQ ID NO:9, or (2) a corresponding portion of an RNA sequence encoded by the DNA molecule encoding senescence-induced DHS; and (b) regulatory sequences operatively linked to the antisense oligo- or polynucleotide such that the antisense oligo- or polynucleotide is expressed in a plant cell into which it is transformed.

The invention is further directed to a vector for transformation of plant cells, comprising (a) an antisense oligo- or polynucleotide substantially complementary to (1) a corresponding portion of one strand of a DNA molecule encoding senescence-induced eIF-5A, wherein the DNA molecule encoding senescence-induced eIF-5A hybridizes with SEQ ID NO:11, SEQ ID NO:13, SEQ ID NO:15 or (2) a corresponding portion of an RNA sequence encoded by the DNA molecule encoding senescence-induced eIF-5A; and (b) regulatory sequences operatively linked to the antisense oligo- or polynucleotide such that the antisense oligo- or polynucleotide is expressed in a plant cell into which it is transformed.

The regulatory sequences include a promoter functional in the transformed plant cell, which promoter may be inducible or constitutive. Optionally, the regulatory sequences include a polyadenylation signal.

The invention also provides a plant cell transformed with a vector or combination of vectors as described above, a plantlet or mature plant generated from such a cell, or a plant part of such a plantlet or plant.

The present invention is further directed to a method of producing a plant having a reduced level of senescence-induced DHS, senescence-induced eIF-5A or both compared to an unmodified plant, comprising:

(1) transforming a plant with a vector or combination of vectors as described above;

(2) allowing the plant to grow to at least a plantlet stage;

(3) assaying the transformed plant or plantlet for altered senescence-induced DHS activity and/or eIF-5A activity and/or altered senescence and/or altered environmental stress-induced senescence and/or pathogen-induced senescence and/or ethylene-induced senescence; and (4) selecting and growing a plant having altered senescence-induced DHS activity and/or reduced eIF-5A and/or altered senescence and/or altered environmental stress-induced senescence and/or altered pathogen-induced senescence and/or ethylene-induced senescence compared to a non-transformed plant.

Plants produced as above, or progeny, hybrids, clones or plant parts preferably exhibit reduced senescence-induced DHS expression, reduced senescence-induced eIF-5A activity, or both and delayed senescence and/or delayed stress-induced senescence and/or pathogen-induced senescence and/or ethylene-induced senescence.

This invention is further directed to a method of inhibiting expression of endogenous senescence-induced DHS in a plant cell, said method comprising:

(1) integrating into the genome of a plant a vector comprising (A) an antisense oligo- or polynucleotide complementary to (I) at least a portion of one strand of a DNA molecule encoding endogenous senescence-induced DHS, wherein the DNA molecule encoding the endogenous senescence-induced DHS hybridizes with SEQ ID NO:1, SEQ ID NO:5 and/or SEQ ID NO.9, or (ii) at least a portion of an RNA sequence encoded by the endogenous senescence-induced DHS gene; and (B) regulatory sequences operatively linked to the antisense oligo- or polynucleotide such that the antisense oligo- or polynucleotide is expressed; and (2) growing said plant, whereby said antisense oligo- or polynucleotide is transcribed and the transcript binds to said endogenous RNA whereby expression of said senescence-induced DHS gene is inhibited.

This invention is further directed to a method of inhibiting expression of endogenous senescence-induced eIF-5A in a plant cell, said method comprising:

(1) integrating into the genome of a plant a vector comprising (A) an antisense oligo- or polynucleotide complementary to (I) a corresponding portion of one strand of a DNA molecule encoding endogenous senescence-induced eIF-5A, wherein the DNA molecule encoding the endogenous senescence-induced eIF-5A hybridizes with SEQ ID NO:11, SEQ ID NO:15, SEQ ID NO:17 or a combination thereof, or (ii) at least a portion of an RNA sequence encoded by the endogenous senescence-induced eIF-5A gene; and (B) regulatory sequences operatively linked to the antisense oligo- or polynucleotide such that the antisense oligo- or polynucleotide is expressed; and (2) growing said plant, whereby said antisense oligo- or polynucleotide is transcribed and the transcript binds to said endogenous RNA whereby expression of said senescence-induced eIF-5A gene is inhibited.

BRIEF DESCRIPTION OF THE DRAWINGS

FIG. 1 depicts the nucleotide sequence of the senescence-induced tomato leaf DHS cDNA sequence (SEQ ID NO:1) and the derived amino acid sequence (SEQ ID NO. 2) obtained from a tomato leaf cDNA library.

FIG. 2A depicts the nucleotide sequence of an *Arabidopsis* DHS gene obtained by aligning the tomato DHS sequence with unidentified genomic sequences in the *Arabidopsis* gene bank (SEQ ID NO:5). The gaps between amino acid sequences are predicted introns. FIG. 2B depicts the derived *Arabidopsis* DHS amino acid sequence (SEQ ID NO:6). FIG. 2C depicts the nucleotide sequence of a 600 base pair senescence-induced *Arabidopsis* DHS cDNA obtained by PCR. FIG. 2D depicts the derived amino acid sequence of the senescence-induced *Arabidopsis* DHS cDNA fragment.

FIG. 3 is an alignment of the derived full length tomato leaf senescence-induced DHS amino acid sequence (SEQ ID NO. 2) and the derived full length *Arabidopsis* senescence-induced DHS amino acid sequence with sequences of DHS proteins of human, yeast, fungi, and Archaeobacteria. Identical amino acids among three or four of the sequences are boxed.

FIG. 6 is a Northern blot of RNA isolated from tomato flowers at different stages of development. FIG. 6A is the ethidium bromide stained gel of total RNA. Each lane contains 10 μg RNA. FIG. 6B is an autoradiograph of the Northern blot probed with $^{32}$P-dCTP-labeled full length tomato senescence-induced DHS cDNA.

FIG. 9A is the ethidium bromide stained gel of total RNA. Each lane contained 10 μg RNA. FIG. 9B is an autoradiograph of the Northern blot probed with $^{32}$P-dCTP-labelled full length tomato senescence-induced DHS cDNA. FIG. 9C shows corresponding leakage data measured as conductivity of leaf diffusates.

FIG. 10 is the carnation DHS full-length (1384 base pairs) cDNA clone nucleotide sequence (SEQ ID NO: 9), not including the PolyA tail and 5' end non-coding region. The derived amino acid sequence is shown below the nucleotide sequence (373 amino acids). (SEQ ID NO:10)

FIG. 13 is the nucleotide (top) (SEQ ID NO:11) and derived amino acid (bottom) (SEQ ID NO:12) sequence of the tomato fruit senescence-induced eIF-5A gene.

FIG. 14 is the nucleotide (top) (SEQ ID NO:13) and derived amino acid (bottom) (SEQ ID NO:14) sequence of the carnation senescence-induced eIF-5A gene.

FIG. 15 is the nucleotide (top) (SEQ ID NO:15) and derived amino acid (bottom) (SEQ ID NO:16) sequence of the *Arabidopsis* senescence-induced eIF-5A gene.

FIG. 36 is the nucleotide (top) (SEQ ID NO:30) and derived amino acid (bottom) sequence of the 3'-end of the *Arabidopsis* senescence-induced DHS gene used in antisense orientation to to transform plants.

FIG. 37 is the nucleotide (top) (SEQ ID NO:31) and derived amino acid (bottom) sequence of the 3'-end of the tomato senescence-induced DHS gene used in antisense orientation to transform plants.

FIG. 38 is the nucleotide (top) (SEQ ID NO:26) and derived amino acid (bottom) sequence of a 600 base pair *Arabidopsis* senescence-induced DHS probe used to isolate the full-length *Arabidopsis* gene.

FIG. 39 is the nucleotide (top) (SEQ ID NO:27) and derived amino acid (bottom) sequence of the 483 base pair carnation senescence-induced DHS probe used to isolate the full-length carnation gene.

DETAILED DESCRIPTION OF THE INVENTION

Figure 4:
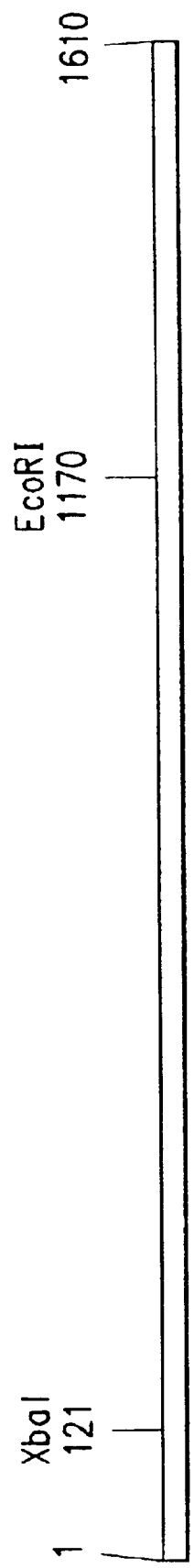
FIG. 4 is a restriction map of the tomato DHS cDNA.

Methods and compositions are provided for altering the expression of senescence-induced DHS gene(s), senescence-induced eIF-5A gene(s) or both in plant cells. Alteration of expression of senescence-induced DHS and senescence-induced eIF-5A, either alone or in combination, in plants results in delayed onset of senescence and improved resistance to environmental stress and pathogens, thus extending the plant shelf-life and/or growth period.

A full length cDNA sequence encoding a tomato DHS gene exhibiting senescence-induced expression has been isolated by reverse transcriptase mediated polymerase chain reaction (RT-PCR) using RNA isolated from chill-injured tomato leaves as a template and using the RT-PCR product to screen a chill-injured, sorbitol-treated tomato leaf cDNA library. Polynucleotide probes corresponding to selected regions of the isolated tomato leaf cDNA sequence as well as the full length tomato leaf cDNA were used to determine the presence of mRNA encoding the DHS gene in environmentally stressed (chilled) tomato leaves, (dehydrated) sorbitol-treated tomato leaves, ripening tomato fruit and senescing tomato blossoms.

Primers designed from an *Arabidopsis* DHS genomic clone were used to generate a polymerase chain reaction (PCR) product using a senescing *Arabidopsis* leaf cDNA library as template. The *Arabidopsis* nucleotide sequence has 73% nucleotide sequence identity and 81% amino acid sequence identity with the corresponding sequence of the senescence-induced tomato DHS.

The senescence-induced tomato DHS gene of the present invention was isolated by using RT-PCR. The upstream primer used to isolate the tomato DHS gene is a 24 nucleotide primer: 5' AG TCT AGA AGG TGC TCG TCC TGA T 3' (SEQ ID NO. 3); the downstream primer contains 34 nucleotides: 5' G ACT GCA GTC GAC ATC GAT (T)$_{15}$ 3' (SEQ ID NO. 4). Using 100 pmol of the downstream primer, a first strand of cDNA was isolated using standard RT-PCR. The first strand was then used as template in a RT-PCR, using both the upstream and downstream primers. Separation of the RT-PCR products on an agarose gel revealed the presence of three distinct bands ranging in size from 1.5 kb to 600 bp. The three fragments were subcloned into the plasmid vector, pBluescript™ (Stratagene Cloning Systems, LaJolla, Calif.) using XbaI and SalI cloning sites present in the upstream and downstream primers, respectively, and sequenced. The sequences of the fragments were compared and aligned with sequences present in the GeneBank database. The results showed the 1.5 kb and 1 kb fragments to be tomato DHS sequence. The 600 bp fragment also aligned with human, yeast and Neurospora DHS sequences.

The 600 bp RT-PCR fragment was used to screen a tomato (cv. Match F1 hybrid) cDNA library made from RNA obtained from tomato leaves that had been treated with 2 M sorbitol for six hours to induce dehydration. The cDNA library was constructed using a λZap™ (Stratagene Cloning Systems, LaJolla, Calif.) cDNA library kit. Three identical positive full-length cDNA clones corresponding to the senescence-induced DHS gene were obtained and sequenced. The nucleotide sequence of the senescence-induced DHS cDNA clone is shown in SEQ ID NO:1. The cDNA clone encodes a 381 amino acid polypeptide (SEQ ID NO: 2) having a calculated molecular mass of 42.1 KDa.

Based on the expression pattern of the gene in developing and stressed tomato flowers, fruit and leaves, it is involved in senescence.

The tomato DHS cDNA sequence was aligned with unidentified genomic sequences in the *Arabidopsis thaliana* genome bank The results showed alignment with an unidentified *Arabidopsis* genomic sequence (AB107060). The alignment information was used to identify an open reading frame in the *Arabidopsis* sequence and generate predicted amino acid sequence therefrom. The resulting nucleotide and amino acid sequences of the aligned *Arabidopsis* DHS gene are designated as SEQ ID NO. 5 (FIG. 2A) and SEQ ID NO. 6, respectively.

Two primers based on short regions of the identified *Arabidopsis* DHS sequence were generated: primer 1, 5' GGTGGTGTTGAGGAAGATC 3' (SEQ ID NO. 7); and primer 2, 5' GGTGCACGCCCTGATGAAGC 3' (SEQ ID NO. 8). An *Arabidopsis* senescing leaf cDNA library was used as template for the two primers in a standard PCR. A 600 bp PCR product was isolated and sequenced and shown to have an identical sequence as that of the corresponding fragment of the genomic DHS sequence.

The full-length senescence-induced tomato DHS cDNA clone was also used to isolate full-length senescence-induced *Arabidopsis* and carnation DHS cDNA clones. The *Arabidopsis* and carnation DHS cDNA clones were isolated by screening a senescing *Arabidopsis* leaf cDNA library and a senescencing carnation petal cDNA library, respectively, using the full-length tomato DHS cDNA clone as probe. cDNA clones obtained from the cDNA libraries were then sequenced. The nucleotide sequence of the *Arabidopsis* full-length cDNA clone isolated in this manner has the same sequence as the coding region of the *Arabidopsis* genomic sequence identified as encoding *Arabidopsis* DHS by alignment with the tomato cDNA sequence. (FIG. 2A, SEQ ID NO: 5). The nucleotide sequence of the full-length carnation petal senescence-induced DHS clone and derived amino acid sequence are shown in FIG. 10 (SEQ ID NO:9 and SEQ ID NO:10, respectively).

Thus, the cDNA sequences of the invention, encoding DHS from tomato, carnation and *Arabidopsis* can be used as probe in a similar manner to isolate DHS genes from other plants, which can then be used to alter senescence in transgenic plants.

The senescence-induced DHS gene appears to be a member of a DHS gene family. Genomic Southern blot analysis of tomato leaf DNA was carried out using genomic DNA extracted from a hybrid plant. The DNA was cut with various restriction enzymes that recognize a single site within the coding region of the DHS gene or which do not recognize any sites within the open reading frame of the DHS gene. A restriction map for tomato DHS is shown in FIG. 4.

Figure 5:
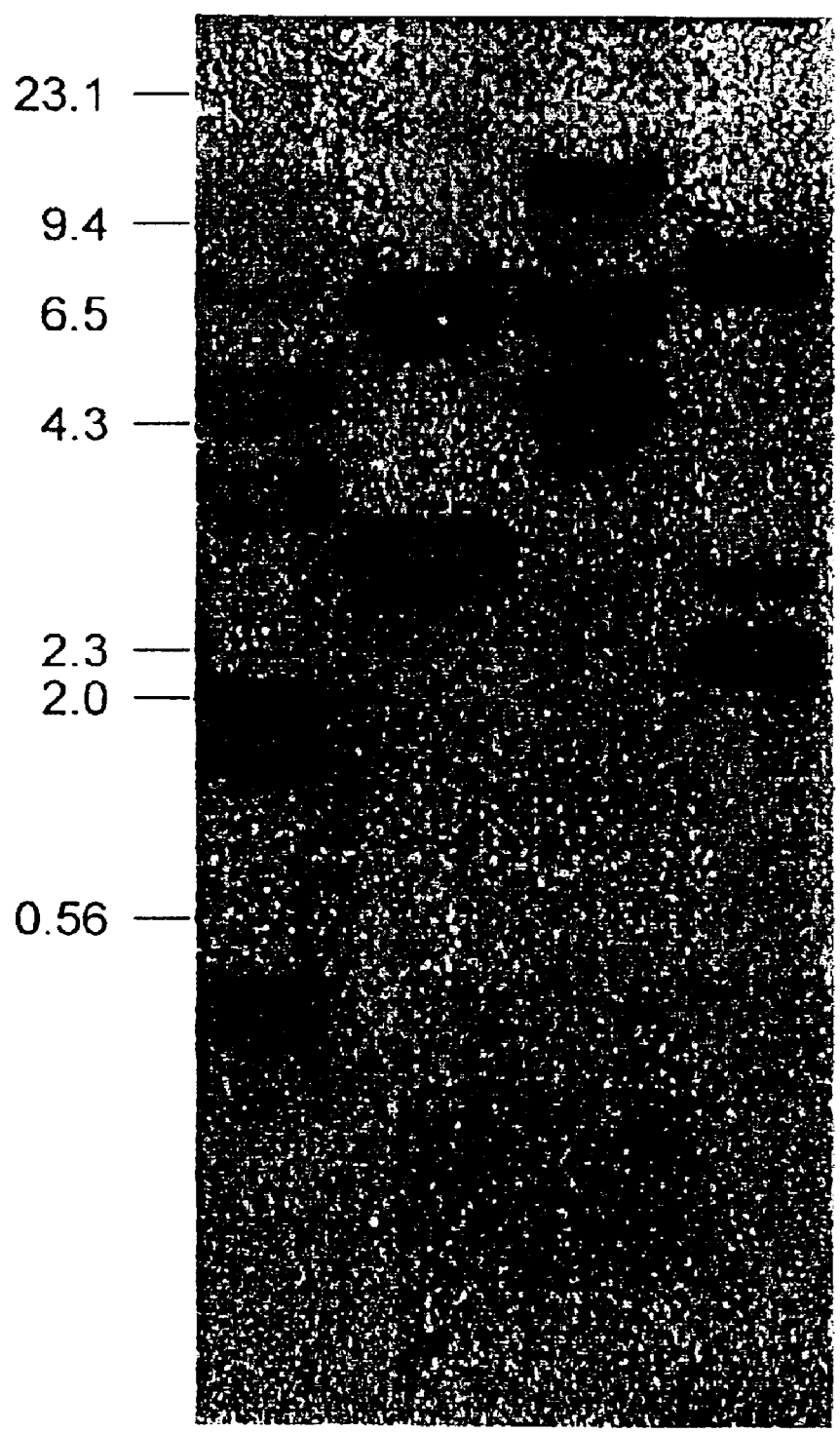
FIG. 5 is a Southern blot of genomic DNA isolated from tomato leaves and probed with $^{32}$P-dCTP-labeled full length tomato senescence-induced DHS cDNA.

Restriction enzyme digested tomato leaf genomic DNA was probed with $^{32}$P-dCTP-labeled full length tomato DHS cDNA. Hybridization under high stringency conditions revealed hybridization of the full length cDNA probe to two to three restriction fragments for each restriction enzyme digested DNA sample. Of particular note, when tomato leaf genomic DNA was digested with XbaI and EcoRI, which have restriction sites within the open reading frame of DHS (FIG. 4), more than two restriction fragments were detectable in the Southern blot (FIG. 5). Genomic DNA from cv Match F1, a hybrid variety, and the homozygous line, UCT5, yielded the same pattern of restriction fragments. These results suggest that there are two or more isoforms of the DHS gene in tomato plants. As shown in FIG. 3, the DHS gene is highly conserved across species and so it would be expected that there is a significant amount of conservation between isoforms within any species.

Figure 7:
FIG. 7 is a Northern blot of RNA isolated from tomato fruit at various stages of ripening that was probed with $^{32}$P-dCTP-labelled full length tomato senescence-induced DHS cDNA. Each lane contains 10 μg RNA.

Northern blots of tomato flower total RNA probed with the full length tomato cDNA show that the expression of the senescence-induced DHS gene is significantly induced in tomato blossoms, but expression is barely detectable in the buds (FIG. 6). Northern blot analysis of DHS expression during various developmental stages of tomato fruit demonstrate that the DHS gene is expressed at low levels in breaker and pink fruit, whereas DHS expression in red (ripe) tomato fruit is significantly enhanced (FIG. 7).

Figure 8:
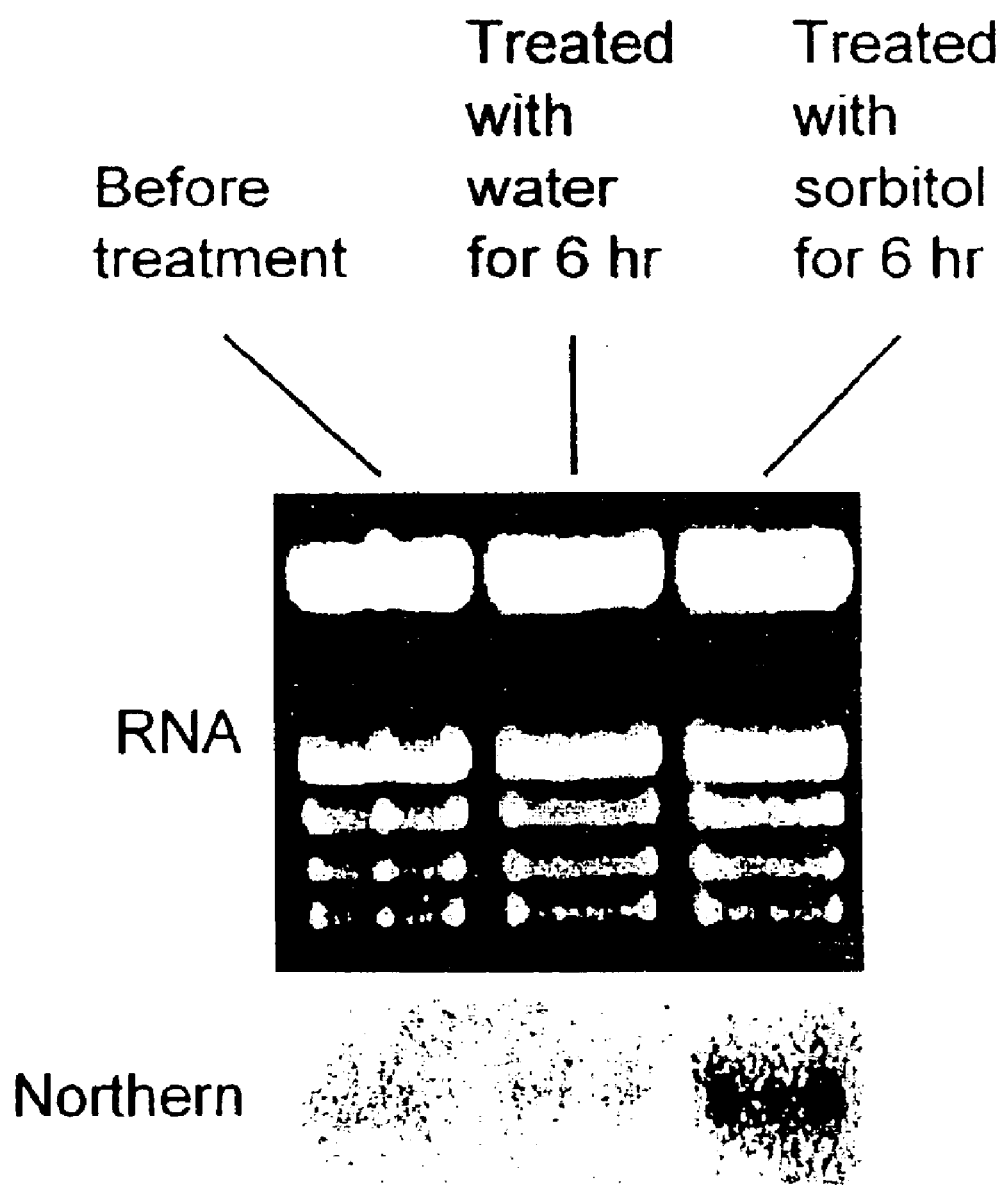
FIG. 8 is a Northern blot of RNA isolated from tomato leaves that had been drought-stressed by treatment with 2 M sorbitol for six hours. Each lane contains 10 μg RNA. The blot was probed with $^{32}$P-dCTP-labelled full length tomato senescence-induced DHS cDNA.
Figure 9:
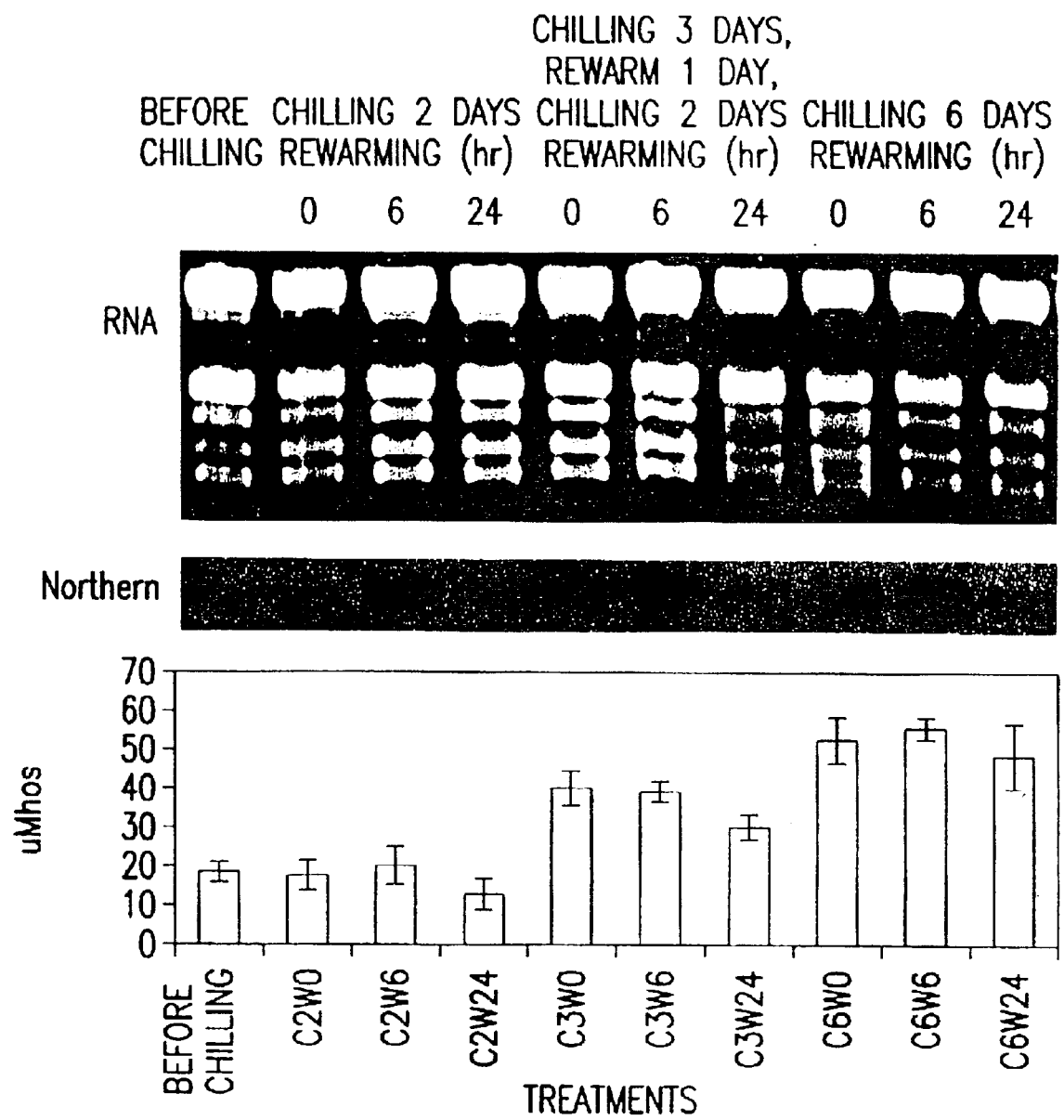
FIG. 9 is a Northern blot of RNA isolated from tomato leaves that had been exposed to chilling temperature.

Northern blot analyses also demonstrate that the senescence-induced DHS gene is induced by environmental stress conditions, e.g., dehydration (FIG. 8) and chilling (FIG. 9). Tomato leaves that had been treated with 2 M sorbitol to induce dehydration demonstrate induction of DHS expression in the dehydrated leaves compared to non-treated leaves (FIG. 8). Plants that have been exposed to chilling temperatures and returned to ambient temperature show induced expression of the senescence-induced DHS gene coincident with the development of chilling injury symptoms (e.g., leakiness) (FIG. 9). The overall pattern of gene expression in tomato plants and various plant tissues, e.g., leaves, fruit and flowers, demonstrates that the DHS gene of the invention is involved in the initiation of senescence in these plants and plant tissues.

Figure 11:
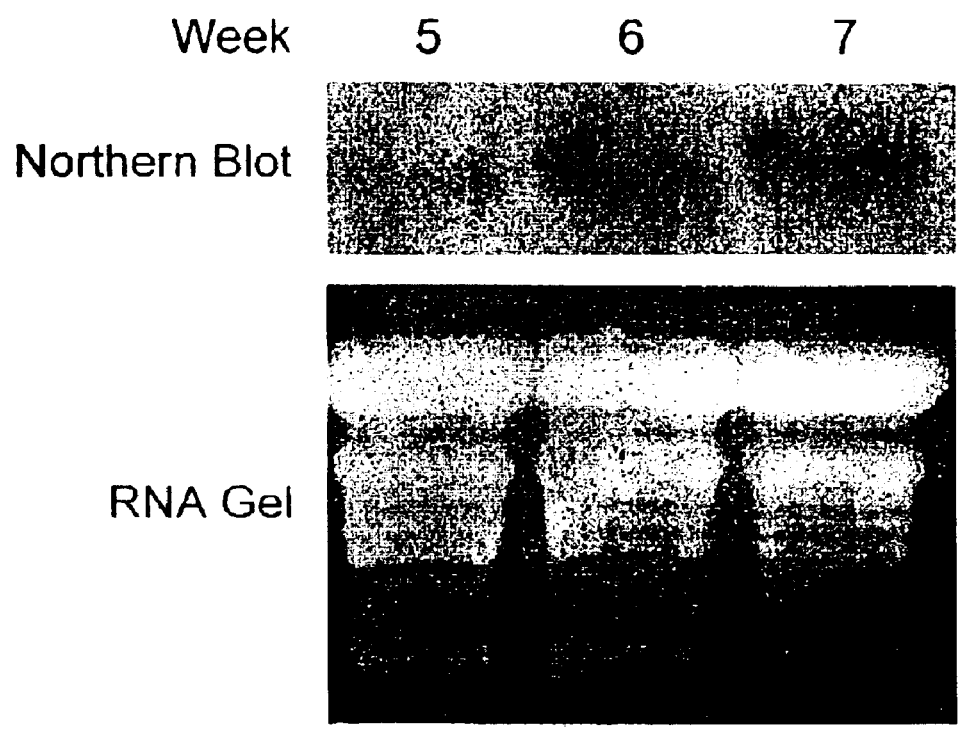
FIG. 11 is a Northern blot of total RNA from senescing *Arabidopsis* leaves probed with $^{32}$P-dCTP-labelled full-length *Arabidopsis* senescence-induced DHS cDNA. The autoradiograph is at the top, the ethidium stained gel below.

Similar results in terms of induction of DHS gene expression are observed with the onset of leaf senescence in *Arabidopsis* and petal senescence in carnation. Northern blot analyses of *Arabidopsis* leaf total RNA isolated from plants of various ages show that the expression of the senescence-induced DHS gene is not evident in young (five-week-old plants), but begins to appear at about six weeks. Expression of the DHS gene is significantly induced by seven weeks. Northern blot analysis indicates that the *Arabidopsis* DHS gene is significantly enhanced as the plant ages. (FIG. 11).

Northern blot analyses also demonstrate that the DHS gene is similarly regulated in flowering plants, such as the carnation. (FIG. 12) Northern blot analyses of total RNA isolated from petals of carnation flowers of various ages show that the expression of carnation DHS is significantly induced in petals from flowers that have symptoms of age-induced senescence such as petal inrolling, which is the first morphological manifestation of senescence, but expression is much lower in tight-bud flowers. Petals from carnation flowers that are just beginning to open have significantly more DHS expression than flowers in the tight-bud stage, and petals from flowers that are fully open also show enhanced expression of DHS.

Thus, it is expected that by substantially repressing or altering the expression of the senescence-induced DHS gene in plant tissues, deterioration and spoilage can be delayed, increasing the shelf-life of perishable fruits, flowers, and vegetables, and plants and their tissues can be rendered more stress-tolerant and pathogen resistant. This can be achieved by producing transgenic plants in which the DHS cDNA or an oligonucleotide fragment thereof is expressed in the antisense configuration in fruits, flowers, leaves and vegetables, preferably using a constitutive promoter such as the CaMV 35S promoter, or using a tissue-specific or senescence/stress-inducible promoter.

Another gene, eIF-5A, which is involved in the induction of senescence related morphological changes in plants has also been isolated and sequenced herein and like the DHS, it can be used to alter senescence and senescence-related processes in plants, preferably, by introduction in antisense orientation into plants. A full-length senescence-induced eIF-5A cDNA clone was isolated from,each of ripening tomato fruit, senescing *Arabidopsis* leaf and senescing carnation flower cDNA libraries. The nucleotide and derived amino acid sequences of each of the full length clones is shown in FIG. 13 (tomato senescence-induced eIF-5A), 14 (carnation senescence-induced eIF-5A) and 15 (*Arabidopsis senescence-induced eIF*-5A). The nucleotide sequence of each of these cDNA clones is also shown as SEQ ID NO: 11 (tomato) (FIG. 13), SEQ ID NO:13 (carnation) (FIG. 14) and SEQ ID NO:15 (*Arabidopsis*) (FIG. 15). The derived amino acid sequence of each of the genes is shown as SEQ ID NO:12 (FIG. 13), SEQ ID NO:14 (FIG. 14) and SEQ ID NO:16 (FIG. 15), respectively.

As is the case with the DHS gene sequences described herein, the eIF-5A sequence of the present invention can be used to isolate eIF-5A genes from other plants. The isolated eIF-5A sequences can be used to alter senescence and senescence-related processes in plants. Isolation of eIF-5A sequences from plants can be achieved using art known methods, based on sequences similarities of at least about 70% across species.

Figure 17:
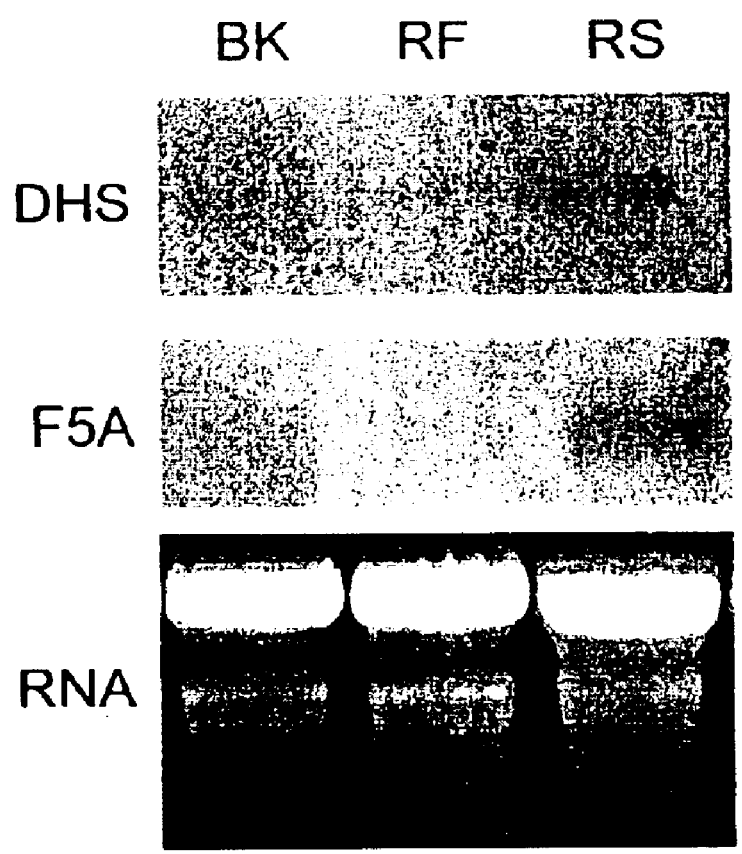
FIG. 17 is a Northern blot of total RNA isolated from tomato fruit at breaker (BK), red-firm (RF) and red-soft (RS) stages of development. The blot was probed with $^{32}$P-dCTP-labelled full-length senescence-induced DHS cDNA and full-length senescence-induced eIF-5A. DHS and eIF-5A are up-regulated in parallel in red-soft fruit coincident with fruit ripening. The autoradiograph is at the top, the ethidium stained gel below.
Figure 18:
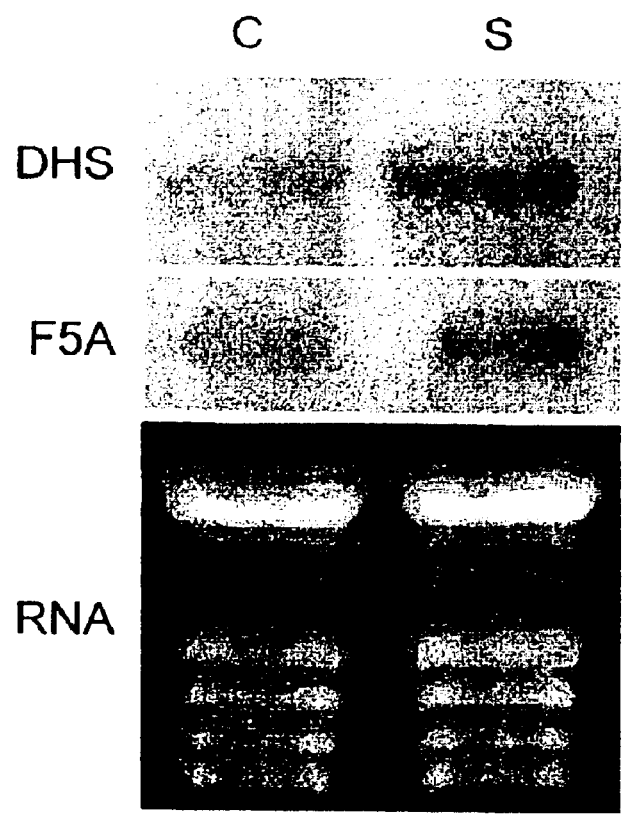
FIG. 18 is a Northern blot of total RNA isolated from leaves of tomato that were treated with sorbitol to induce drought stress. C is control; S is sorbitol treated. The blot was probed with $^{32}$P-dCTP-labelled full-length senescence-induced DHS cDNA and full-length senescence-induced eIF-5A. Both eIF-5A and DHS are up-regulated in response to drought stress. The autoradiograph is at the top, the ethidium stained gel below.
Figure 19:
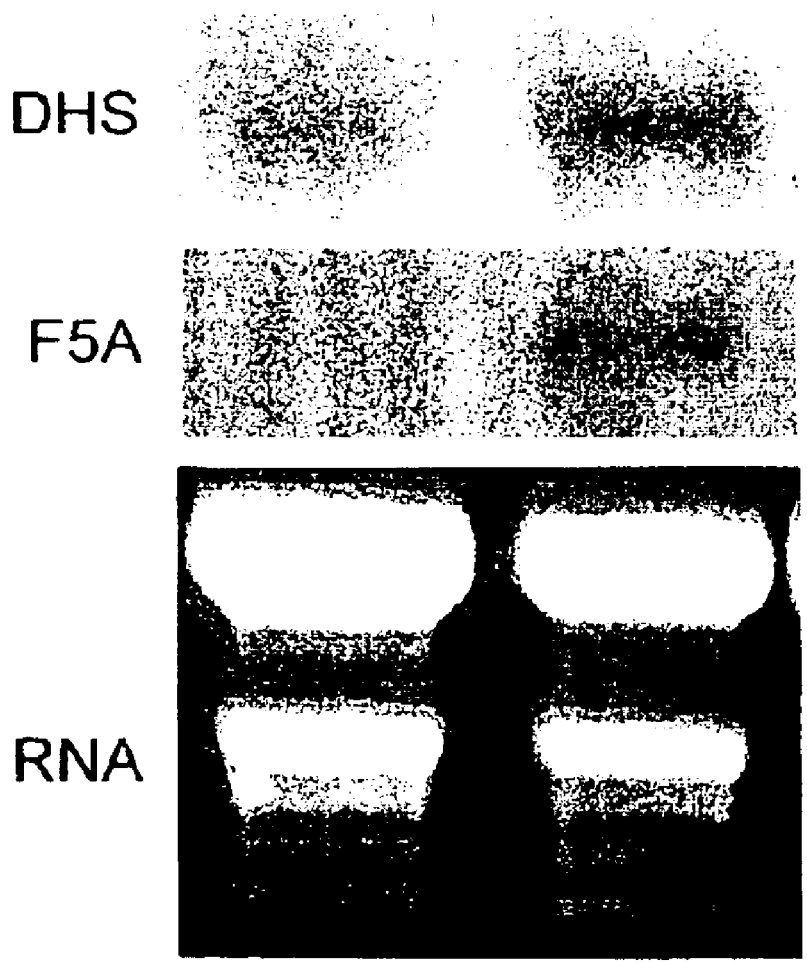
FIG. 19 is a Northern blot of total RNA isolated from flower buds and open senescing flowers of tomato plants. The blot was probed with $^{32}$P-dCTP-labelled full-length senescence-induced DHS cDNA and full-length senescence-induced eIF-5A. Both eIF-5A and DHS are up-regulated in open/senescing flowers. The autoradiograph is at the top, the ethidium stained gel below.

Parallel induction of eIF-5A and DHS occurs in plants during senescence. Northern blot analyses demonstrate that eIF-5A is upregulated in parallel with DHS at the onset of both natural and stress-induced senescence. (FIGS. 16 through 20) For example, Northern blot analyses of total RNA isolated from leaves of *Arabidopsis* plants at various ages demonstrate that from the time leaf senescence is evident in the plant the expression of eIF-5A is induced and expression is significantly enhanced as senescence progresses. In fruit bearing plants, such as tomato, eIF-5A and DHS are upregulated in parallel in red-soft fruit coincident with the onset of fruit softening and spoilage. (FIG. 17)

Figure 20:
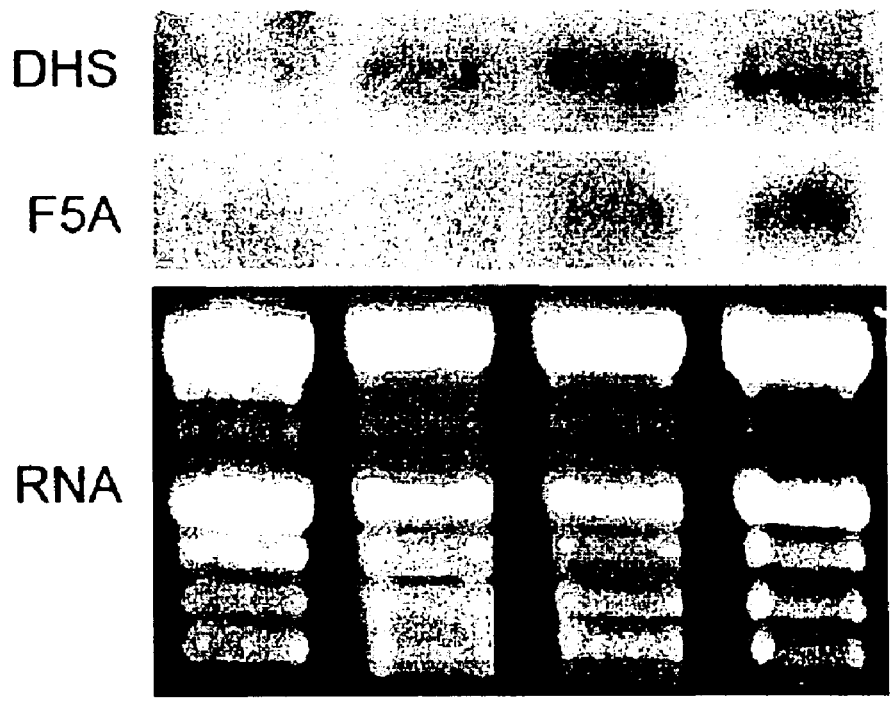
FIG. 20 is a Northern blot of total RNA isolated from chill-injured tomato leaves. The blot was probed with $^{32}$P-dCTP-labelled full-length senescence-induced DHS cDNA and full-length senescence-induced eIF-5A. Both eIF-5A and DHS are up-regulated with the development of chilling injury during rewarming The autoradiograph is at the top, the ethidium stained gel below.
Figure 21:
FIG. 21 is a photograph of 3.1 week old *Arabidopsis* wild-type (left) and transgenic plants expressing the 3'-end of the senescence DHS gene (sequence shown in FIG. 36) in antisense orientation showing increased leaf size in the transgenic plants.
Figure 22:
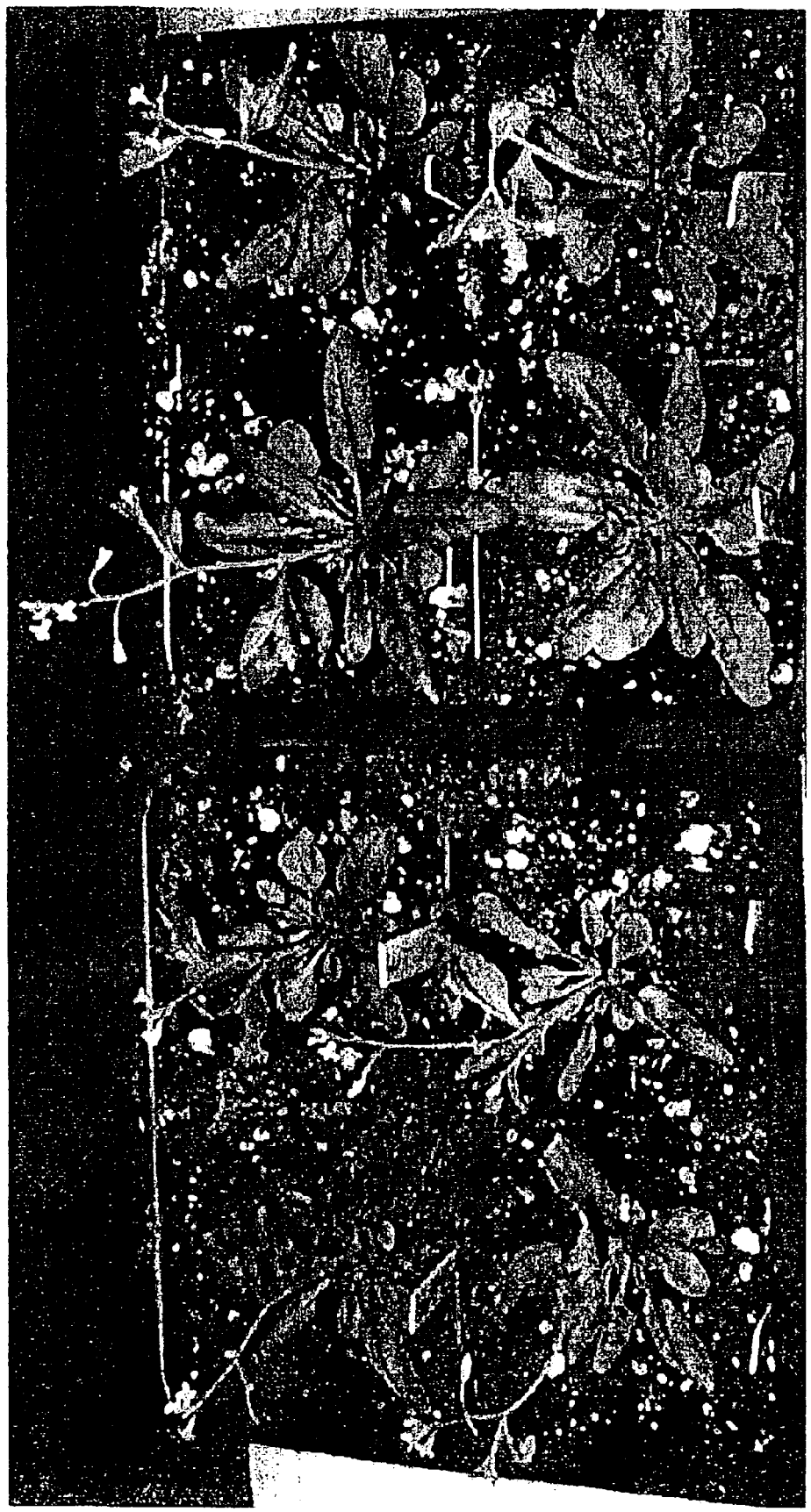
FIG. 22 is a photograph of 4.6 week old *Arabidopsis* wild-type (left) and transgenic plants expressing the 3'-end of the senescence DHS gene (sequence shown in FIG. 36) in antisense orientation showing increased leaf size in the transgenic plants.
Figure 23:
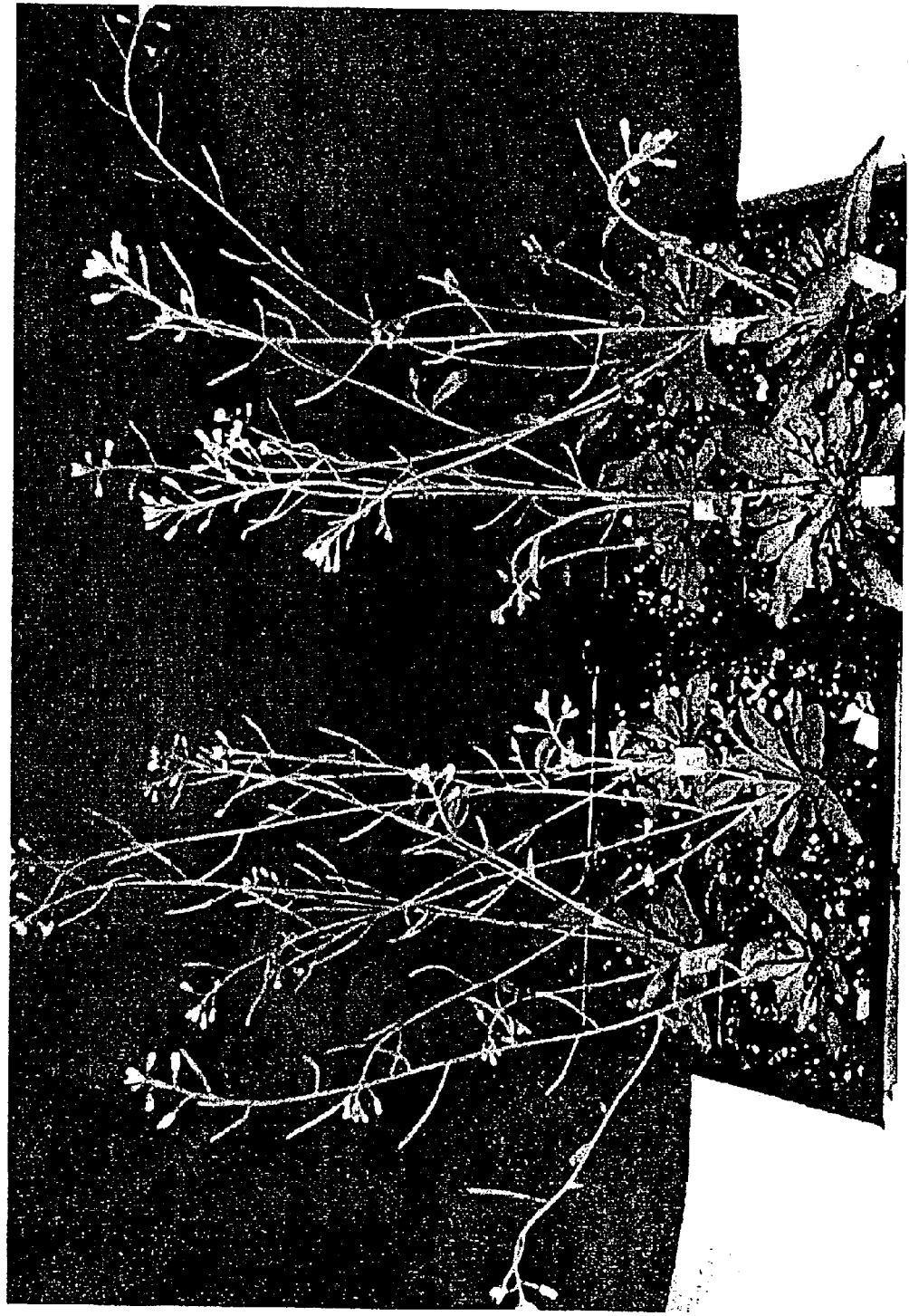
FIG. 23 is a photograph of 5.6 week old *Arabidopsis* wild-type (left) and transgenic plants expressing the 3'-end of the senescence DHS gene (sequence shown in FIG. 36) in antisense orientation showing increased leaf size in the transgenic plants.
Figure 24:
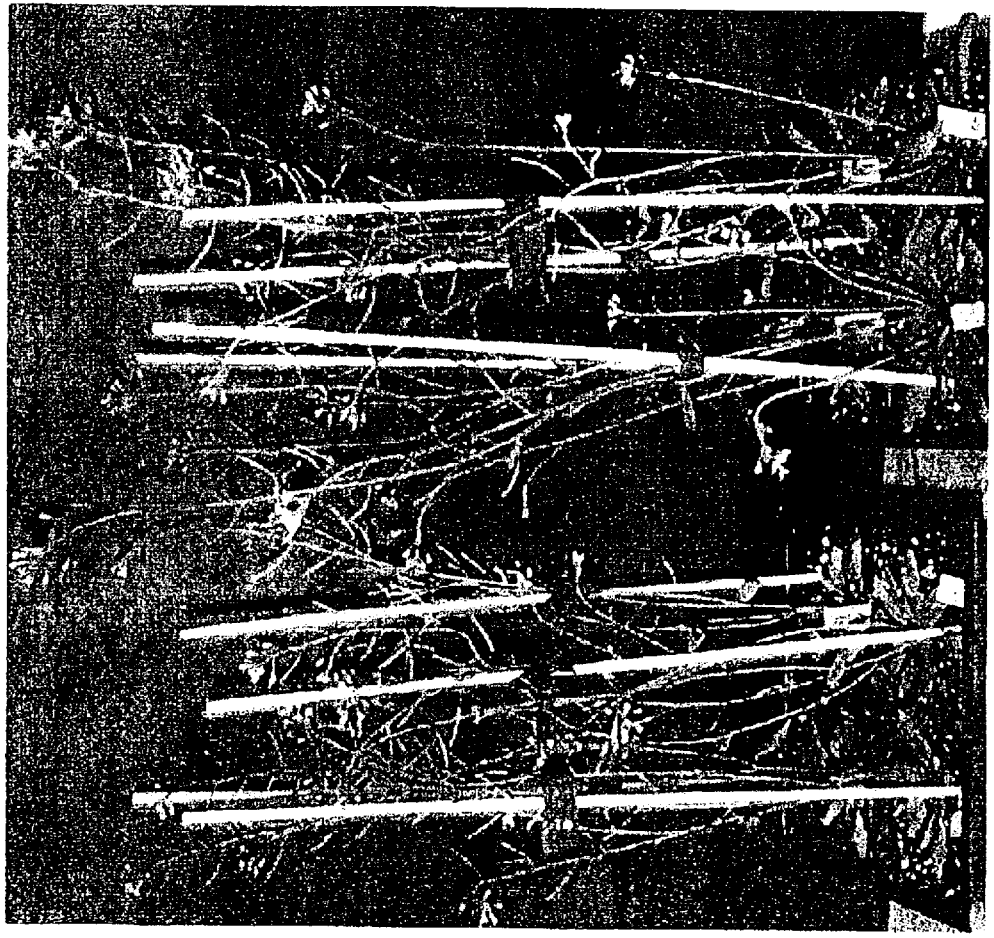
FIG. 24 is a photograph of 6.1 week old *Arabidopsis* wild-type (left) and transgenic plants expressing the 3'-end of the senescence DHS gene (sequence shown in FIG. 36) in antisense orientation showing increased size of transgenic plants.

Northern blot analysis also demonstrates that eIF-5A and DHS are upregulated in parallel in plants in response to environmantal stress, such as drought (FIG. 18) and chilling injury (FIG. 20). Similarly, in flowering plants, eIF-5A and DHS are upregulated in parallel in open flowers and expression of both genes continues to be enhanced through the later stages of flowering.

The cloned senescence-induced DHS gene, fragment(s) thereof, or cloned senescence-induced eIF-5A gene or fragment(s) thereof, or combinations of eIF-5A and DHS sequences, when introduced in reverse orientation (antisense) under control of a constitutive promoter, such as the fig wart mosaic virus 35S promoter, cauliflower mosaic virus promoter CaMV35S, double 35S promoter or MAS promoter, can be used to genetically modify plants and alter senescence in the modified plants. Selected antisense sequences from other plants which share sufficient sequence identity with the tomato, *Arabidopsis* or carnation senescence-induced DHS genes or senscence-induced eIF-5A genes can be used to achieve similar genetic modification. One result of the genetic modification is a reduction in the amount of endogenous translatable senescence-induced DHS-encoding mRNA, eIF-5A-encoding mRNA or both. Consequently, the amount of senescence-induced DHS and/ or senescence-induced eIF-5A produced in the plant cells is reduced, thereby reducing the amount of activated eIF-5A, which in turn reduces translation of senescence induced proteins, including senescence-induced lipase, senescence-induced proteases and senescence-induced nucleases. Senescence is thus inhibited or delayed, since de novo protein synthesis is required for the onset of senescence.

For example, *Arabidopsis* plants transformed with vectors that express either the full-length or 3'-region of the *Arabidopsis* senescence-induced DHS gene (SEQ ID NO:26) (FIG. 38) in antisense orientation, under regulation of a double 35S promoter exhibit increased biomass, e.g., larger leaf size and overall larger plant growth throughout all stages of growth, and delayed leaf senescence in comparison to control plants as shown in FIGS. 21 through 24.

Figure 25:
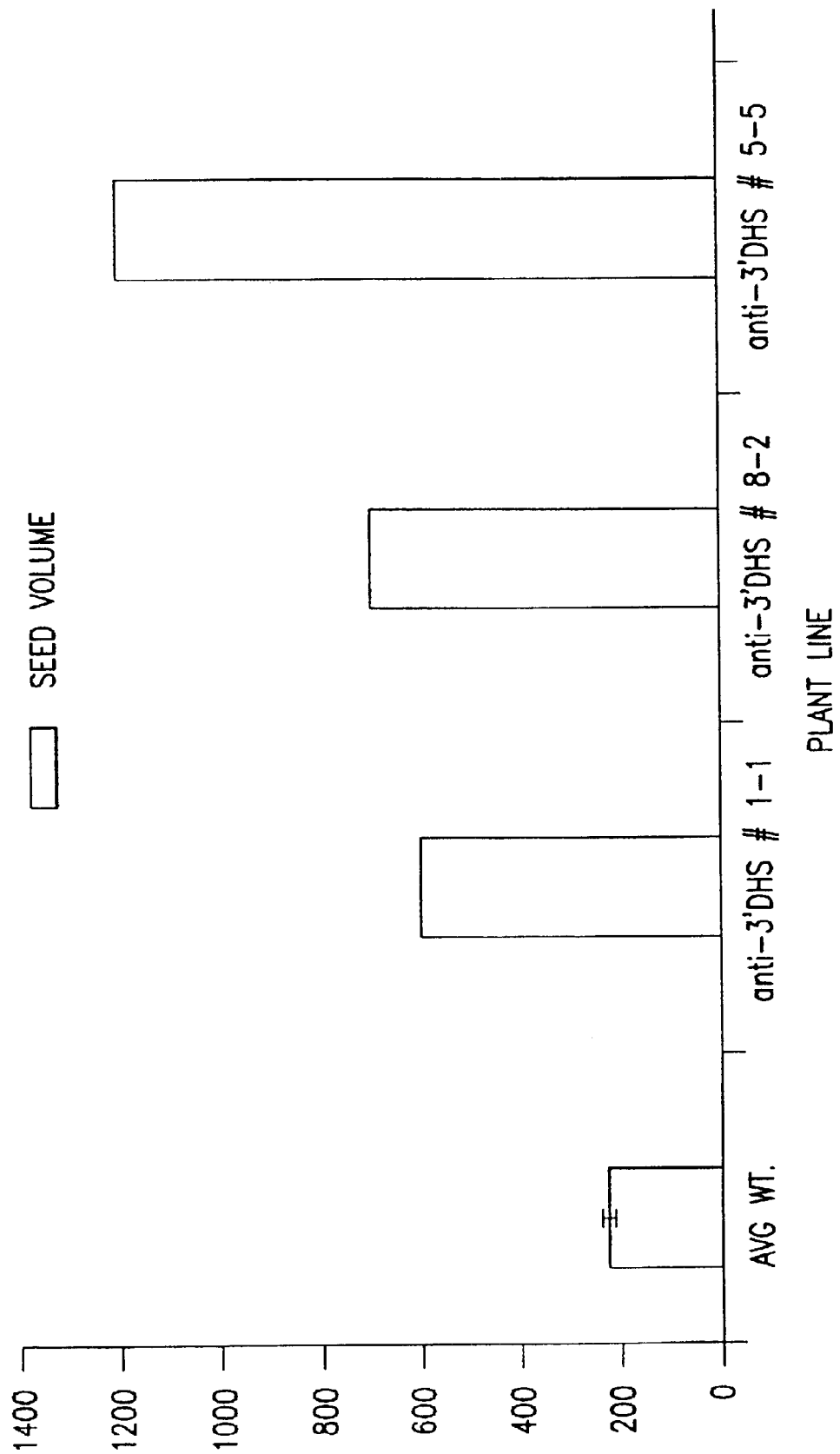
FIG. 25 is a graph showing the increase in seed yield from three $T_1$ transgenic *Arabidopsis* plant lines expressing the senescence-induced DHS gene in antisense orientation. Seed yield is expressed as volume of seed. SE for n=30 is shown for wild-type plants.

The effect of reduced expression of the senescence-induced DHS gene brought about by expressing either the full-length or 3' coding region of the *Arabidopsis* senescence-induced DHS gene in antisense orientation in transgenic *Arabidopsis* plants is also seen as an increase in seed yield in the transformed plants. *Arabidopsis* plant lines expressing the antisense 3' non-coding region of the *Arabidopsis* senescence-induced DHS gene produce up to six times more seed than wild type plants. (FIG. 25)

Figure 26:
FIG. 26 is a photograph of transgenic tomato plants expressing the 3'-end of the senescence DHS gene (sequence shown in FIG. 36) in antisense orientation (left) and wild-type plants (right) showing increased leaf size and increased plant size in the transgenic plants. The photograph was taken 18 days after transfer of the plantlets to soil.
Figure 27:
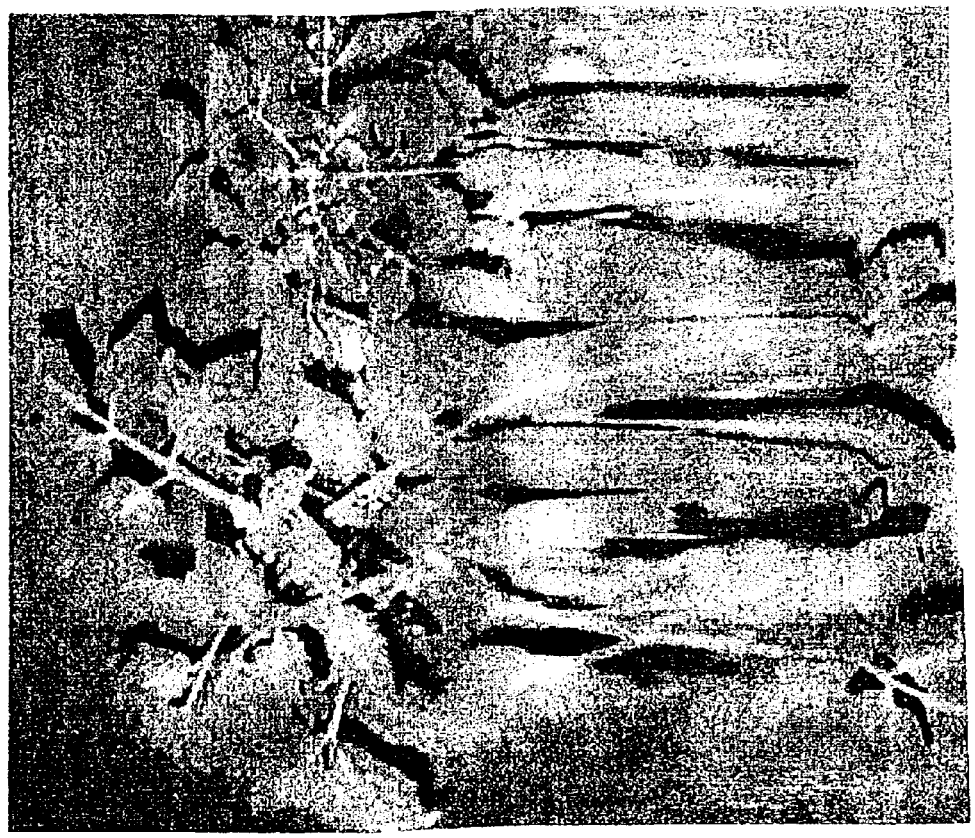
FIG. 27 is a photograph of transgenic tomato plants expressing the 3'-end of the senescence DHS gene (sequence shown in FIG. 36) in antisense orientation (left) and wild-type plants (right) showing increased leaf size and increased plant size in the transgenic plants. The photograph was taken 32 days after transfer of the plantlets to soil.
Figure 28:
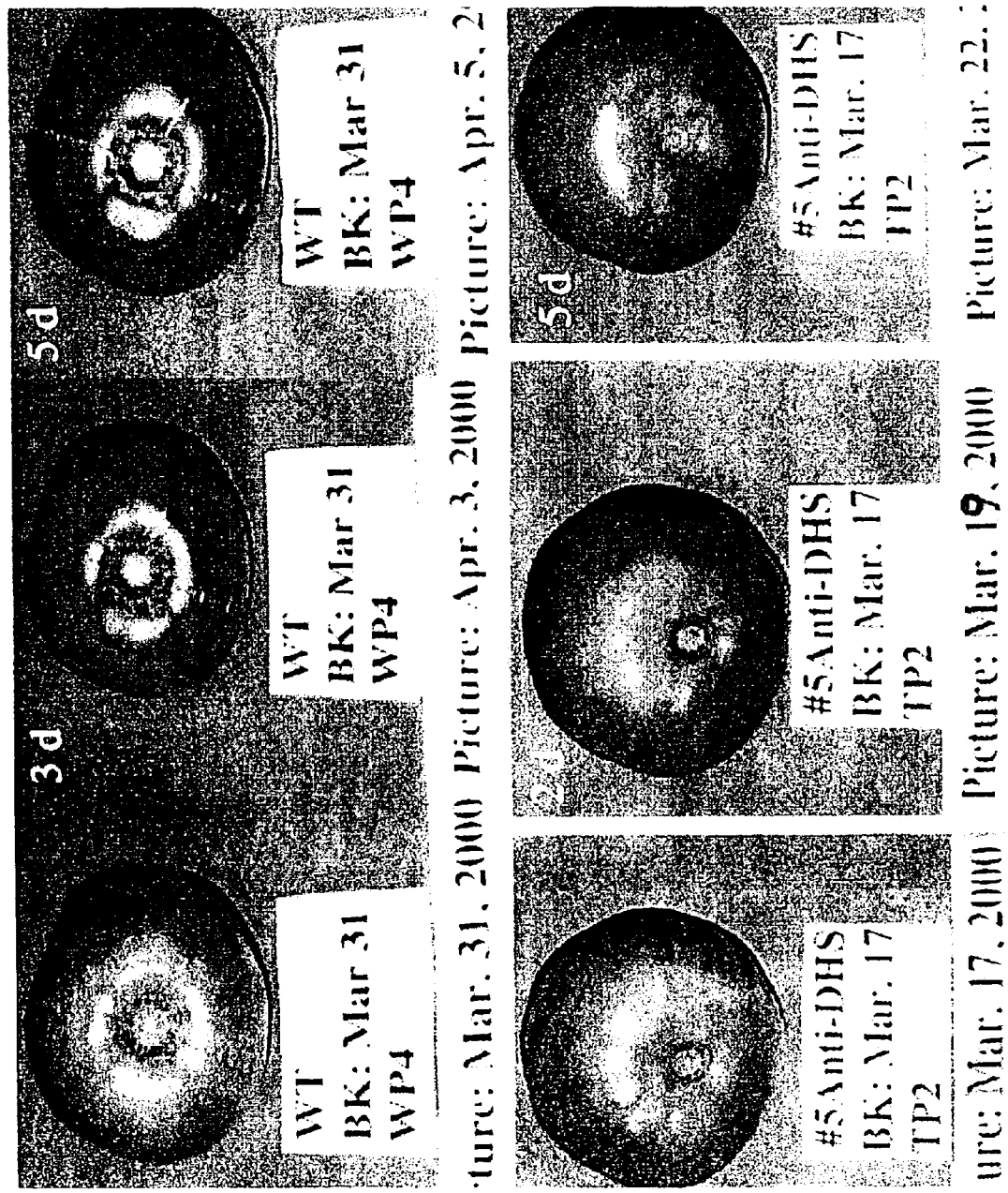
FIGS. 28 through 35 are photographs of tomato fruit from wild-type (top panels) and transgenic plants expressing the full-length senescence DHS gene in antisense orientation (bottom panels). Fruit were harvested at the breaker stage of development and ripened in a growth chamber. Days after harvest are indicated in the upper left corner of each panel.
Figure 29:
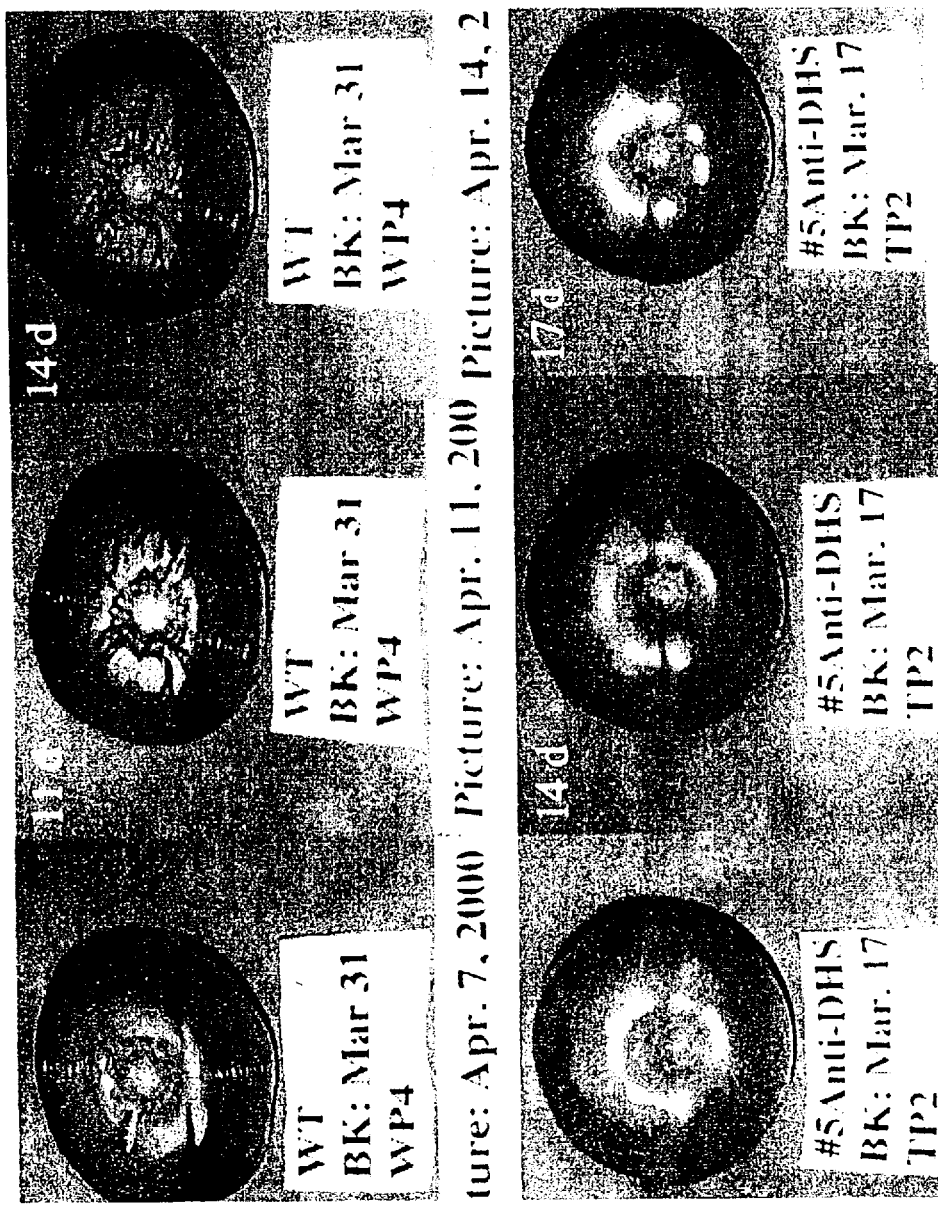
Figure 30:
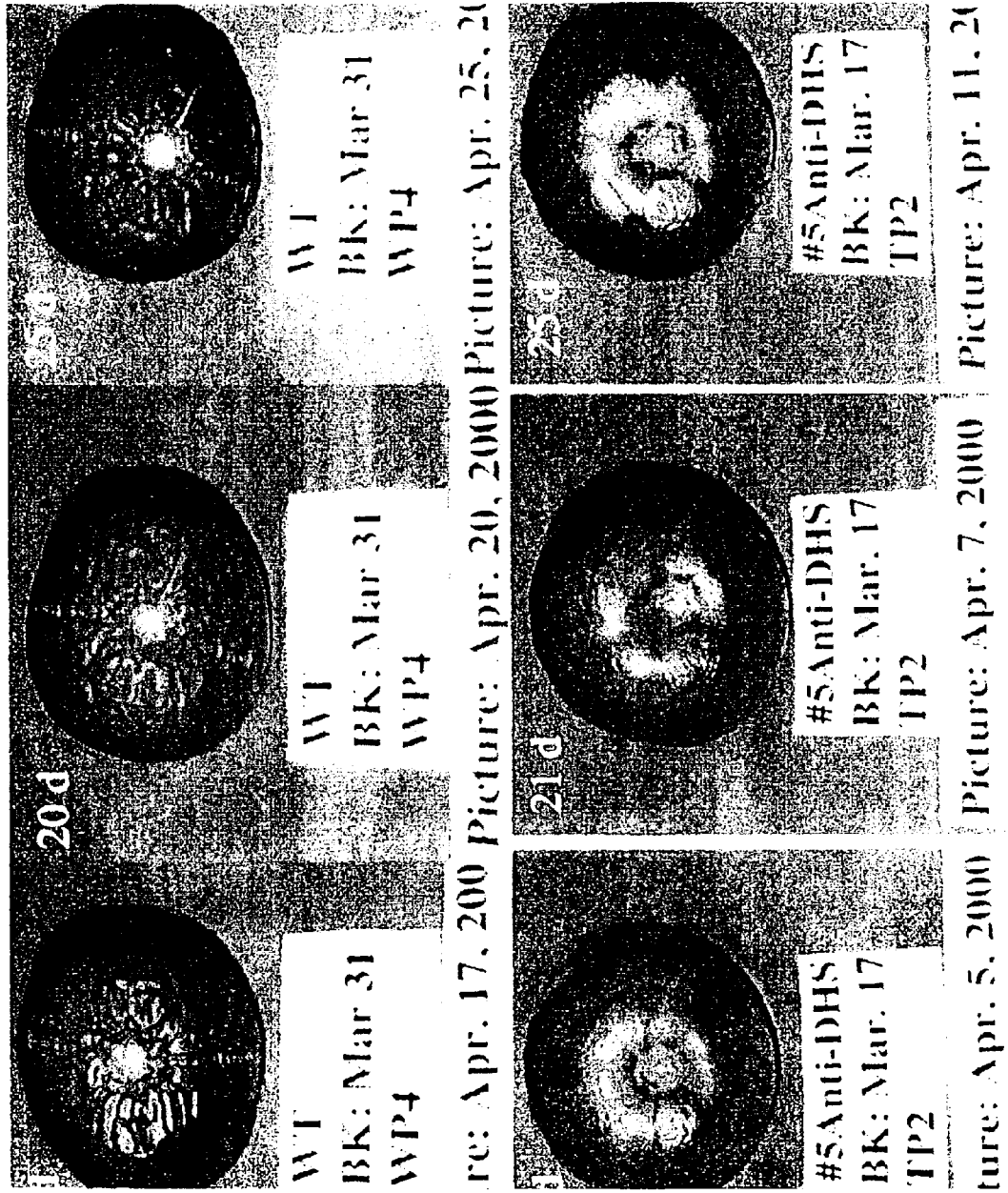
Figure 31:
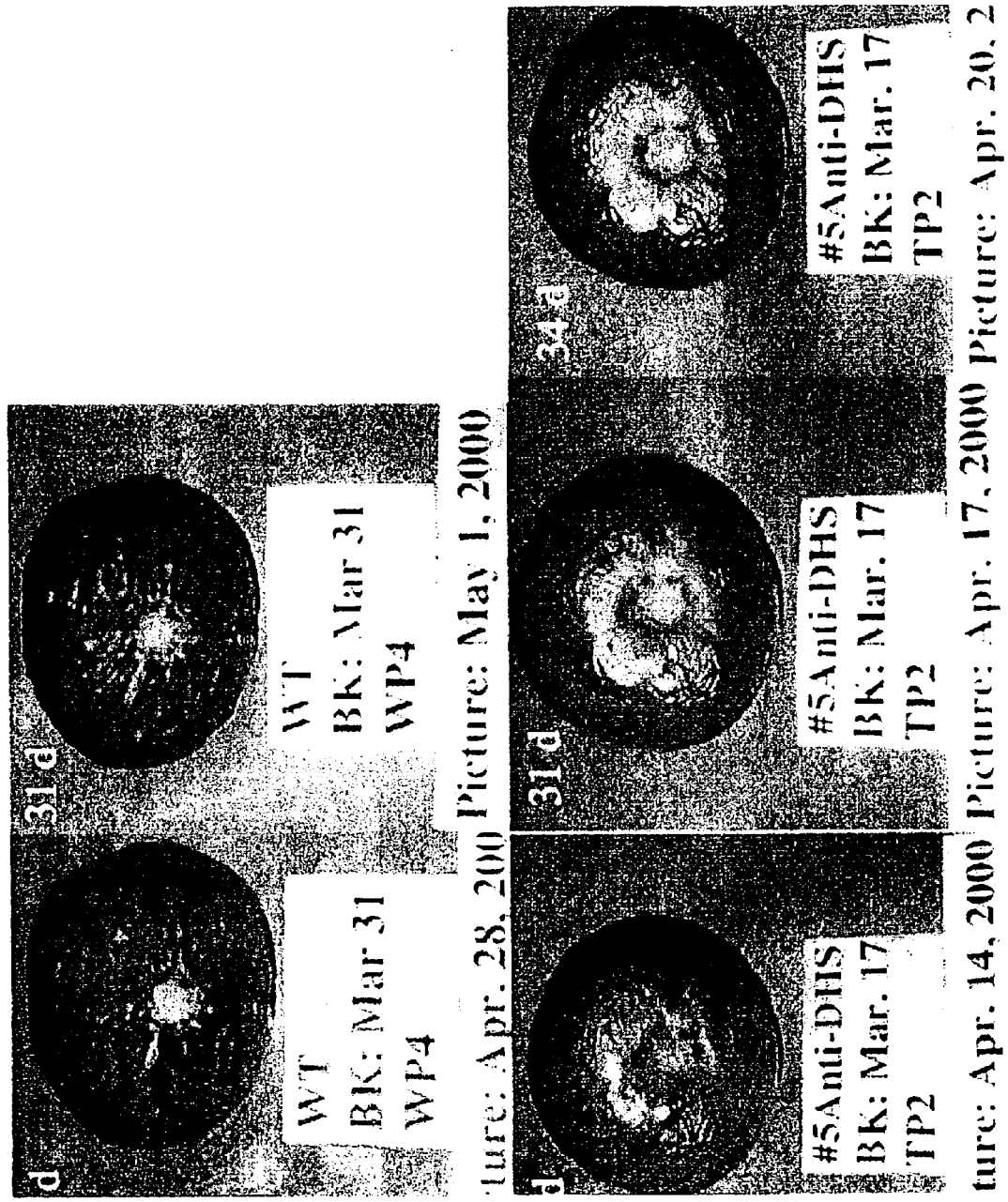
Figure 32:
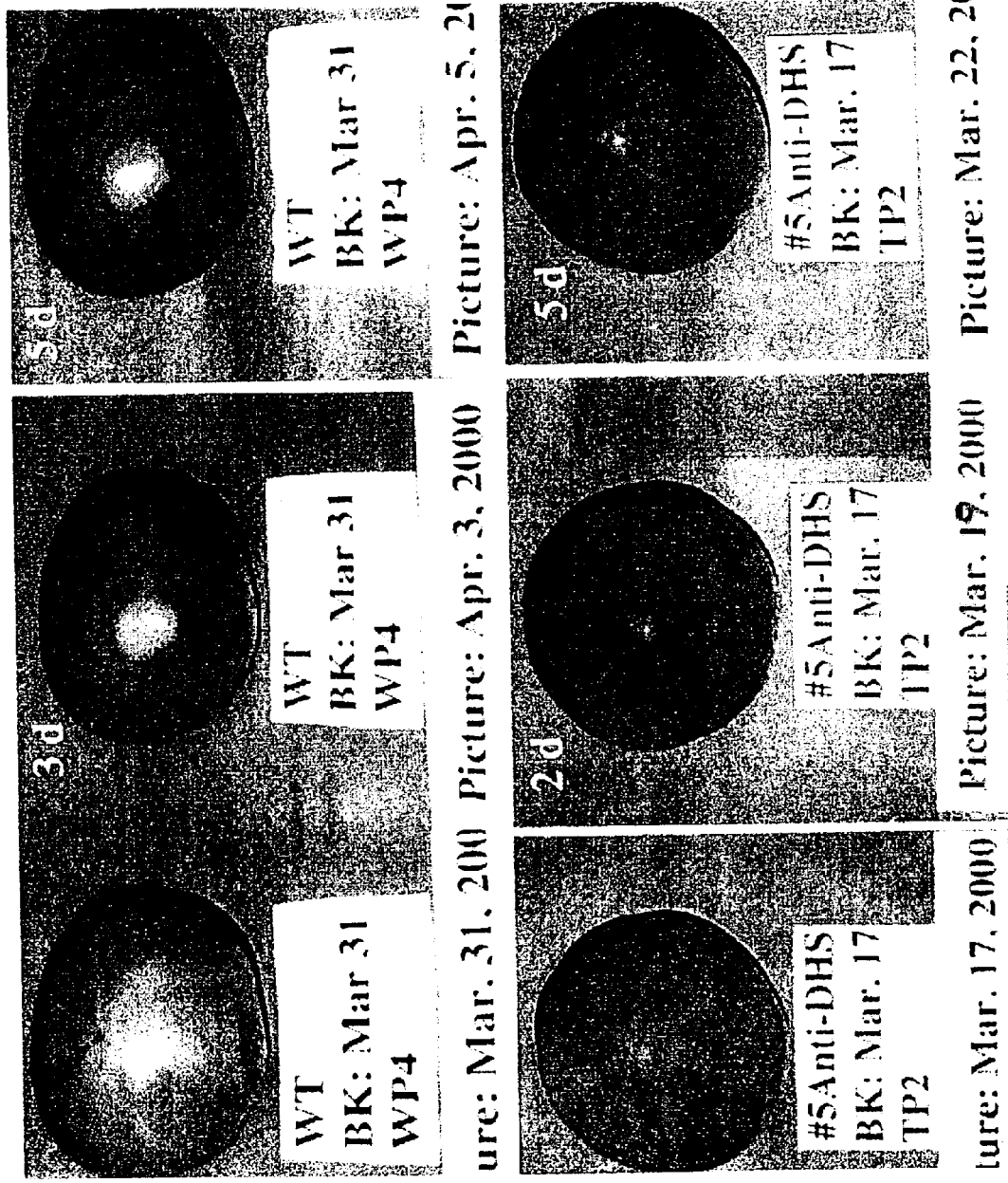
Figure 33:
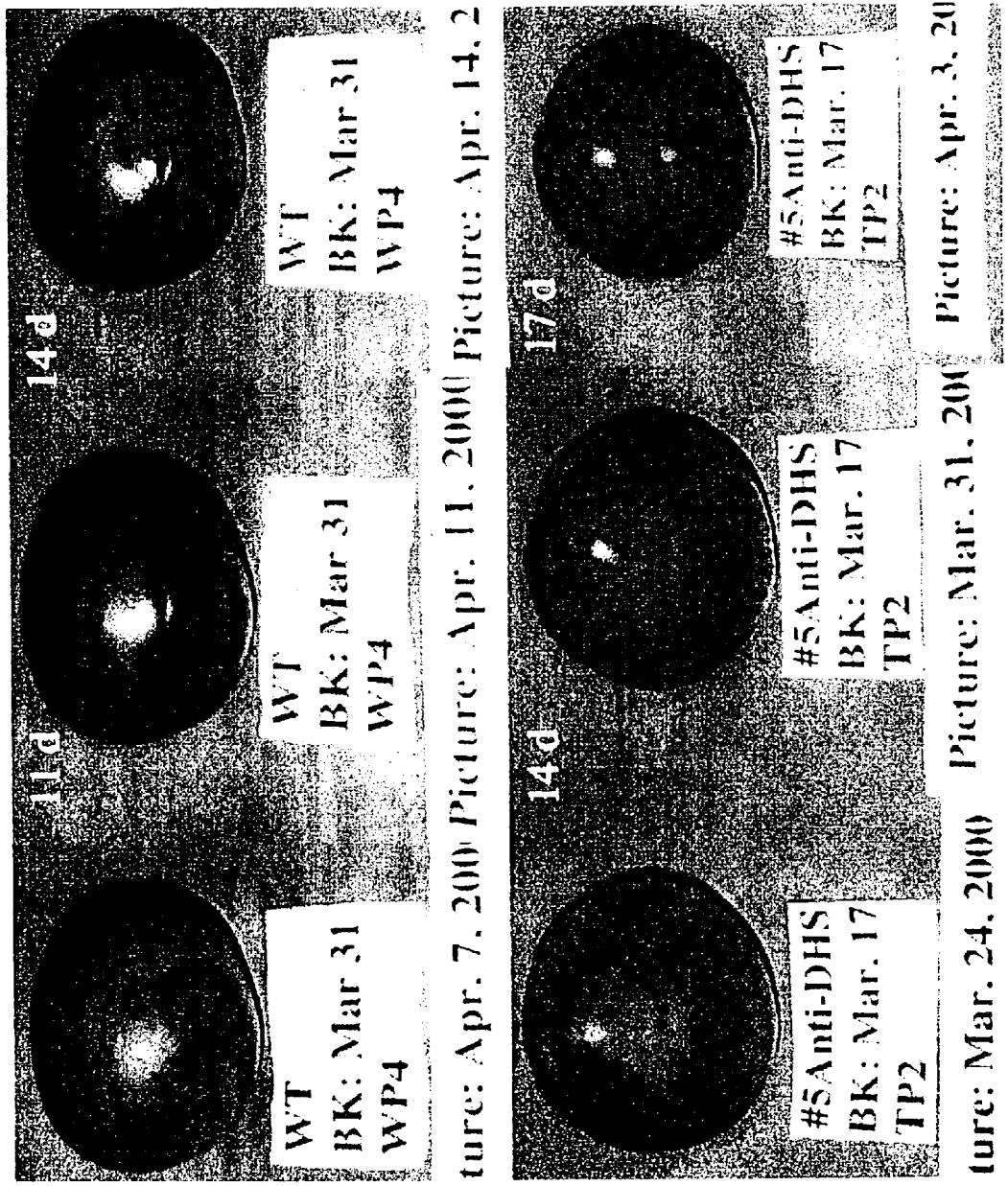
Figure 34:
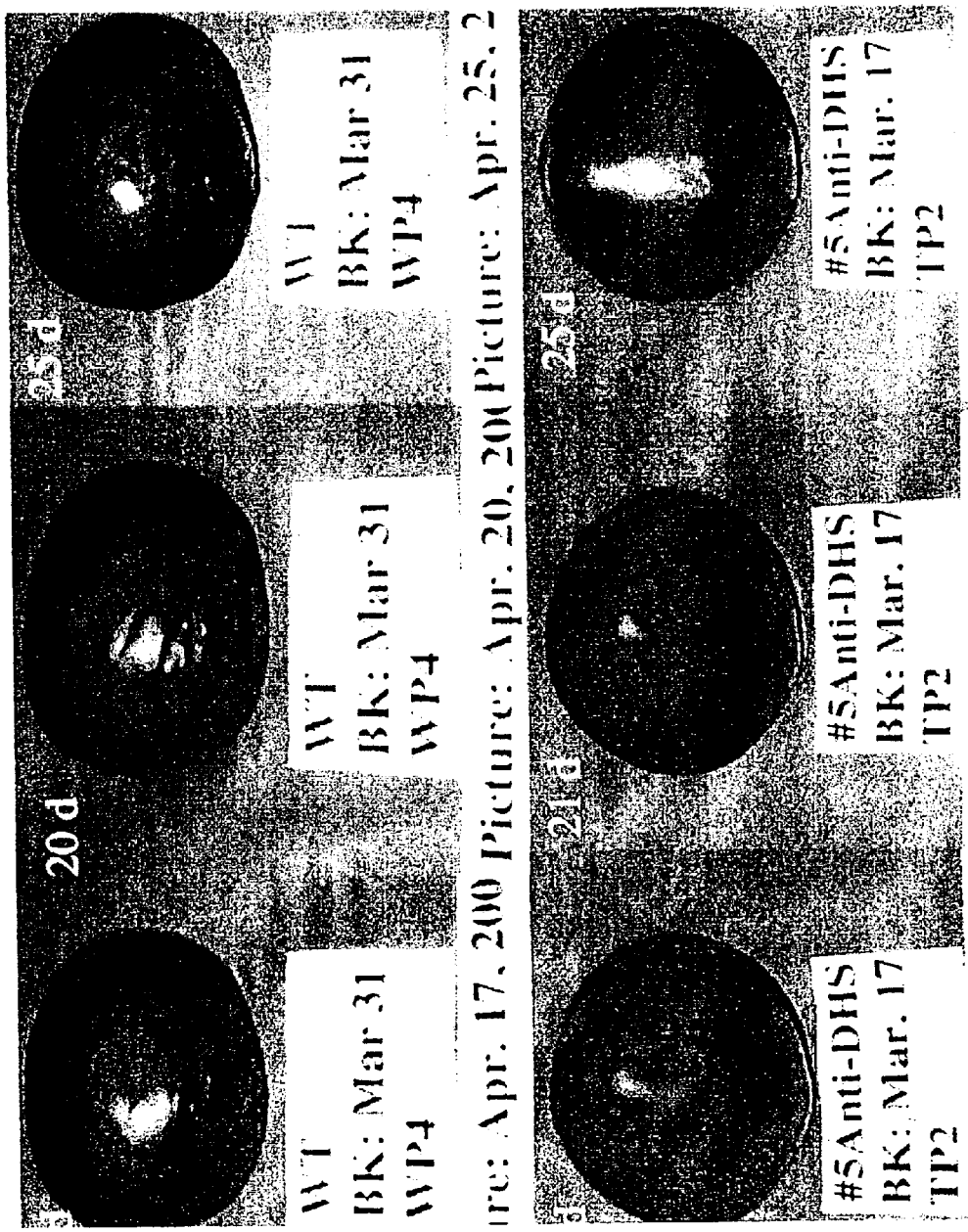
Figure 35:
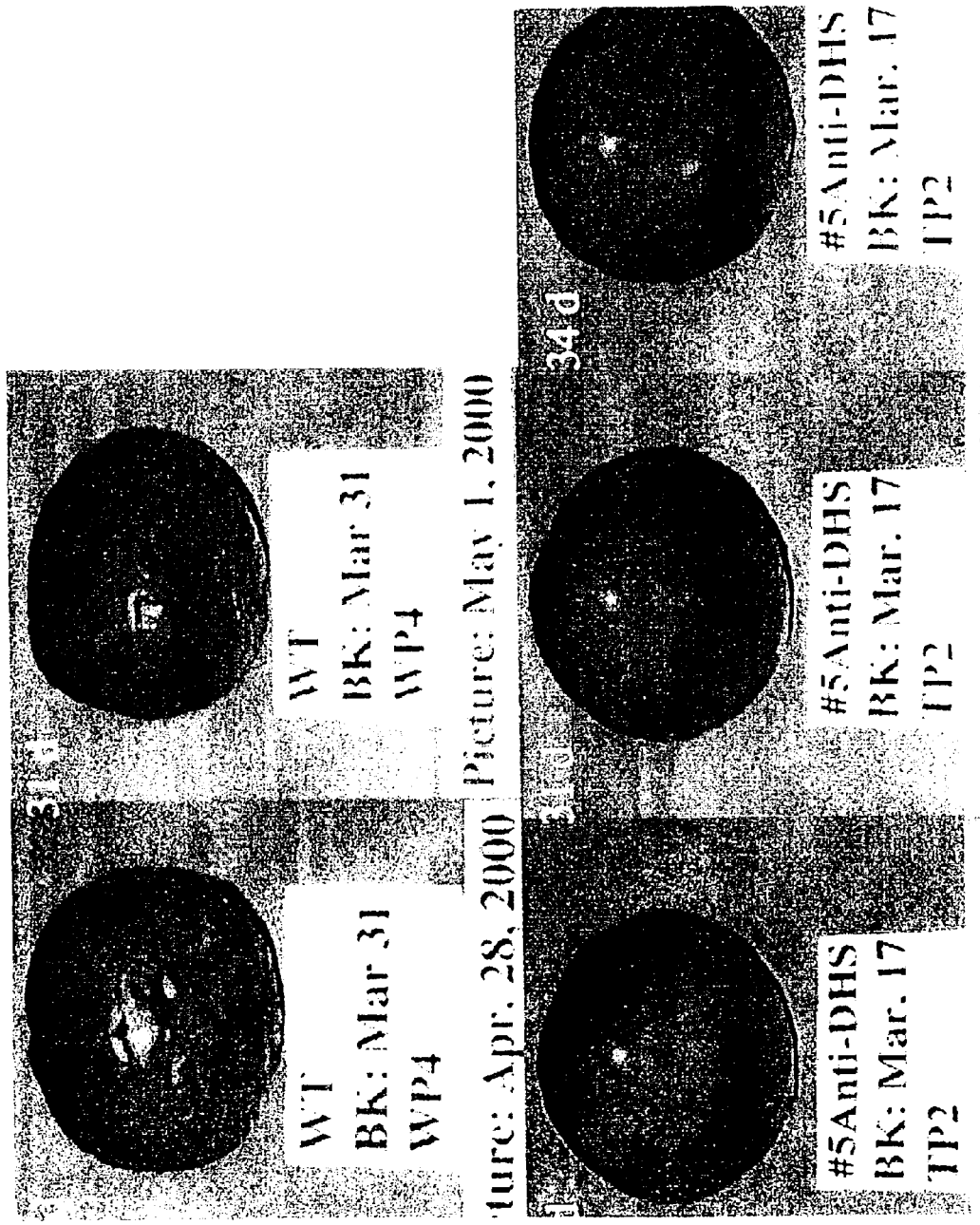

Similar results are obtained with tomato plants transformed with the 3' end of the tomato senescence-induced DHS gene (SEQ ID NO:27) in antisense orientation and under regulation of a double 35S promoter. Plants transformed with the 3' end of the gene in antisense orientation show increased leaf size and increased plant size in comparison to control (non-transformed) tomato plants. (FIGS. 26 and 27)

Tomato plants transformed with the full length tomato senescence-induced DHS in antisense orientation produce fruit that exhibits delayed softening and spoilage in comparison to wild type plants. (FIGS. 28 through 35). Thus, the methods and sequences of the present invention can be used to delay fruit softening and spoilage, as well as to increase plant biomass and seed yield and in general, delay senescence in plants.

The isolated nucleotide sequences of this invention can be used to isolate substantially complementary DHS and'or eIF-5A nucleotide sequence from other plants or organisms. These sequences can, in turn, be used to transform plants and thereby alter senescence of the transformed plants in the same manner as shown with the use of the isolated nucleotide sequences shown herein.

The genetic modifications obtained with transformation of plants with DHS, eIF-5A, fragments thereof or combinations thereof can effect a permanent change in levels of senescence-induced DHS, eIF-5A or both in the plant and be propagated in offspring plants by selfing or other reproductive schemes. The genetically altered plant is used to produce a new variety or line of plants wherein the alteration is stably transmitted from generation to generation. The present invention provides for the first time the appropriate DNA sequences which may be used to achieve a stable genetic modification of senescence in a wide range of different plants.

For the identification and isolation of the senescence-induced DHS gene and eIF-5A gene, in general, preparation of plasmid DNA, restriction enzyme digestion, agarose gel electrophoresis of DNA, polyacrylamide gel electrophoresis of protein, PCR, RT-PCR, Southern blots, Northern blots, DNA ligation and bacterial transformation were carried out using conventional methods well-known in the art. See, for example, Sambrook, J. et al., Molecular Cloning: A Laboratory Manual, 2nd ed., Cold Spring Harbor Press, Cold Spring Harbor, N.Y., 1989. Techniques of nucleic acid hybridization are disclosed by Sambrook (Supra).

As used herein, the term "plant" refers to either a whole plant, a plant part, a plant cell or a group of plant cells. The type of plant which can be used in the methods of the invention is not limited and includes, for example, ethylene-sensitive and ethylene-insensitive plants; fruit bearing plants such as apricots, apples, oranges, bananas, grapefruit, pears, tomatoes, strawberries, avocados, etc.; vegetables such as carrots, peas, lettuce, cabbage, turnips, potatoes, broccoli, asparagus, etc.; flowers such as carnations, roses, mums, etc.; agronomic crop plants and forest species such as corn, rice, soybean, alfalfa and the like; and in general, any plant that can take up and express the DNA molecules of the present invention. It may include plants of a variety of ploidy levels, including haploid, diploid, tetraploid and polyploid. The plant may be either a monocotyledon or dicotyledon.

A transgenic plant is defined herein as a plant which is genetically modified in some way, including but not limited to a plant which has incorporated heterologous or homologous senescence-induced DHS DNA or modified DNA or some portion of heterologous senescence-induced DHS DNA or homologous senescence-induced DHS DNA into its genome. Alternatively a transgenic plant of the invention may have incorporated heterologous or homologous senescence-induced eIF-5A DNA or modified DNA or some portion of heterologous senescence-induced eIF-5A DNA or homologous senescence-induced eIF-5A DNA into its genome. Transgenic plants of the invention may have incorporated heterologous or homologous senescence-induced DHS and eIF-5A DNA or modified DNA or some portion of heterologous senescence-induced DHS and eIF-5A DNA or homologous senescence-induced DHS DNA or a combination of heterologous and homologous DHS and eIF-5A sequences into its genome. The altered genetic material may encode a protein, comprise a regulatory or control sequence, or may be or include an antisense sequence or encode an antisense RNA which is antisense to the endogenous senescence-induced DHS or eIF-5A DNA or mRNA sequence or portion thereof of the plant. A "transgene" or "transgenic sequence" is defined as a foreign gene or partial sequence which has been incorporated into a transgenic plant.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6× S.S.C., 0.01 M EDTA, 1× Denhardt's solution and 0.5% SDS. Hybridization is carried out at about 68° C. for about 3 to 4 hours for fragments of cloned DNA and for about 12 to about 16 hours for total eukaryotic DNA. For lower stringencies the temperature of hybridization is reduced to about 42° C. below the melting temperature ($T_M$) of the duplex. The $T_M$ is known to be a function of the G-C content and duplex length as well as the ionic strength of the solution.

As used herein, the term "substantial sequence identity" or "substantial homology" is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include, for example, ability to hybridize under defined conditions, or in the case of proteins, immunological crossreactivity, similar enzymatic activity, etc. Each of these characteristics can readily be determined by the skilled practitioner by art known methods.

Additionally, two nucleotide sequences are "substantially complementary" if the sequences have at least about 70 percent, more preferably, 80 percent and most preferably about 90 percent sequence similarity between them. Two amino acid sequences are substantially homologous if they have at least 50%, preferably 70% similarity between the active portions of the polypeptides.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long antisense molecule from the 3' coding or non-coding region of tomato DHS will recognize and hybridize to an approximately 100 nucleotide portion of a nucleotide sequence within the 3' coding or non-coding region, respectively of carnation DHS gene or any other plant DHS gene so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20–30% larger or smaller, preferably no more than about 12–15% larger or smaller.

The term "functional derivative" of a nucleic acid (or poly- or oligonucleotide) is used herein to mean a fragment, variant, homolog, or analog of the gene or nucleotide sequence encoding senescence-induced DHS or senescence-induced eIF-5A. A functional derivative may retain at least a portion of the function of the senescence-induced DHS or eIF-5A encoding DNA which permits its utility in accordance with the invention. Such function may include the ability to hybridize under low stringency conditions with native tomato, Arabidopsis or carnation senescence-induced DHS or eIF-5A or substantially homologous DNA from another plant which encodes senescence-induced DHS or eIF-5A or with an mRNA transcript thereof, or, in antisense orientation, to inhibit the transcription and/or translation of plant senescence-induced DHS or eIF-5A mRNA, or the like.

A "fragment" of the gene or DNA sequence refers to any subset of the molecule, e.g., a shorter polynucleotide or oligonucleotide. A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different plant genus or species. An "analog" refers to a non-natural molecule substantially similar to or functioning in relation to either the entire molecule, a variant or a fragment thereof.

By "altered expression" or "modified expression" of a gene, e.g., the senescence-induced DHS gene or senescence-induced eIF-5A gene, is meant any process or result whereby the normal expression of the gene, for example, that expression occurring in an unmodified fruit bearing, flowering or other plant, is changed in some way. As intended herein, alteration in gene expression is complete or partial reduction in the expression of the senescence-induced DHS gene or senescence-induced eIF-5A gene or both, but may also include a change in the timing of expression, or another state wherein the expression of the senescence-induced DHS gene or senescence-induced eIF-5A gene or both differs from that which would be most likely to occur naturally in an unmodified plant or cultivar. A preferred alteration is one which results in reduction of senescence-induced DHS production, senescence-induced eIF-5A production or both by the plant compared to production in an unmodified plant.

In producing a genetically altered plant in accordance with this invention, it is preferred to select individual plantlets or plants by the desired trait, generally reduced senescence-induced DHS expression or production or reduced senescence-induced eIF-5A expression or both. Expression of senescence-induced DHS and senescence-induced eIF-5A can be determined, for example by observations of delayed or reduced senescence in transgenic plants. It is also possible to quantitate the activity of DHS and/or eIF-5A in transgenic plants in comparison to control (normal, non-transgenic) plants using known assays.

In order for a newly inserted gene or DNA sequence to be expressed, resulting in production of the protein which it encodes, or in the case of antisense DNA, to be transcribed, resulting in an antisense RNA molecule, the proper regulatory elements should be present in proper location and orientation with respect to the gene or DNA sequence. The regulatory regions may include a promoter, a 5'-non-translated leader sequence and a 3'-polyadenylation sequence as well as enhancers and other regulatory sequences.

Promoter regulatory elements that are useful in combination with the senescence-induced DHS gene to generate sense or antisense transcripts of the gene include any plant promoter in general, and more particularly, a constitutive promoter such as the fig wart mosaic virus 35S promoter, the cauliflower mosaic virus promoter, CaMV35S promoter, or the MAS promoter, or a tissue-specific or senescence-induced promoter, such as the carnation petal GST1 promoter or the Arabidopsis SAG12 promoter (See, for example, J. C. Palaqui et al., Plant Physiol., 112:1447–1456 (1996); Morton et al., Molecular Breeding, 1:123–132 (1995); Fobert et al., Plant Journal, 6:567–577 (1994); and Gan et al., Plant Physiol., 113:313 (1997), incorporated herein by reference). Preferably, the promoter used in the present invention is a constitutive promoter, most preferably a double 35S promoter is used.

Expression levels from a promoter which is useful for the present invention can be tested using conventional expression systems, for example by measuring levels of a reporter gene product, e.g., protein or mRNA in extracts of the leaves, flowers, fruit or other tissues of a transgenic plant into which the promoter/reporter gene have been introduced.

The present invention provides antisense oligonucleotides and polynucleotides complementary to the gene encoding tomato senescence-induced DHS, carnation senescence-induced DHS, Arabidopsis senescence-induced DHS or complementary to a gene or gene fragment from another plant, which hybridizes with the tomato, carnation or Arabidopsis senescence-induced DHS gene under low to high stringency conditions. The present invention also provides antisense oligonucleotides and polynucleotides complementary to the gene encoding tomato senescence-induced eIF-5A, carnation senescence-induced eIF-5A, Arabidopsis senescence-induced eIF-5A or complementary to a gene or gene fragment from another plant, which hybridizes with the tomato, carnation or Arabidopsis senescence-induced eIF-5A gene under low to high stringency conditions. Such antisense oligonucleotides should be at least about six nucleotides in length to provide minimal specificity of hybridization and may be complementary to one strand of DNA or mRNA encoding the senescence-induced gene or a portion thereof, or to flanking sequences in genomic DNA which are involved in regulating senescence-induced DHS or eIF-5A gene expression. The antisense oligonucleotide may be as large as 100 nucleotides or more and may extend in length up to and beyond the full coding sequence for which it is antisense. The antisense oligonucleotides can be DNA or RNA or chimeric mixtures or derivatives or modified versions thereof, single stranded or double stranded.

The action of the antisense oligonucleotide may result in alteration, primarily inhibition, of senescence-induced DHS expression, senescence-induced eIF-5A expression or both in cells. For a general discussion of antisense see: Alberts, et al., Molecular Biology of the Cell, 2nd ed., Garland Publishing, Inc. New York, N.Y., 1989 (in particular pages 195–196, incorporated herein by reference).

The antisense oligonucleotide may be complementary to any corresponding portion of the senescence-induced DHS or eIF-5A gene. In one embodiment, the antisense oligonucleotide may be between 6 and 100 nucleotides in length, and may be complementary to the 5'-non-coding or sequences within the 3'-end of the senescence-induced DHS or eIF-5A sequence, for example. Antisense oligonucleotides primarily complementary to 5'-non-coding sequences are known to be effective inhibitors of expression of genes encoding transcription factors. Branch, M. A., Molec. Cell Biol., 13:4284–4290 (1993).

Preferred antisense oligonucleotides are substantially complementary to a portion of the mRNA encoding senescence-induced DHS or senescence-induced eIF-5A, the portion of the mRNA being approximately the same size as the antisense oligonuleotide. For example, introduction of the full length cDNA clone encoding senescence-induced DHS or eIF-5A in an antisense orientation into a plant is expected to result in successfully altered senescence-induced DHS and/or eIF-5A gene expression. Moreover, as demonstrated in FIGS. 21-35 introduction of partial sequences, targeted to specific portions of the senescence-induced DHS gene or senescence-induced eIF-5A gene or both, can be equally effective.

The minimal amount of homology required by the present invention is that sufficient to result in sufficient complementarity to provide recognition of the specific target RNA or DNA and inhibition or reduction of its translation or function while not affecting function of other RNA or DNA molecules and the expression of other genes. While the antisense oligonucleotides of the invention comprise sequences complementary to a corresponding portion of an RNA transcript of the senescence-induced DHS gene or senescence-induced eIF-5A gene, absolute complementarity, although preferred is not required. The ability to hybridize may depend on the length of the antisense oligonucleotide and the degree of complementarity. Generally, the longer the hybridizing nucleic acid, the more base mismatches with the senescence-induced DHS target sequence it may contain and still form a stable duplex. One skilled in the art can ascertain a tolerable degree of mismatch by use of standard procedures to determine the melting temperature of the hybridized complex, for example.

The antisense RNA oligonucleotides may be generated intracellularly by transcription from exogenously introduced nucleic acid sequences. The antisense molecule may be delivered to a cell by transformation or transfection or infection with a vector, such as a plasmid or virus into which is incorporated DNA encoding the antisense senescence-induced DHS sequence operably linked to appropriate regulatory elements, including a promoter. Within the cell the exogenous DNA sequence is expressed, producing an antisense RNA of the senescence-induced DHS gene.

Vectors can be plasmids, preferably, or may be viral or other vectors known in the art to replicate and express genes encoded thereon in plant cells or bacterial cells. The vector becomes chromosomally integrated such that it can be transcribed to produce the desired antisense senescence-induced DHS RNA. Such plasmid or viral vectors can be constructed by recombinant DNA technology methods that are standard in the art. For example, the vector may be a plasmid vector containing a replication system functional in a prokaryotic host and an antisense oligonucleotide or polynucleotide according to the invention. Alternatively, the vector may be a plasmid containing a replication system functional in *Agrobacterium* and an antisense oligonucleotide or polynucleotide according to the invention. Plasmids that are capable of replicating in *Agrobacterium* are well known in the art. See, Miki, et al., Procedures for Introducing Foreign DNA Into Plants, Methods in Plant Molecular Biology and Biotechnology, Eds. B. R. Glick and J. E. Thompson. CRC Press (1993), PP. 67–83.

The tomato DHS gene was cloned in antisense orientation into a plasmid vector in the following manner. The pCD plasmid, which is constructed from a pUC18 backbone and contains the 35S promoter from cauliflower mosaic virus (CaMV) followed by a multiple cloning site and an octapine synthase termination sequence was used for cloning the tomato DHS gene. The pCd-DHS (antisense) plasmid was constructed by subcloning the full length tomato DHS gene in the antisense orientation into the pCD plasmid using XhoI and SacI restriction sites.

An oligonucleotide, preferably between about 6 and about 100 nucleotides in length and complementary to the target sequence of senescence-induced DHS or senescence-induced eIF-5A gene, may be prepared by recombinant nucleotide technologies or may be synthesized from mononucleotides or shorter oligonucleotides, for example. Automated synthesizers are applicable to chemical synthesis of the oligo- and polynucleotides of the invention. Procedures for constructing recombinant nucleotide molecules in accordance with the present invention are disclosed in Sambrook, et al., In: Molecular Cloning: A Laboratory Manual, 2nd ed., Cold Spring Harbor Press, Cold Spring Harbor, N.Y. (1989), which is incorporated herein in its entirety. Oligonucleotides which encode antisense RNA complementary to senescence-induced deoxyhypusine synthase sequence can be prepared using procedures well known to those in the art. Details concerning such procedures are provided in Maniatis, T. et al., Molecular mechanisms in the Control of Gene expression, eds., Nierlich, et al., eds., Acad. Press, N.Y. (1976).

In an alternative embodiment of the invention, inhibition of expression of endogenous plant senescence-induced DHS, senescence-induced eIF-5A or both is the result of co-suppression through over-expression of an exogenous senescence-induced DHS or eIF-5A gene or gene fragment or both introduced into the plant cell. In this embodiment of the invention, a vector encoding senescence-induced DHS, senescence-induced eIF-5A or both in the sense orientation is introduced into the cells in the same manner as described herein for antisense molecules. Preferably, the senescence-induced DHS or senescence-induced eIF-5A is operatively linked to a strong constitutive promoter, such as for example the fig wart mosaic virus promoter or CaMV35S or a double 35 S promoter.

In another embodiment of the invention, inhibition of expression of endogenous plant senescence-induced DHS, senescence-induced eIF-5A or both is effected through the use of ribozymes. Ribozymes are RNA molecules exhibiting sequence-specific endoribonuclease activity. An example is the hammerhead ribozyme which cleaves at a UH (where H is an A, C or U residue) recognition site in the target RNA and contains base-pairing regions that direct the catalytic domain of the ribozyme to the target site of the substrate RNA. Ribozymes are highly target-specific and can be designed to inactivate one member of a multigene family or targeted to conserved regions of related mRNAs. (See Merlo et al., The Plant Cell, 10:1603–1621, 1998). The ribozyme molecule may be delivered to a cell by transformation, transfection or infection with a vector, such as a plasmid or virus, into which is incorporated the ribozyme operatively linked to appropriate regulatory elements, including a promoter. Such a ribozyme construct contains base-pairing arms that direct it to a cleavage site within the senescence-induced DHS mRNA, or senescence-induced eIF-5A mRNA resulting in cleavage of DHS or eIF-5A mRNA and inhibition of senescence -induced DHS and/or eIF-5A expression.

Transgenic plants made in accordance with the present invention may be prepared by DNA transformation using any method of plant transformation known in the art. Plant transformation methods include direct co-cultivation of plants, tissues or cells with *Agrobacterium* tumefaciens or direct infection (Miki, et al., Meth. in Plant Mol. Biol. and Biotechnology, (1993), p. 67–88); direct gene transfer into protoplasts or protoplast uptake (Paszkowski, et al., EMBO J., 12:2717 (1984); electroporation (Fromm, et al., Nature, 319:719 (1986); particle bombardment (Klein et al., BioTechnology, 6:559–563 (1988); injection into meristematic tissues of seedlings and plants (De LaPena, et al., Nature, 325:274–276 (1987); injection into protoplasts of cultured cells and tissues (Reich, et al., BioTechnology, 4:1001–1004 (1986)).

Generally a complete plant is obtained from the transformation process. Plants are regenerated from protoplasts, callus, tissue parts or explants, etc. Plant parts obtained from the regenerated plants in which the expression of senescence-induced DHS, senescence-induced eIF-5A or both is altered, such as leaves, flowers, fruit, seeds and the like are included in the definition of "plant" as used herein. Progeny, variants and mutants of the regenerated plants are also included in the definition of "plant."

The tomato, carnation or *Arabidopsis* senescence-induced DHS protein or functional derivatives thereof, and tomato, carnation or *Arabidopsis* senescence-induced eIF-5A protein or functional derivatives thereof are preferably produced by recombinant technologies, optionally in combination with chemical synthesis methods. In one embodiment of the invention the senescence-induced DHS is expressed as a fusion protein, preferably consisting of the senescence-induced DHS fused with maltose binding protein.

"Functional derivatives" of the senescence-induced DHS or senescence-induced eIF-5A protein as described herein are fragments, variants, analogs, or chemical derivatives of senescence-induced DHS or senescence-induced eIF-5A, respectively, which retain at least a portion of the senescence-induced DHS or eIF-5A activity or immunological cross reactivity with an antibody specific for senescence-induced DHS or senescence-induced eIF-5A, respectively. A fragment of the senescence-induced DHS or senescence-induced eIF-5A protein refers to any subset of the molecule. Variant peptides may be made by direct chemical synthesis, for example, using methods well known in the art. An analog of senescence-induced DHS or senescence-induced eIF-5A refers to a non-natural protein substantially similar to either the entire protein or a fragment thereof. Chemical derivatives of senescence-induced DHS or senescence-induced-eIF-5A contain additional chemical moieties not normally a part of the peptide or peptide fragment. Modifications may be introduced into peptides or fragments thereof by reacting targeted amino acid residues of the peptide with an organic derivatizing agent that is capable of reacting with selected side chains or terminal residues.

A senescence-induced DHS or senescence-induced eIF-5A protein or peptide according to the invention may be produced by culturing a cell transformed with a nucleotide sequence of this invention (in the sense orientation), allowing the cell to synthesize the protein and then isolating the protein, either as a free protein or as a fusion protein, depending on the cloning protocol used, from either the culture medium or from cell extracts. Alternatively, the protein can be produced in a cell-free system. Ranu, et al., Meth. Enzymol., 60:459–484, (1979).

Having now generally described the invention, the same will be more readily understood through reference to the following examples which are provided by way of illustration, and are not intended to be limiting to the present invention.

EXAMPLE 1

Messenger RNA (mRNA) Isolation

Total RNA was isolated from tomato flowers and tomato fruit at various developmental stages and from leaves (untreated or after chilling or sorbitol treatment). Briefly, the tissue (5 g) was ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of cheesecloth and centrifuged at 10,000×g at 4° C. for 30 minutes. The supernatant was then subjected to cesium chloride density gradient centrifugation at 26,000×g for 20 hours. The pelleted RNA was rinsed with 75% ethanol, resuspended in 600 $\mu$l DEPC-treated water and the RNA precipitated at –70° C. with 0.75 ml 95% ethanol and 30 $\mu$l of 3M NaOAc. Ten $\mu$g of RNA were fractionated on a 1.2% denaturing formaldehyde agarose gel and transferred to a nylon membrane. Randomly primed $^{32}$P-dCTP-labelled full length DHS cDNA (SEQ ID NO:1) was used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to x-ray film overnight at –70° C.

PolyA$^+$ mRNA was isolated from total RNA using the PolyA$^+$ tract mRNA Isolation System available from Promega. PolyA$^+$ mRNA was used as a template for cDNA synthesis using the ZAP Express® cDNA synthesis system available from Stratagene (La Jolla, Calif.)

Tomato Leaf cDNA Library Screening

A cDNA library made using mRNA isolated from Match F1 hybrid tomato leaves that had been exposed to 2 M sorbitol for six hours was diluted to approximately 5×10$^6$ PFU/ml. The cDNA library was screened using a $^{32}$P-labelled 600 bp RT-PCR fragment. Three positive cDNA clones were excised and recircularized into a pBK-CMV® (Stratagene) phagemid using the method in the manufacturer's instructions. The full length cDNA was inserted into the pBK-CMV vector.

Plasmid DNA Isolation, DNA Sequencing

The alkaline lysis method described by Sambrook et al., (Supra) was used to isolate plasmid DNA. The full length positive cDNA clone was sequenced using the dideoxy sequencing method. Sanger, et al., Proc. Natl. Acad. Sci. USA, 74:5463–5467. The open reading frame was compiled and analyzed using BLAST search (GenBank, Bethesda, Md.) and alignment of the five most homologous proteins with the derived amino acid sequence of the encoded gene was achieved using a BCM Search Launcher: Multiple Sequence Alignments Pattern-Induced Multiple Alignment Method (See F. Corpet, Nuc. Acids Res., 16:10881–10890, (1987)). Functional motifs present in the derived amino acid sequence were identified by MultiFinder.

Northern Blot Hybridizations of Tomato RNA

Ten $\mu$g of total RNA isolated from tomato flowers at various stages (bud and blossom and senescing petals that are open widely or drying), tomato leaves, and tomato fruit at various stages of ripening (breaker, i.e., green fruit with less than 10% red color, pink, i.e., the entire fruit is orange or pink, and red, either soft or firm) were separated on 1% denatured formaldehyde agarose gels and immobilized on nylon membranes. The full length tomato cDNA labelled with $^{32}$P-dCTP using a random primer kit (Boehringer Mannheim) was used to probe the filters (7×10$^7$ cpm). The filters were washed once with 1×SSC, 0.1% SDS at room temperature and three times with 0.2×SSC, 0.1% SDS at 65° C. The filters were dried and exposed to X-ray film overnight at –70° C. The results are shown in FIGS. 6, 7, 8 and 9.

Northern Blot Hybridization of *Arabidopsis* RNA

Total RNA from leaves of *Arabidopsis* plants at five weeks of age (lane 1), six weeks (lane 2) and seven weeks (lane 3) was isolated as above, separated on 1% denatured formaldehyde agarose gels and immobilized on nylon membranes. The full-length *Arabidopsis* senescence-induced DHS cDNA labelled with $^{32}$P-dCTP using a random primer kit (Boehringer Mannheim) was used to probe the filters (7×10$^7$ cpm). The filters were washed once with 1×SSC, 0.1% SDS at room temperature and three times with 0.2× SSC, 0.1% SDS at 65° C. The filters were dried and exposed to X-ray film overnight at −70° C. The results are shown in FIG. 11.

Northern Blot Hybridization of Carnation RNA

Figure 12:
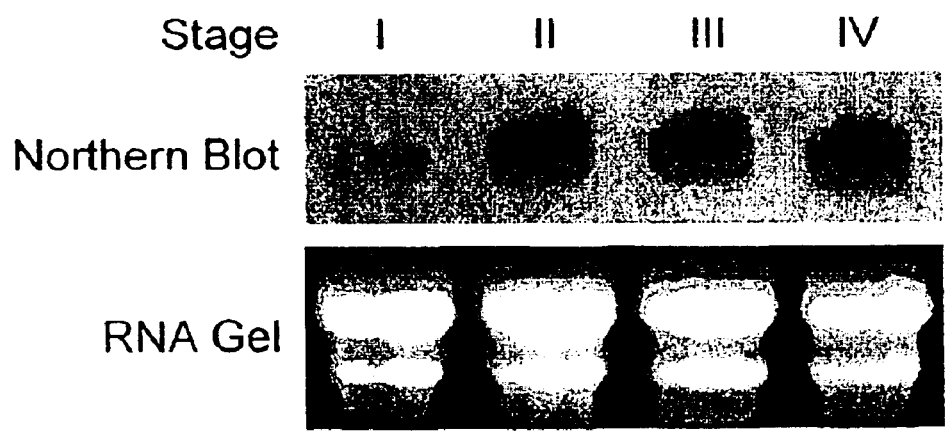
FIG. 12 is a Northern blot of total RNA isolated from petals of carnation flowers at various stages. The blot was probed with $^{32}$P-dCTP-labelled full-length carnation senescence-induced DHS cDNA. The autoradiograph is at the top, the ethidium stained gel below.
Figure 16:
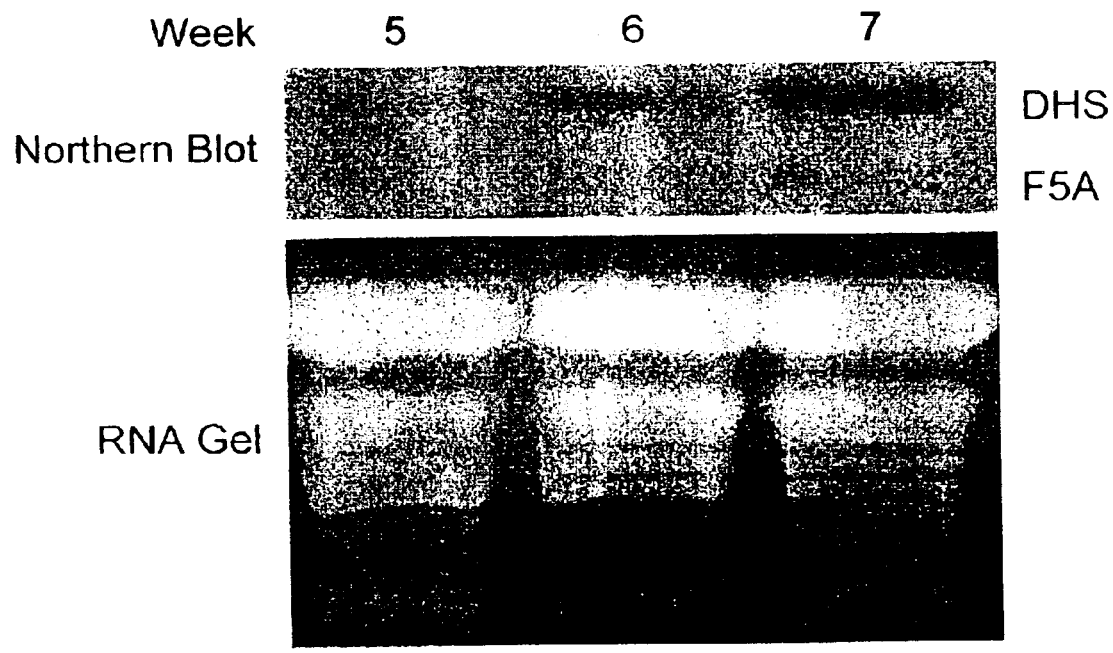
FIG. 16 is a Northern blot of total RNA isolated from leaves of *Arabidopsis* plants at various developmental stages. The blot was probed with $^{32}$P-dCTP-labelled full-length *Arabidopsis* senescence-induced DHS cDNA and full-length senescence-induced eIF-5A. The autoradiograph is at the top, the ethidium stained gel below.

Total RNA from petals of carnation plants at various stages of flower development, i.e., tight-bud flowers (lane 1), beginning to open (lane 2), fully open flowers (lane 3), flowers with inrolling petals (lane 4), was isolated as above, separated on 1% denatured formaldehyde agarose gels and immobilized on nylon membranes. The full-length carnation senescence-induced DHS cDNA labelled with $^{32}$P-dCTP using a random primer kit (Boehringer Mannheim) was used to probe the filters (7×10$^7$ cpm). The filters were washed once with 1×SSC, 0.1% SDS at room temperature and three times with 0.2×SSC, 0.1% SDS at 65° C. The filters were dried and exposed to X-ray film overnight at −70° C. The results are shown in FIG. 12.

EXAMPLE 2

Sorbitol Induction of Tomato Senescence-Induced DHS Gene

Tomato leaves were treated with 2 M sorbitol in a sealed chamber for six hours. RNA was extracted from the sorbitol treated leaves as follows.

Leaves (5 g) were ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of cheesecloth and centrifuged at 10,000×g at 4° C. for 30 minutes. The supernatant was then subjected to cesium chloride density gradient centrifugation at 26,000×g for 20 hours. The pelleted RNA was rinsed with 75% ethanol, resuspended in 600 μl DEPC-treated water and the RNA precipitated at −70° C. with 0.75 ml 95% ethanol and 30 μl of 3M NaOAc. Ten μg of RNA were fractionated on a 1.2% denaturing formaldehyde agarose gel and transferred to a nylon membrane. Randomly primed $^{32}$P-dCTP-labelled full length DHS cDNA (SEQ ID NO:1) was used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to x-ray film overnight at −70° C.

The results are shown in FIG. 8. As can be seen, transcription of DHS is induced in leaves by sorbitol.

EXAMPLE 3

Induction of the Tomato DHS Gene in Senescing Flowers

Tight flower buds and open, senescing flowers of tomato plants were harvested, and RNA was isolated as in Example 2. Ten μg RNA were fractionated on a 1.2% denaturing formaldehyde agarose gel and transferred to a nylon membrane. Randomly primed $^{32}$P-dCTP-labelled full length DHS cDNA (SEQ ID NO.1) was used to probe the membrane at 42° C. overnight. The membrane then was washed once in 1×SSC containing 0.1% SDS at room temperature for 15 minutes and then washed three times in 0.2×SSC containing 0.1% SDS at 65° C. for fifteen minutes each. The membrane was exposed to x-ray film overnight at −70° C.

The results are shown in FIG. 6. As can be seen, transcription of DHS is induced in senescing flowers.

EXAMPLE 4

Induction of the Tomato DHS Gene in Ripening Fruit

RNA was isolated from breaker, pink and ripe fruit as in Example 2. Ten μg RNA were fractionated on a 1.2% denaturing formaldehyde agarose gel and transferred to a nylon membrane. Randomly primed $^{32}$P-dCTP-labelled full length DHS cDNA (SEQ ID NO.1) (FIG. 1) was used to probe the membrane at 42° C. overnight. The membrane then was washed once in 1×SSC containing 0.1% SDS at room temperature for 15 minutes and then washed three times in 0.2×SSC containing 0.1% SDS at 65° C. for fifteen minutes each. The membrane was exposed to x-ray film overnight at −70° C.

The results are shown in FIG. 7. As can be seen, transcription of DHS is strongest in ripe, red fruit just prior to the onset of senescence leading to spoilage.

EXAMPLE 5

Induction of Tomato Senescence-Induced DHS Gene by Chilling

Tomato plants in pots (7–8 weeks old) were exposed to 6° C. for two days, three days or six days in a growth chamber. The light cycle was set for eight hours of dark and sixteen hours of light. Plants were rewarmed by moving them back into a greenhouse. Plants that were not rewarmed were harvested immediately after removal from the growth chamber. RNA was extracted from the leaves as follows.

Leaves (5 g) were ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of cheesecloth and centrifuged at 10,000 g at 4° C. for 30 minutes. The supernatant was then subjected to cesium chloride density gradient centrifugation at 26,000 g for 20 hours. The pelleted RNA was rinsed with 75% ethanol, resuspended in 600 μl DEPC-treated water and the RNA precipitated at −70° C. with 0.75 ml 95% ethanol and 30 μl of 3M NaOAc. Ten μg of RNA were fractionated on a 1.2% denaturing formaldehyde agarose gel and transferred to a nylon membrane. Randomly primed $^{32}$P-dCTP-labelled full length DHS cDNA (SEQ ID NO:1) was used to probe the membrane at 42° C. overnight. The membrane was then washed once in 1×SSC containing 0.1% SDS at room temperature for 15 minutes and three times in 0.2×SSC containing 0.1% SDS at 65° C. for 15 minutes each. The membrane was exposed to x-ray film overnight at −70° C.

The results are shown in FIG. 9. As can be seen, transcription of DHS is induced in leaves by exposure to chilling temperature and subsequent rewarming, and the enhanced transcription correlates with chilling damage measured as membrane leakiness.

EXAMPLE 6

Generation of an *Arabidopsis* PCR Product Using Primers Based on Unidentified

*Arabidopsis* Genomic Sequence

A partial length senescence-induced DHS sequence from an *Arabidopsis* cDNA template was generated by PCR using a pair of oligonucleotide primers designed from *Arabidopsis* genomic sequence. The 5′ primer is a 19-mer having the sequence, 5′-GGTGGTGTTGAGGAAGATC (SEQ ID NO:7); the 3′ primer is a 20 mer having the sequence, GGTGCACGCCCTGATGAAGC-3′ (SEQ ID NO:8). A polymerase chain reaction using the Expand High Fidelity PCR System (Boehringer Mannheim) and an *Arabidopsis* senescing leaf cDNA library as template was carried out as follows.

| Reaction components: | |
|---|---|
| cDNA | 1 μl (5 × 10⁷ pfu) |
| dNTP (10 mM each) | 1 μl |
| MgCl₂ (5 mM) + 10x buffer | 5 μl |
| Primers 1 and 2 (100 μM each) | 2 μl |
| Expand High Fidelity DNA polymerase | 1.75 U |
| Reaction volume | 50 μl |
| Reaction paramaters: | |
| 94° C. for 3 min | |
| 94° C./1 min, 58° C./1 min, 72° C./2 min, for 45 cycles | |
| 72° C. for 15 min. | |

EXAMPLE 7

Isolation of Genomic DNA and Southern Analysis

Genomic DNA was extracted from tomato leaves by grinding 10 grams of tomato leaf tissue to a fine powder in liquid nitrogen. 37.5 ml of a mixture containing 25 ml homogenization buffer [100 mM Tris-HCl, pH 8.0, 100 mm EDTA, 250 mM NaCl, 1% sarkosyl, 1% 2-mercaptoethanol, 10 μg/ml RNase and 12.5 ml phenol] prewarmed to 60° C. was added to the ground tissue. The mixture was shaken for fifteen minutes. An additional 12.5 ml of chloroform/isoamyl alcohol (24:1) was added to the mixture and shaken for another 15 minutes. The mixture was centrifuged and the aqueous phase reextracted with 25 ml phenol/chloroform/isoamylalcohol (25:24:1) and chloroform/isoamylalcohol (24:1). The nucleic acids were recovered by precipitaion with 15 ml isopropanol at room temperature. The precipitate was resuspended in 1 ml of water.

Genomic DNA was subjected to restriction enzyme digestion as follows: 10 μg genomic DNA, 40 μl 10x reaction buffer and 100 U restriction enzyme (XbaI, EcoRI, EcoRV or HinDIII) were reacted for five to six hours in a total reaction volume of 400 μl. The mixture was then phenol-extracted and ethanol-precipitated. The digested DNA was subjected to agarose gel electrophoresis on a 0.8% agarose gel at 15 volts for approximately 15 hours. The gel was submerged in denaturation buffer [87.66 g NaCl and 20 g NaOH/Liter] for 30 minutes with gentle agitation, rinsed in distilled water and submerged in neutralization buffer [87.66 g NaCl and 60.55 g tris-HCl, pH 7.5/Liter] for 30 minutes with gentle agitation. The DNA was transferred to a Hybond-N⁺ nylon membrane by capillary blotting.

Hybridization was performed overnight at 42° C. using 1×10⁶ cpm/ml of ³²P-dCTP-labeled full length DHS cDNA or 3'-non-coding region of the DHS cDNA clone. Prehybridization and hybridization were carried out in buffer containing 50% formamide, 6×SSC, 5× Denhardt's solution, 0.1% SDS and 100 mg/ml denatured salmon sperm DNA. The membrane was prehybridized for two to four hours; hybridization was carried out overnight.

After hybridization was complete, membranes were rinsed at room temperature in 2×SSC and 0.1% SDS and then washed in 2×SSC and 0.1% SDS for 15 minutes and 0.2×SSC and 0.1% SDS for 15 minutes. The membrane was then exposed to x-ray film at −80° C. overnight. The results are shown in FIG. 5.

EXAMPLE 8

Isolation of a Senescence-Induced eIF-5A Gene from *Arabidopsis*

A full-length cDNA clone of the senescence-induced eIF-5A gene expressed in *Arabidopsis* leaves was obtained by PCR using an *Arabidopsis* senescing leaf cDNA library as template. Initially, PCR products corresponding to the 5'- and 3'-ends of the gene were made using a degenerate upstream primer <AAARRYCGMCCYTGCAAGGT> (SEQ ID NO:17) paired with vector T7 primer <AATAC-GACTCACTATAG> (SEQ ID NO:18), and a degenerate downstream primer <TCYTTNCCYTCMKCTAAHCC> (SEQ ID NO:19) paired with vector T3 primer <ATTAAC-CCTCACTAAAG> (SEQ ID NO: 20). The PCR products were subcloned into pBluescript for sequencing. The full-length cDNA was then obtained using a 5'-specific primer <CTGTTACCAAAAAATCTGTACC> (SEQ ID NO: 21) paired with a 3'-specific primer <AGAAGAAG-TATAAAAACCATC> (SEQ ID NO: 22), and subcloned into pBluescript for sequencing.

EXAMPLE 9

Isolation of a Senescence-Induced eIF-5A Gene from Tomato Fruit

A full-length cDNA clone of the senescence-induced eIF-5A gene expressed in tomato fruit was obtained by PCR using a tomato fruit cDNA library as template. Initially, PCR products corresponding to the 5'- and 3'-ends of the gene were made using a degenerate upstream primer (SEQ ID NO:17) paired with vector T7 primer (SEQ ID NO:18), and a degenerate downstream primer (SEQ ID NO:19) paired with vector T3 primer (SEQ ID NO: 20). The PCR products were subcloned into pBluescript for sequencing. The full-length cDNA was then obtained using a 5'-specific primer <AAAGAATCCTAGAGAGAGAAAGG> (SEQ ID NO: 23) paired with vector T7 primer (SEQ ID NO: 18), and subcloned into pBluescript for sequencing.

EXAMPLE 10

Isolation of a Senescence-Induced eIF-5A Gene from Carnation

A full-length cDNA clone of the senescence-induced eIF-5A gene expressed in carnation flowers was obtained by PCR using a carnation senescing flower cDNA library as template. Initially, PCR products corresponding to the 5'- and 3'-ends of the gene were made using a degenerate upstream primer (SEQ ID NO:17) paired with vector T7 primer (SEQ ID NO:18), and a degenerate downstream primer (SEQ ID NO:19) paired with vector T3 primer (SEQ ID NO: 20). The PCR products were subcloned into pBluescript for sequencing. The full-length cDNA was then obtained using a 5'-specific primer <TTTTACATCAATC-GAAAA> (SEQ ID NO: 24) paired with a 3'-specific primer <ACCAAAACCTGTGTTATAACTCC> (SEQ ID NO: 25), and subcloned into pBluescript for sequencing.

EXAMPLE 11

Isolation of a Senescence-Induced DHS Gene from *Arabidopsis*

A full-length cDNA clone of the senescence-induced DHS gene expressed in *Arabidopsis* leaves was obtained by screening an *Arabidopsis* senescing leaf cDNA library. The sequence of the probe (SEQ ID NO: 26) that was used for screening is shown in FIG. 38. The probe was obtained by PCR using the senescence leaf cDNA library as a template and primers (indicated as underlined regions in FIG. 38) designed from the unidentified genomic sequence (AB017060) in GenBank. The PCR product was subcloned into pBluescript for sequencing.

EXAMPLE 12
Isolation of a Senescence-Induced DHS Gene from Carnation

A full-length cDNA clone of the senescence-induced DHS gene expressed in carnation petals was obtained by screening a carnation senescing petal cDNA library. The sequence of the probe (SEQ ID NO: 27) that was used for screening is shown in FIG. 39. The probe was obtained by PCR using the senescence petal cDNA library as a template and degenerate primers (upstream: 5' TTG ARG AAG ATY CAT MAA RTG CCT 3') (SEQ ID NO: 28); downstream: 5' CCA TCA AAY TCY TGK GCR GTG TT 3') (SEQ ID NO: 29)). The PCR product was subcloned into pBluescript for sequencing.

EXAMPLE 13
Transformation of *Arabidopsis* with Full-Length or 3' Region of *Arabidopsis DHS* in
Antisense Orientation Agrobacteria were transformed with the binary vector, pKYLX71, containing the full-length senescence-induced *Arabidopsis* DHS cDNA sequence or the 3' end of the DHS gene (SEQ ID NO:30) (FIG. 36), both expressed in the antisense configuration, under the regulation of double 35S promoter. *Arabidopsis* plants were transformed with the transformed Agrobacteria by vacuum infiltration, and transformed seeds from resultant T$_0$ plants were selected on ampicillin.

FIGS. 21 through 24 are photographs of the transformed *Arabidopsis* plants, showing that expression of the DHS gene or 3' end thereof in antisense orientation in the transformed plants results in increased biomass, e.g., larger leaves and increased plant size. FIG. 25 illustrates that the transgenic *Arabidopsis* plants have increased seed yield.

EXAMPLE 14
Transformation of Tomato Plants with Full-Length or 3' Region of Tomato DHS in
Antisense Orientation Agrobacteria were transformed with the binary vector, pKYLX71, containing the full-length senescence-induced tomato DHS cDNA sequence or the 3' end of the DHS gene (SEQ ID NO:31) (FIG. 37), both expressed in the antisense configuration, under the regulation of double 35S promoter. Tomato leaf explants were formed with these Agrobacteria, and transformed callus and plantlets were generated and selected by standard tissue culture methods. Transformed plantlets were grown to mature fruit-producing T$_1$ plants under greenhouse conditions.

FIGS. 26 through 35 are photographs showing that reduced expression of the senescence-induced tomato DHS gene in the transformed plants results in increased biomass, e.g., larger leaf size and larger plants as seen in the transformed *Arabidopsis* plants, as well as delayed softening and spoilage of tomato fruit.

What is claimed is:

1. An isolated antisense polynucleotide of SEQ ID NO:5 wherein polynucleotide inhibits expression of an endogenous senescence-induced deoxyhypusine synthase gene comprising SEQ ID NO:5 when said antisense polynucleotide is transcribed in a plant cell.

2. A vector for transformation of plant cells comprising
   (a) the antisense polynucleotide of claim 1; and
   (b) regulatory sequences operatively linked to the antisense polynucleotide such that the antisense polynucleotide is transcribe in a plant cell into which it is transformed.

3. The vector according to claim 2 wherein the regulatory sequences comprise a promoter and a transcription termination region.

4. The vector according to claim 2 wherein the regulatory sequences comprise a constitutive promoter.

5. The vector according to claim 2 wherein the regulatory sequences comprise a plant tissue-specific promoter.

6. The vector according to claim 2 wherein the regulatory sequences comprise a senescence-induced plant promoter.

7. The vector according to claim 2 wherein the regulatory sequences comprise a viral promoter.

8. The antisense polynucleotide according to claim 1 wherein the antisense polynucleotide is the complement of SEQ ID NO:30.

9. A bacterial cell transformed with the vector according to claim 2.

10. A transgenic plant cell transformed with the vector according to claim 2.

11. A transgenic plant grown from the plant cell of claim 10.

12. A plant part obtained from the plant of claim 11 or progeny of said plant, wherein the plant part or progeny comprises the vector of claim 2 wherein the plant part is a fruit, flower, or leaf.

13. A method for inhibiting the expression of endogenous senescence-induced deoxyhypusine synthase gene comprising SEQ ID NO:5 in a plant, said method comprising
   (1) integrating into the genome of at least one cell of the plant the vector of claim 2 and
   (2) growing said plant, whereby said antisense polynucleotide inhibits expression of the senescence-induced deoxyhypusine synthase gene comprising SEQ ID NO:5.

14. The method according to claim 13 wherein said inhibition of expression results in increased biomass of said plant as compared to biomass of a wild type plant not having been transformed with the vector of claim 2.

15. The method according to claim 13 wherein said inhibition of expression results in delayed fruit softening and spoilage in said plant as compared to a fruit softening and spoilage of wild type plant not having been transformed with the vector of claim 2.

16. The method according to claim 13 wherein said inhibition of expression results in increased seed volume from said plant as compared to seed volume from a wild type not having been transformed with the vector of claim 2.

17. The method according to claim 13 wherein the regulatory sequences comprise a constitutive promoter active in the plant.

18. The method according to claim 13 wherein the regulatory sequences comprise a tissue specific promoter active in the plant.

19. The method according to claim 13 wherein the regulatory sequences comprise a senescence-induced promoter active in the plant.

20. The method according to claim 13 wherein said plant is selected from the group consisting of fruit bearing plants and flowering plants.

21. The method according to claim 13 wherein the plant is a flowering plant.

22. A plasmid comprising a replication system functional in a prokaryotic host and the antisense polynucleotide according to claim 1.

23. A plasmid comprising a replication system functional in *Agrobacterium* and the antisense polynucleotide according to claim 1.

24. A vector for transformation of plant cells comprising
   (a) the antisense polynucleotide of claim 8; and
   (b) regulatory sequences operatively linked to the antisense polynucleotide such that the antisense polynucleotide is transcribed in a plant cell into which it is transformed.

25. A method for inhibiting the expression of endogenous senescence-induced deoxyhypusine synthase gene comprising SEQ ID NO:5 in a plant, said method comprising
   (1) integrating into the genome of at least one cell of the plant the vector of claim 24; and
   (2) growing said plant, whereby said antisense polynucleotide sequence is transcribed and whereby said transcription of the antisense polynucleotide inhibits expression of the senescence-induced deoxyhypusine synthase gene comprising SEQ ID NO:5.

* * * * *